US007582415B2

(12) United States Patent
Straus

(10) Patent No.: US 7,582,415 B2
(45) Date of Patent: Sep. 1, 2009

(54) RAPID DETECTION OF REPLICATING CELLS

(76) Inventor: Don Straus, 19 Buckingham St., Cambridge, MA (US) 02138

( * ) Notice: Subject to any disclaimer, the term of this patent is extended or adjusted under 35 U.S.C. 154(b) by 410 days.

(21) Appl. No.: 10/236,107

(22) Filed: Sep. 6, 2002

(65) Prior Publication Data

US 2003/0082516 A1    May 1, 2003

Related U.S. Application Data

(60) Provisional application No. 60/317,658, filed on Sep. 6, 2001.

(51) Int. Cl.
C12Q 1/00 (2006.01)
C12Q 1/04 (2006.01)
C12M 1/34 (2006.01)
G01N 33/53 (2006.01)
G01N 33/567 (2006.01)
G01N 33/554 (2006.01)
G01N 33/569 (2006.01)

(52) U.S. Cl. .............. 435/4; 435/34; 435/7.2; 435/7.22; 435/7.31; 435/7.32; 435/7.33; 435/7.34; 435/7.35; 435/7.37; 435/36; 435/37; 435/38; 435/39; 435/287.1

(58) Field of Classification Search .......... 422/55, 422/82.11; 435/6, 7.2, 7.32, 7.72, 34, 808, 435/810, 4, 7.22, 7.31, 7.33, 7.34, 7.35, 7.37, 435/36, 37, 38, 39, 287.1
See application file for complete search history.

(56) References Cited

U.S. PATENT DOCUMENTS

| 3,694,317 | A | * | 9/1972 | Scher ........................ 435/39 |
| 4,587,213 | A | * | 5/1986 | Malecki ..................... 435/39 |
| 4,959,301 | A | * | 9/1990 | Weaver et al. ............... 435/5 |
| 5,190,666 | A | | 3/1993 | Bisconte |
| 5,292,644 | A | | 3/1994 | Berg |
| 5,306,420 | A | | 4/1994 | Bisconte |
| 5,321,545 | A | | 6/1994 | Bisconte |
| 5,366,867 | A | | 11/1994 | Kawakami et al. |
| 5,474,910 | A | | 12/1995 | Alfano |
| 5,510,246 | A | | 4/1996 | Morgan |
| 5,552,272 | A | * | 9/1996 | Bogart ........................ 435/6 |
| 5,604,351 | A | | 2/1997 | Bisconte |
| 5,663,057 | A | | 9/1997 | Drocourt et al. |
| 5,792,617 | A | * | 8/1998 | Rotman .................... 435/7.23 |
| 5,821,066 | A | * | 10/1998 | Pyle et al. .................. 435/7.2 |
| 5,828,716 | A | | 10/1998 | Bisconte de Saint Julien |
| 5,861,270 | A | | 1/1999 | Nelis |
| 5,968,766 | A | | 10/1999 | Powers |
| 5,976,892 | A | | 11/1999 | Bisconte |
| 5,981,180 | A | | 11/1999 | Chandler et al. |
| 6,122,396 | A | | 9/2000 | King et al. |
| 6,268,222 | B1 | | 7/2001 | Chandler et al. |
| 6,472,166 | B1 | | 10/2002 | Wardlaw et al. |
| 6,664,528 | B1 | | 12/2003 | Cartlidge et al. |
| 6,710,879 | B1 | | 3/2004 | Hansen et al. |
| 6,919,960 | B2 | | 7/2005 | Hansen et al. |
| 7,068,365 | B2 | | 6/2006 | Hansen et al. |
| 2003/0143580 | A1 | | 7/2003 | Straus |
| 2003/0170613 | A1 | | 9/2003 | Straus |
| 2004/0246483 | A1 | | 12/2004 | Hansen et al. |
| 2005/0148085 | A1 | | 7/2005 | Larsen |
| 2005/0225766 | A1 | | 10/2005 | Hansen et al. |
| 2006/0256340 | A1 | | 11/2006 | Hansen et al. |

FOREIGN PATENT DOCUMENTS

| JP | H11-346795 | 12/1999 |
| WO | WO 99/58948 | 11/1999 |

OTHER PUBLICATIONS

Anonymous, The Brain, Enchanted Learning.com, http://www.enchantedlearning.com/subjects/anatomy/brain, neuron.shtml, Copyright 2001-2007, Printed Nov. 4, 2007, pp. 1-4.*
Wolniak, S.M. 2004. BSCI 427 Principles of Microscopy Fall 2004 Syllabus. 8 Pages. http://www.life.umd.edu/cbmg/faculty/wolniak/wolniac/micro.html. Printed Nov. 8, 2007.*
Colony Counter (http://www.topac.com/acolyte.html).
Colony Counter Models and Specifications (http://www.biologics-inc.com/cc-models.htm).
Corkidi et al., "COVASIAM: An Image Analysis Method That Allows Detection of Confluent Microbial Colonies and Colonies of Various Sizes for Automated Counting," *Appl. Environ. Microbiol.* 64:1400-1404. (1998).
Digital Multi-Purpose High-Resolution Colony and Plaque Counter (http://www.loats.com/mla.html).
Esteban et al., "Improved Direct Epifluorescent Filter Technique for Rapid Bioburden Control in Intravenous Solutions," *J. Parenter. Sci. Technol.* 46:146-149 (1992).
Loats et al., "LAI High-Resolution Automated Colony Counting System—Mouse Lymphoma Assay: Performance Analysis," (http://www.loats.com/docs/HRCCval/HRCCval.htm).
System Specifications (http//www.loats.com/order_info.html) (1999).
Wilson, "Use of the IUL Countermat Automatic Colony Counter for Spiral Plated Total Viable Counts," *Appl. Environ. Microbiol.* 61:3158-3160 (1995).
Yasui et al., "Imaging of *Lactobacillus brevis* Single Cells and Microcolonies without a Microscope by an Ultrasensitive Chemiluminescent Enzyme Immunoassay with a Photon-Counting Television Camera," *Appl. Environ. Microbiol.* 63:4528-4533 (1997).

* cited by examiner

*Primary Examiner*—Jon Weber
*Assistant Examiner*—Kailash C Srivastava
(74) *Attorney, Agent, or Firm*—Clark & Elbing LLP

(57) ABSTRACT

The invention enables efficient, rapid, and sensitive enumeration of living cells by detecting microscopic colonies derived from in situ cell division using large area imaging. Microbial enumeration tests based on the invention address an important problem in clinical and industrial microbiology—the long time needed for detection in traditional tests—while retaining key advantages of the traditional methods based on microbial culture. Embodiments of the invention include non-destructive aseptic methods for detecting cellular microcolonies without labeling reagents. These methods allow for the generation of pure cultures which can be used for microbial identification and determination of antimicrobial resistance.

99 Claims, 22 Drawing Sheets

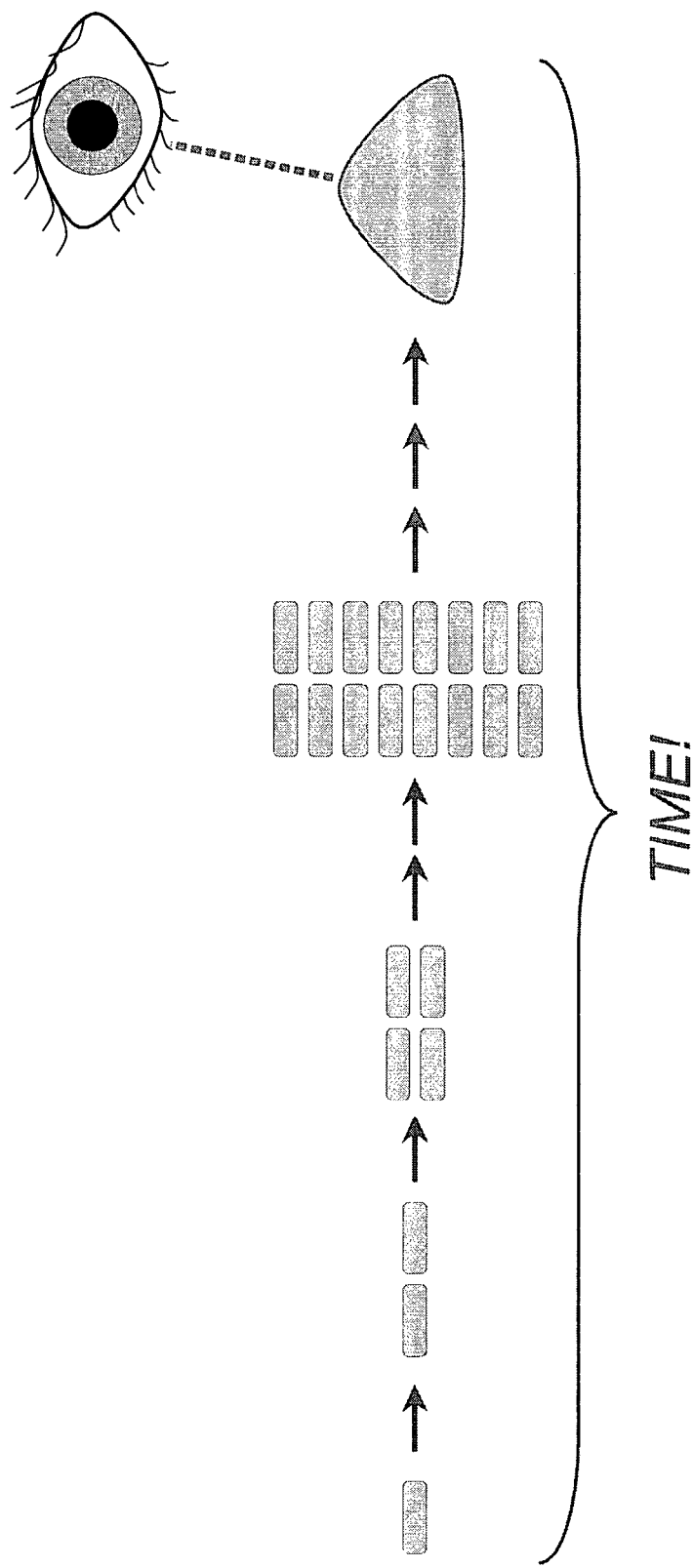
FIG. 1. Traditional microbial culture requires many generations of cell division

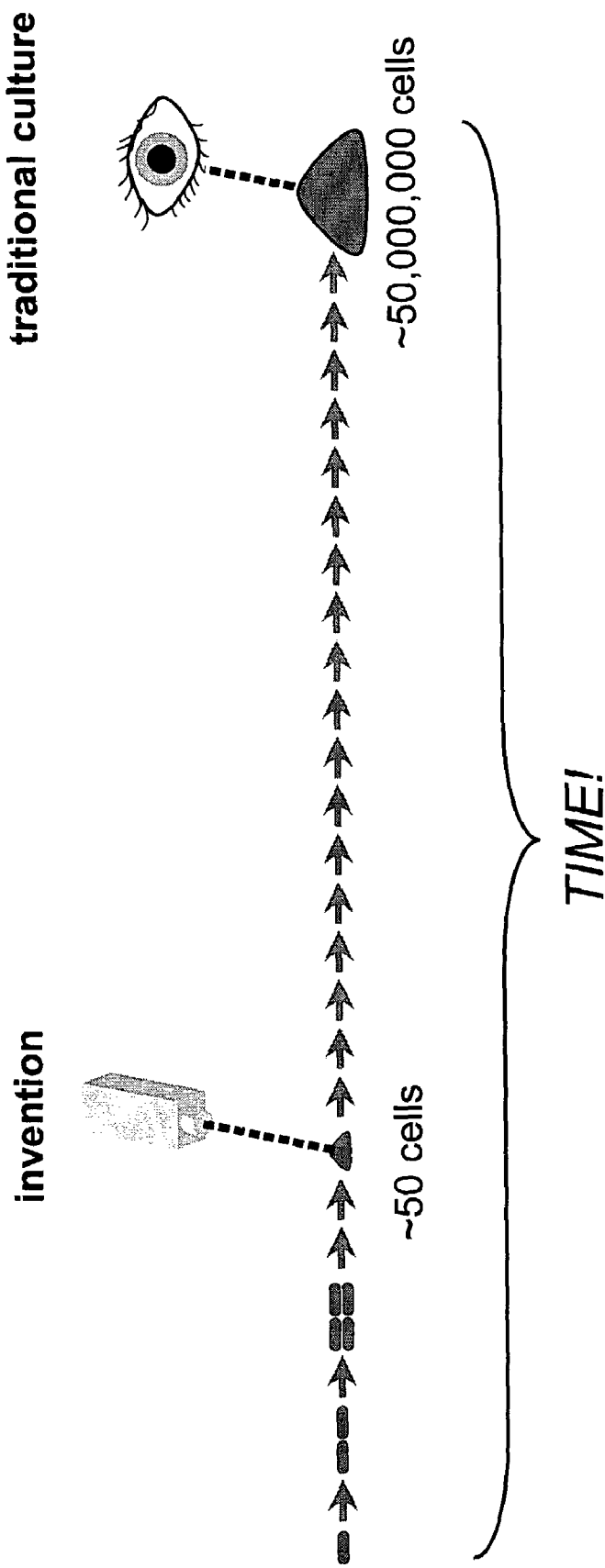
FIG. 2. The concept for rapid detection of microbial growth by detecting microcolonies.

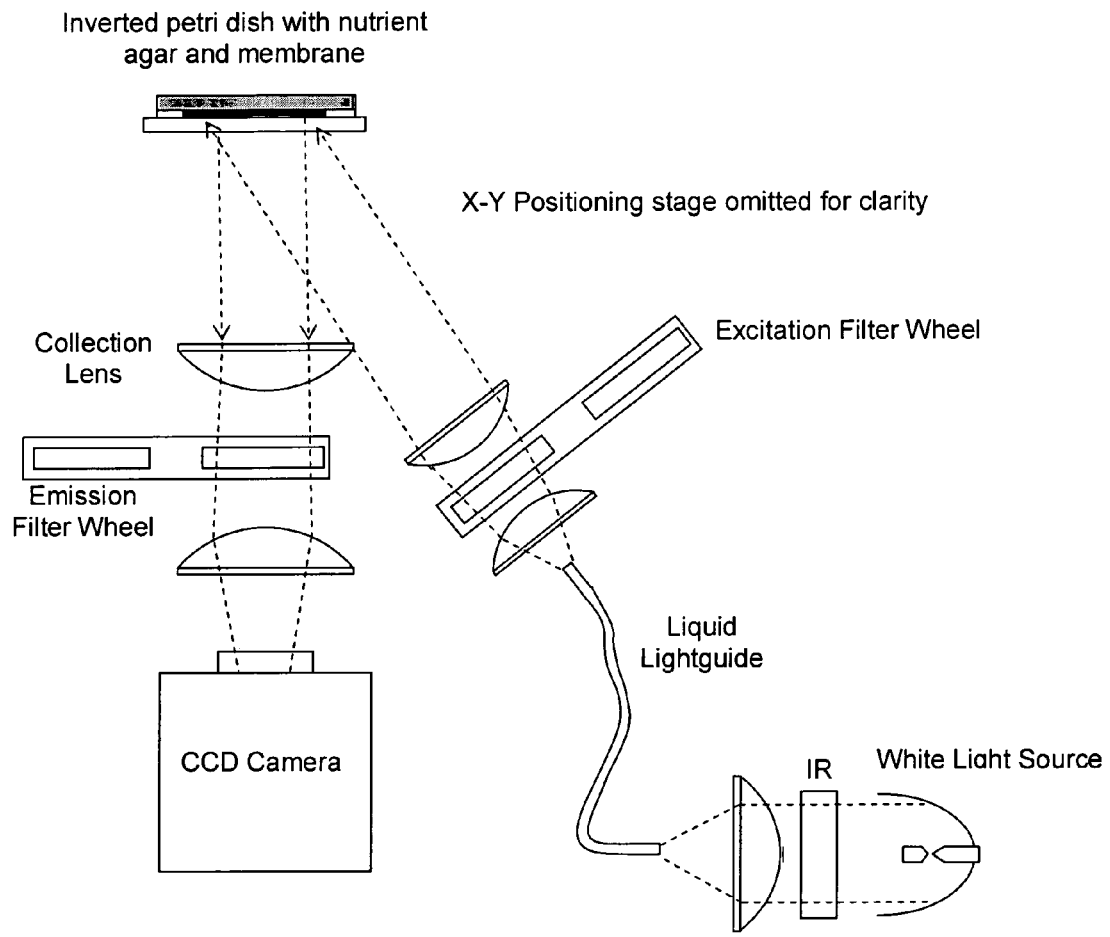
Figure 3. Scheme for a CCD imager for non-magnified large area imaging

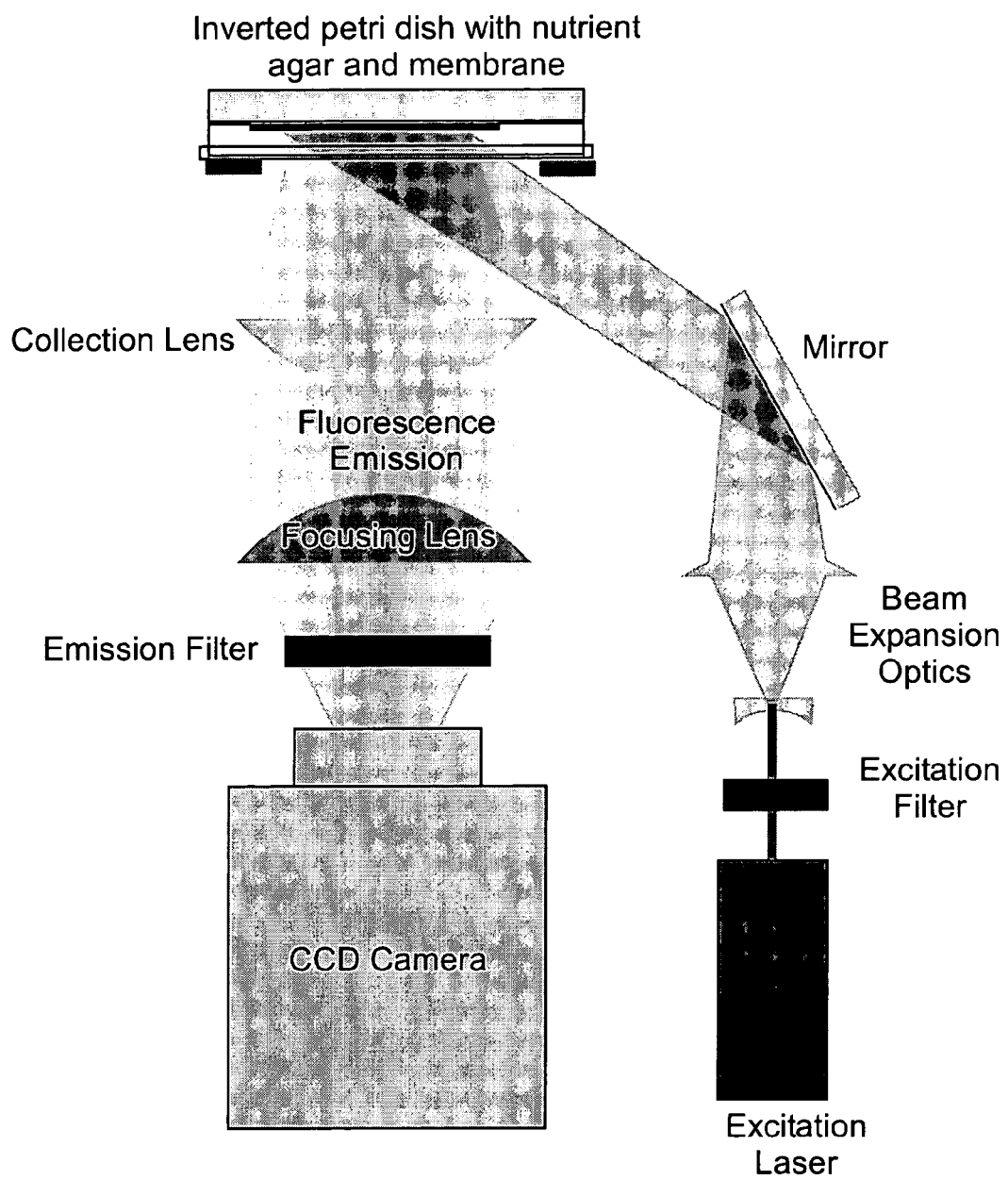
Figure 4. Scheme of a CCD imaging system for non-magnified large area imaging.

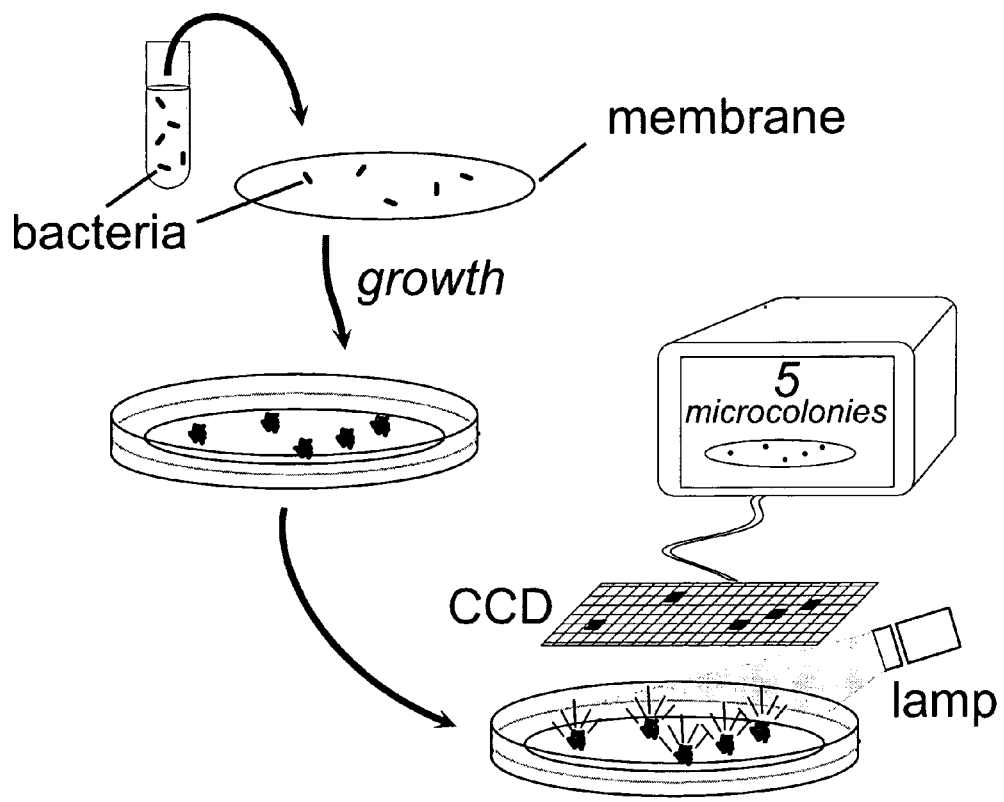
Figure 5. Scheme for reagent-less detection of microcolonies using non-magnified large area imaging.

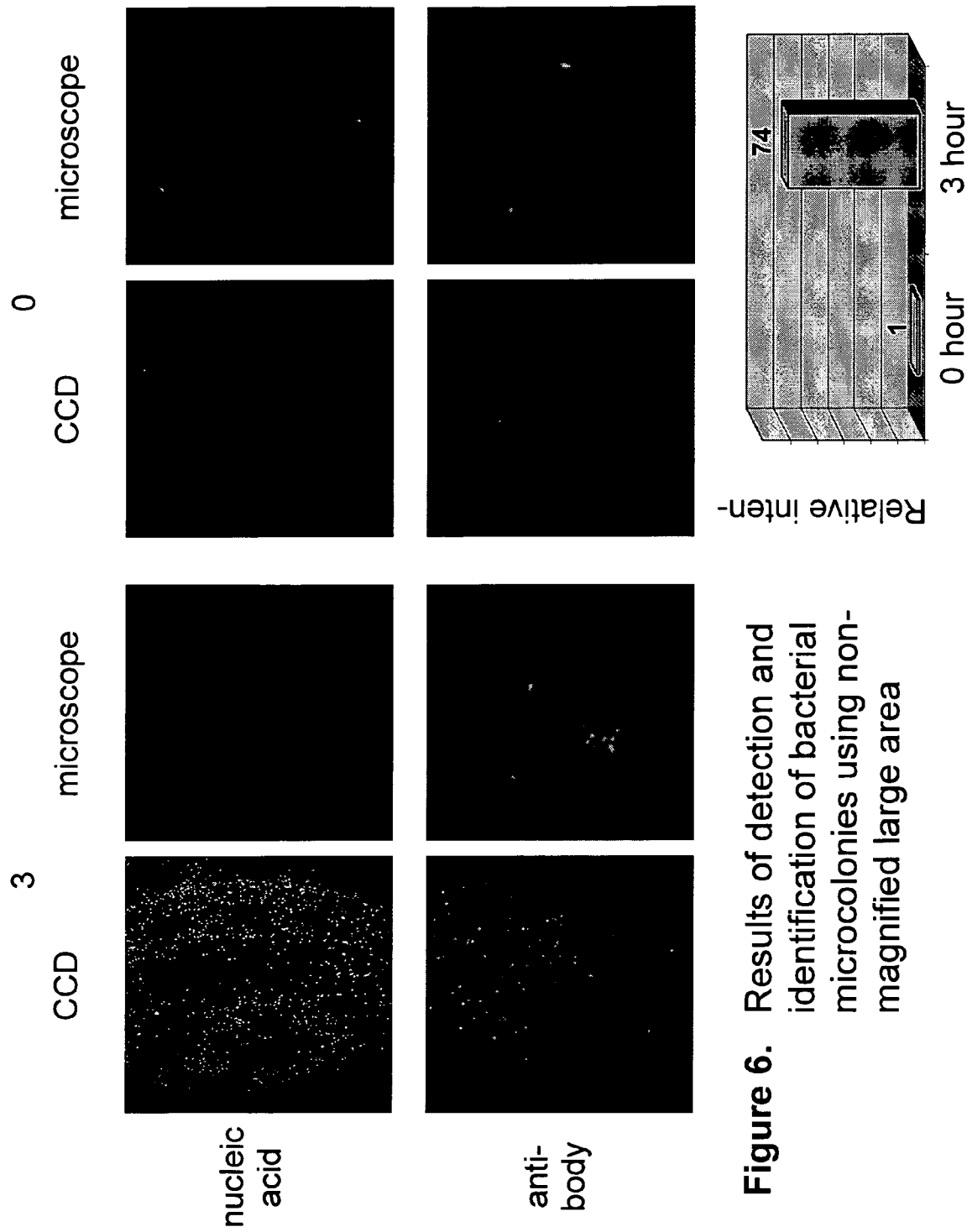
Figure 6. Results of detection and identification of bacterial microcolonies using non-magnified large area

Figure 7. Results of autofluorescence-based detection of bacterial microcolonies using non-magnified large area imaging (Example 2).

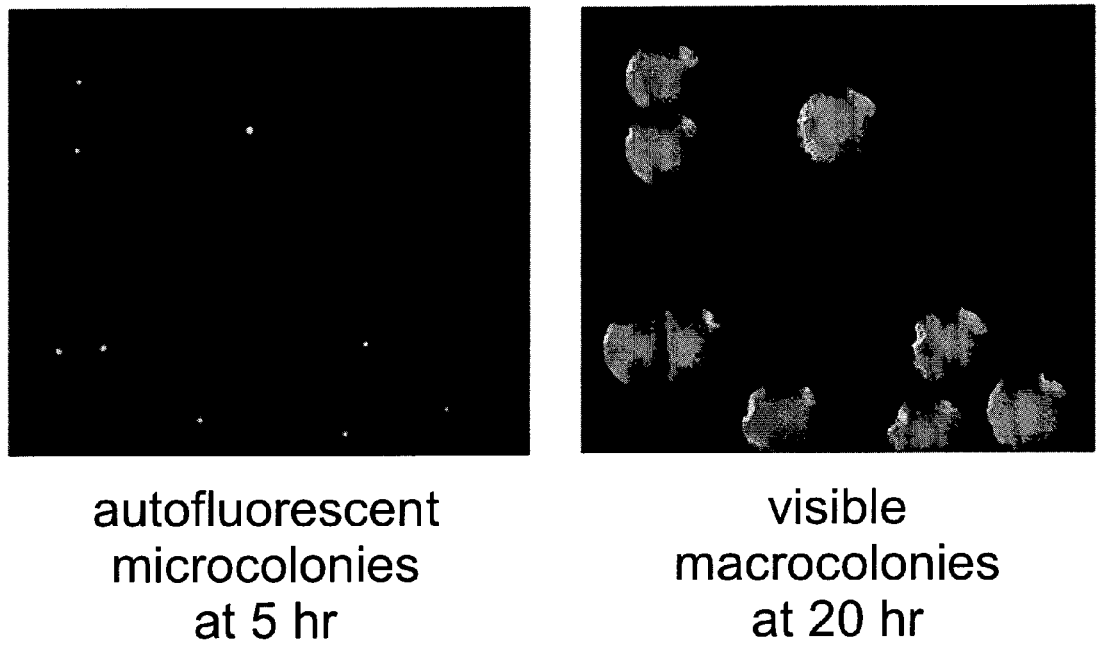
Figure 8. Results of a simple method for validating a rapid reagent-less microbial enumeration test using an internal comparison to the traditional culture method (Example 3).

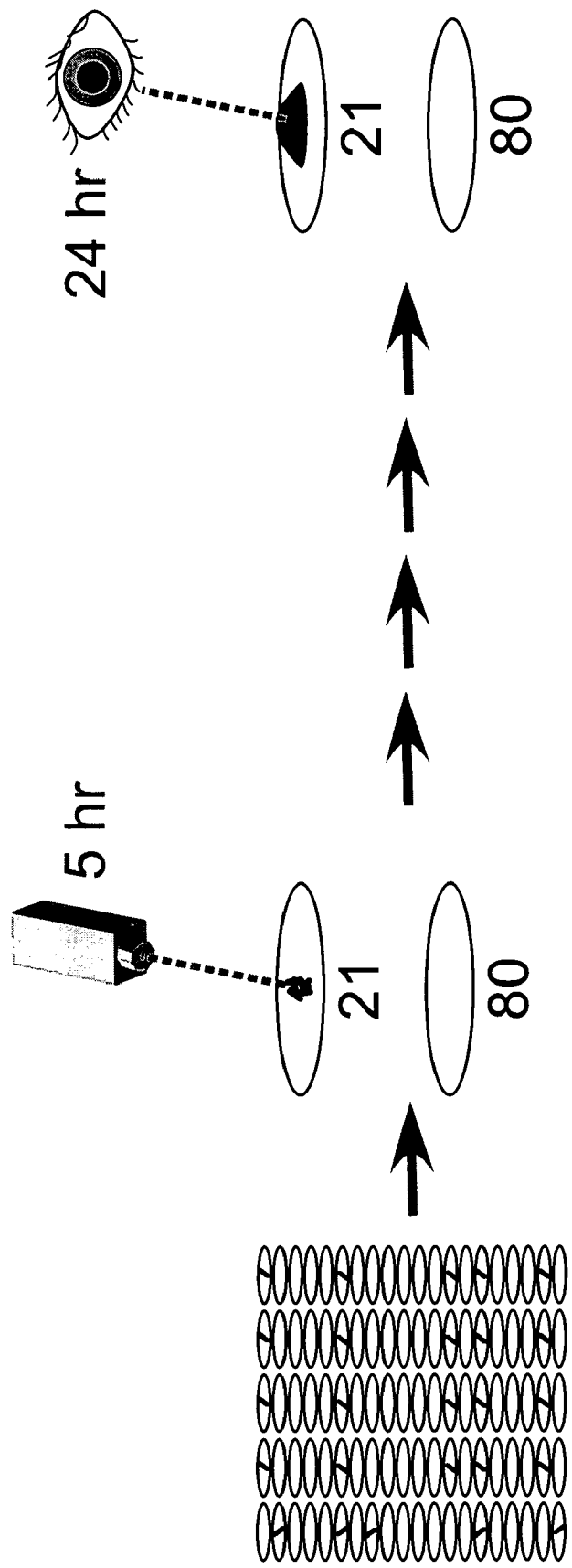
Figure 9. Scheme of a method for showing the accuracy and limit of detection of autofluorescent microcolony detection using non-magnified large area imaging (Example 4).

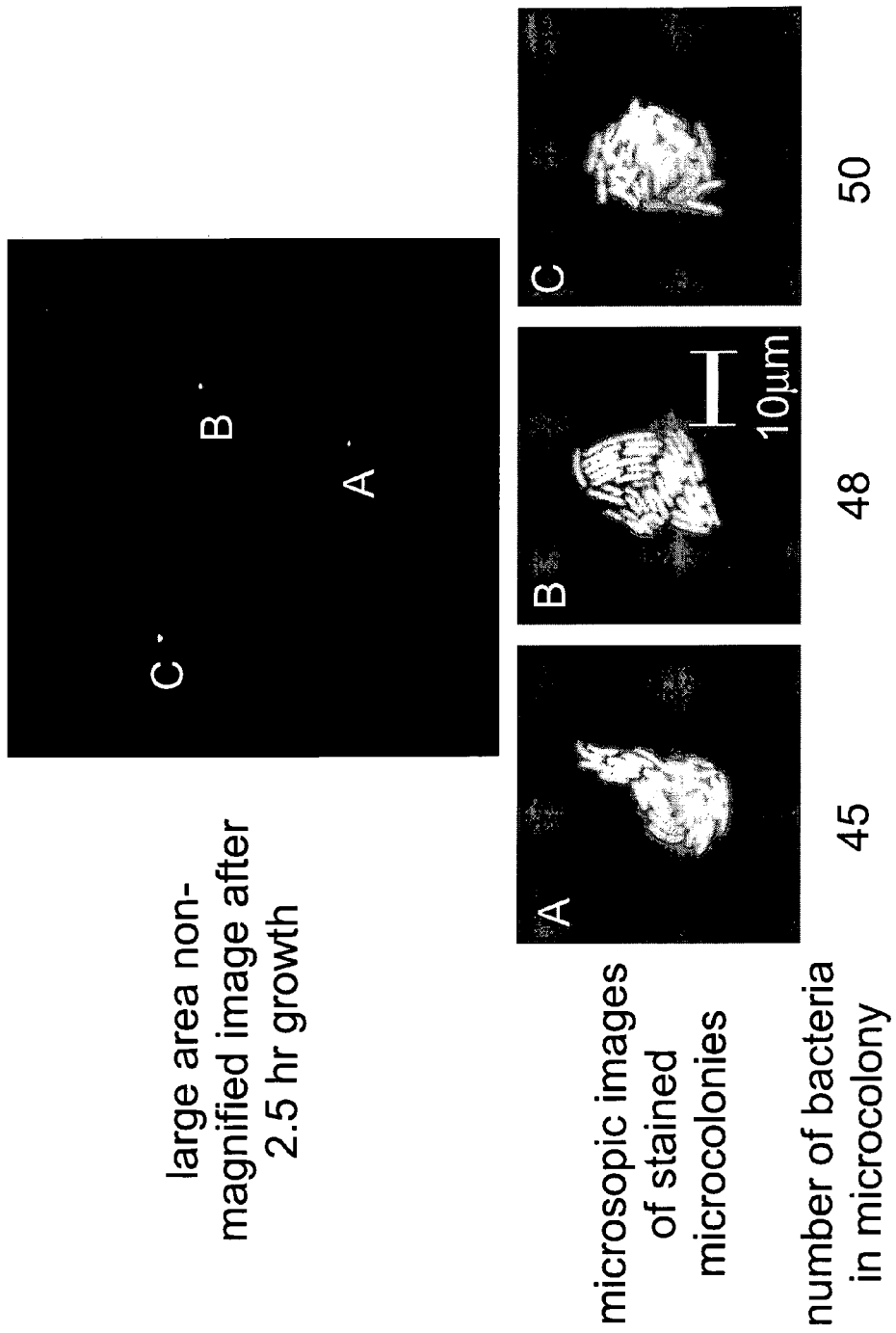
Figure 10. Results of an experiment to determine the number of microbial cells in autofluorescent bacterial microcolonies that were rapidly detected using reagent-less non-magnified imaging (Example 5).

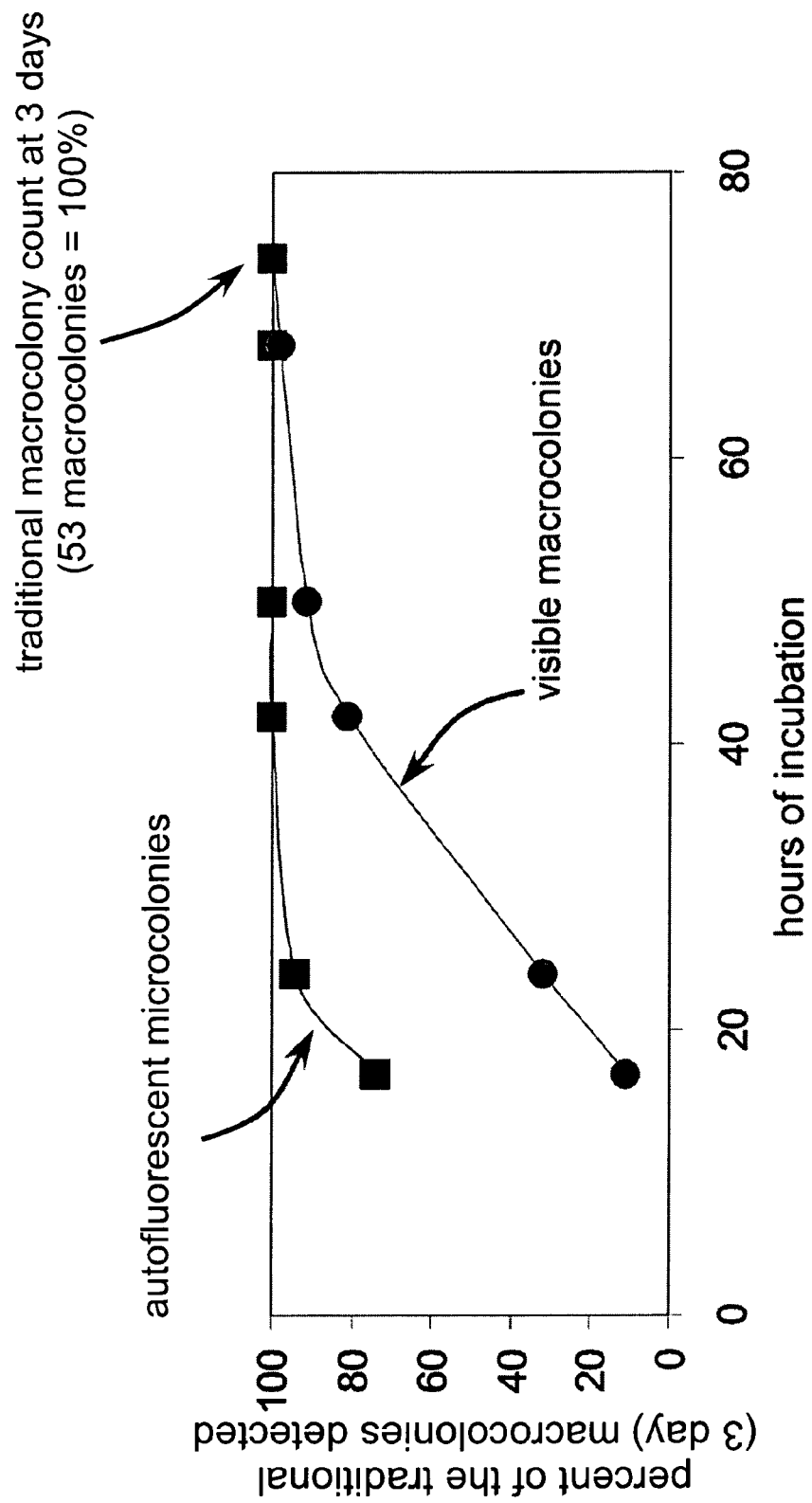
Figure 11. Results of enumerating bacteria in an environmental water sample (Example 6).

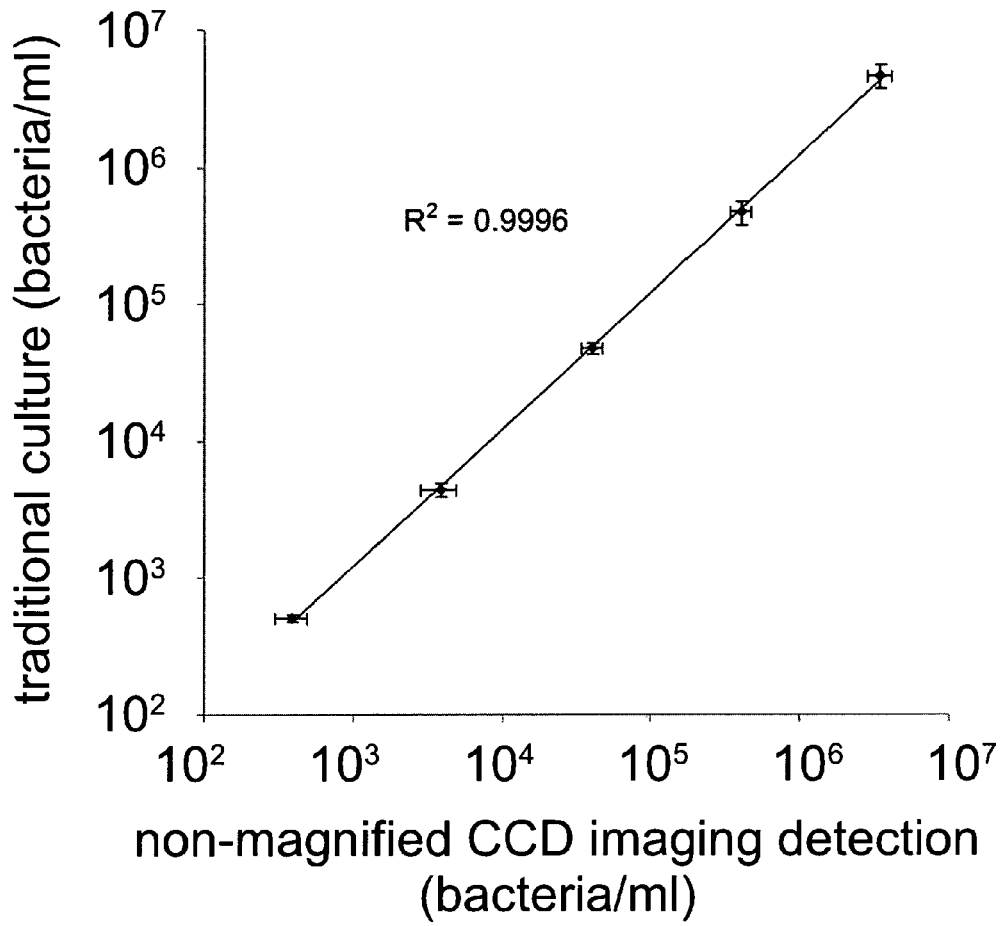
Figure 12. Graph showing correlation between enumeration tests using the invention and traditional culture (Example 7).

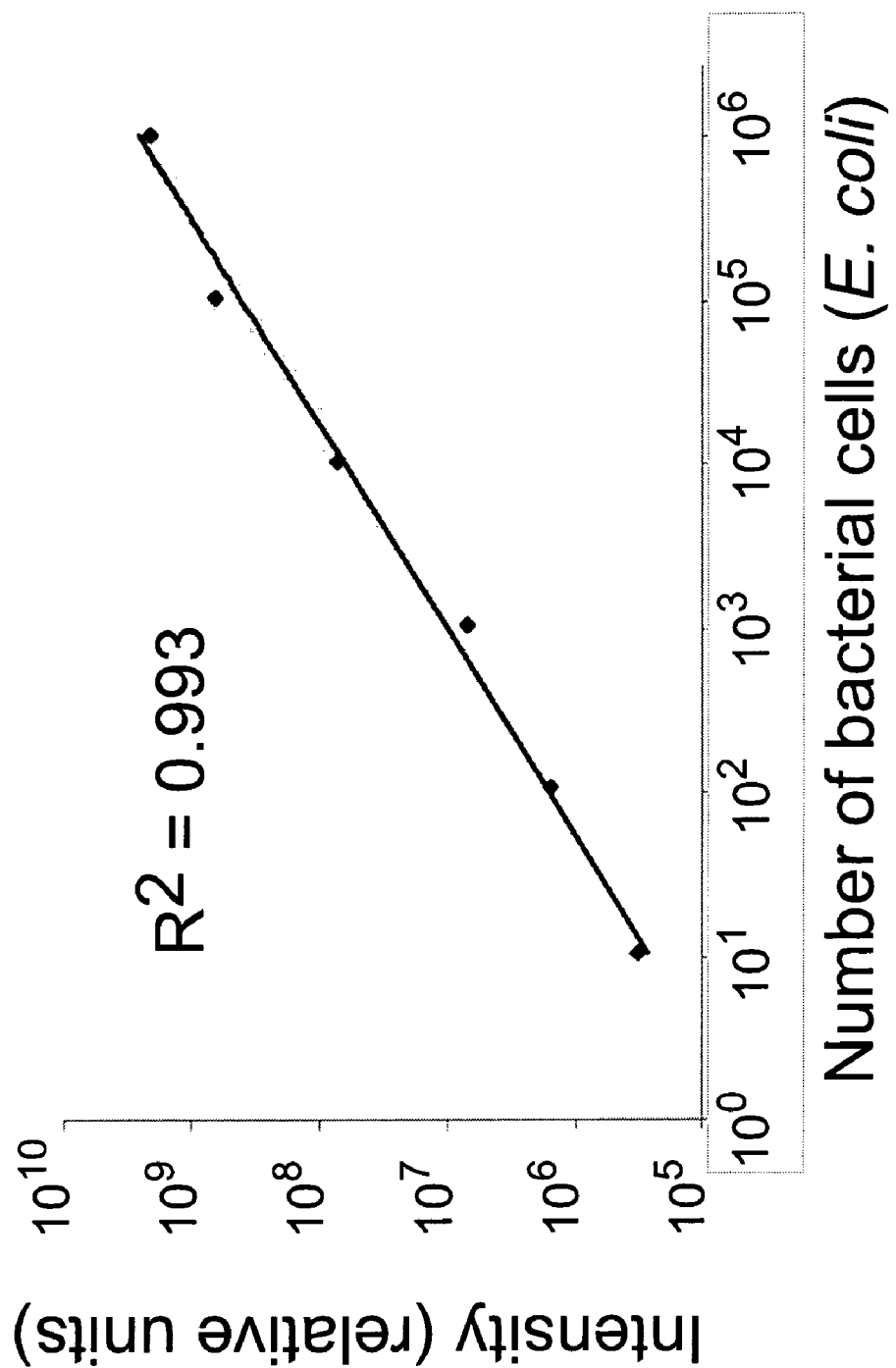
Figure 13. Results showing dynamic range and linearity of a reagent-less enumeration test (Example 8).

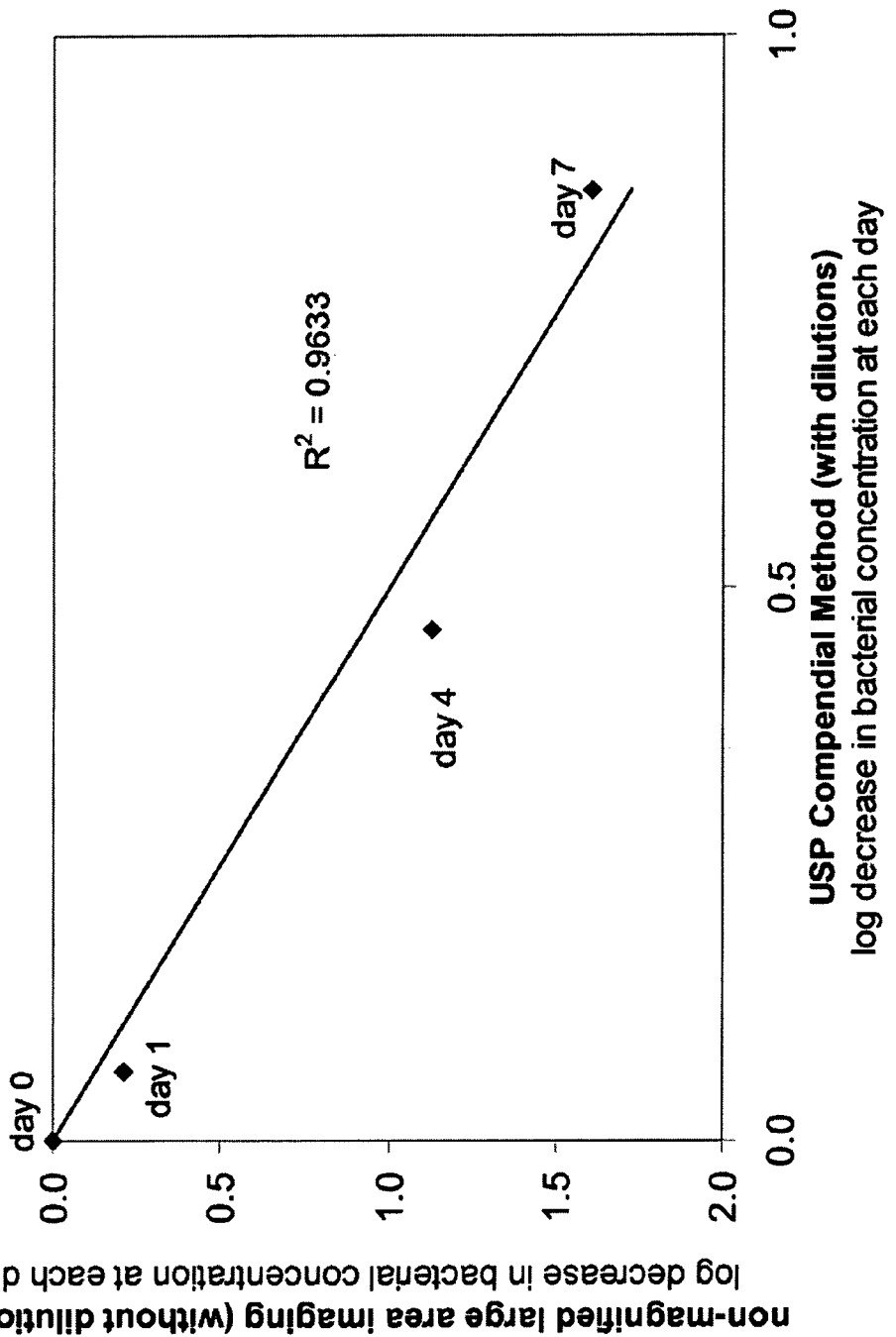
Figure 14. Results of antimicrobial preservative effectiveness testing without sample dilutions (Example 9).

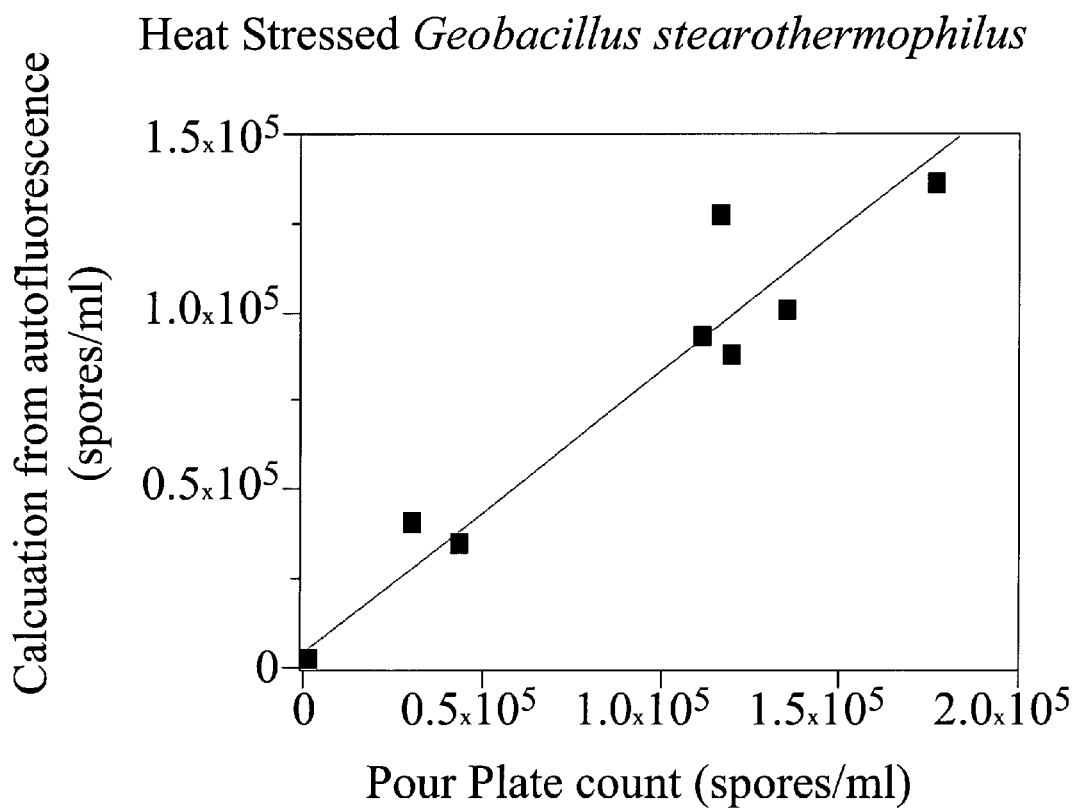
Figure 15. Results of autofluorescence-based detection of heat-stressed biological using non-magnified large area imaging (Example 10).

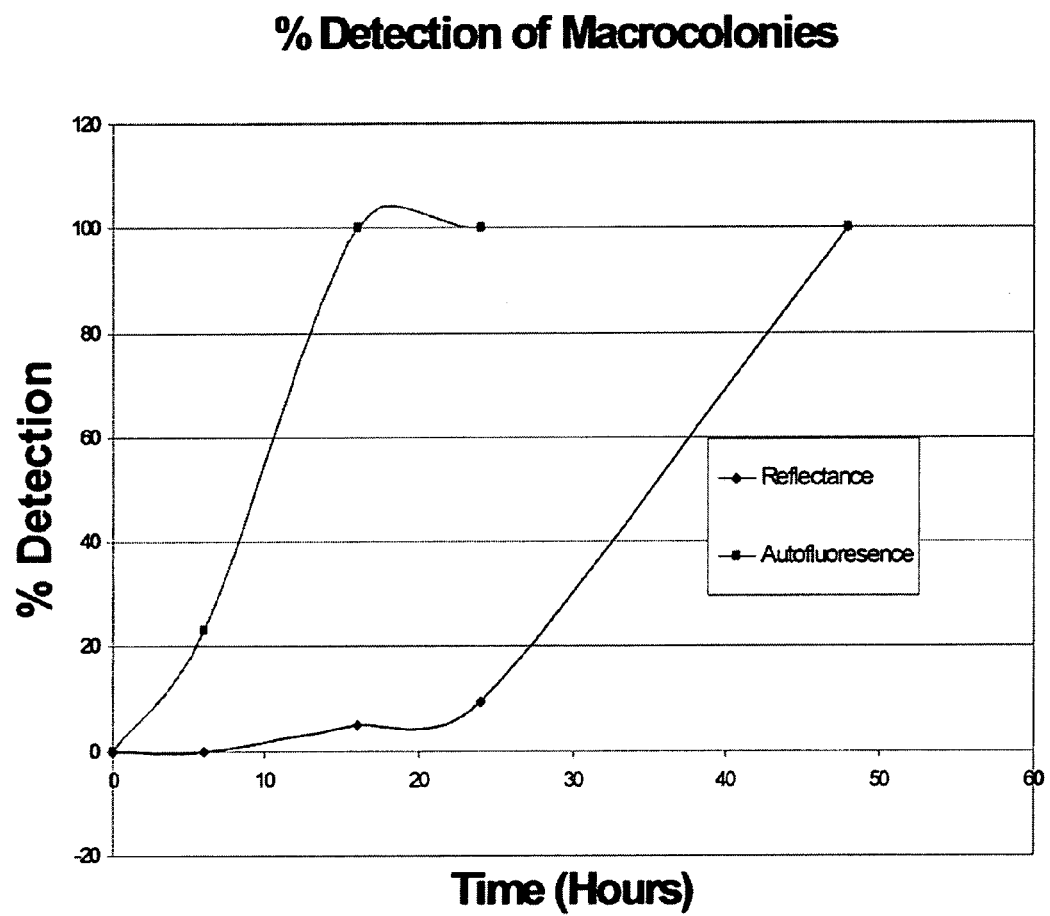
Figure 16. Results of autofluorescence-based detection of bacterial microcolonies in ground beef (Example 11).

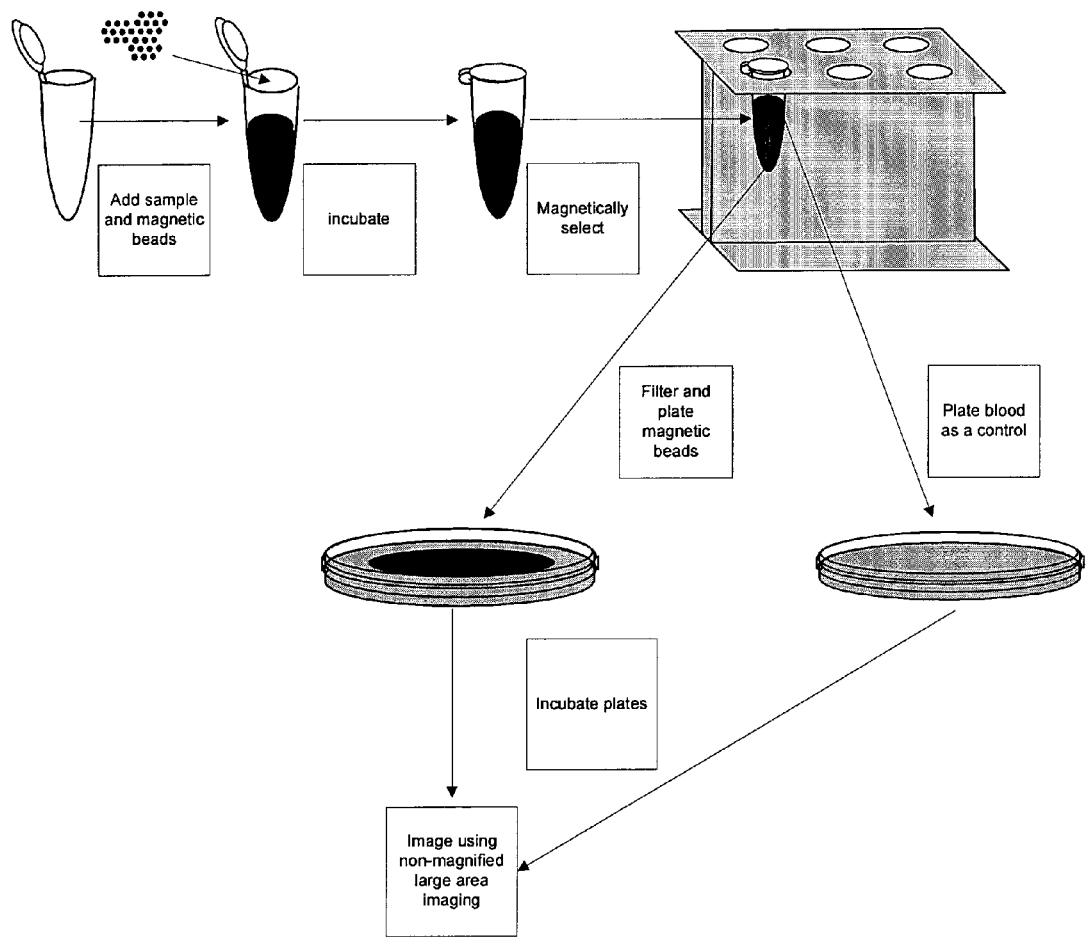
Figure 17. Scheme for magnetic selection followed by microcolony detection (Example 12).

0 hour image       6 hour image
 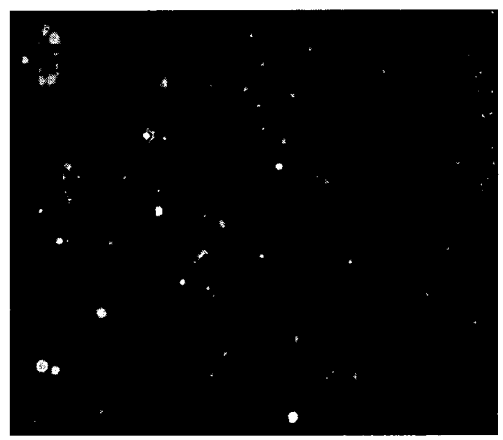
Figure 18. Results of detection of bacteria in a complex sample with non-specific magnetic selection followed by microcolony detection using non-magnified large area imaging(Example 12).

Scheme for rapid antimicrobial susceptibility testing (Example 13).

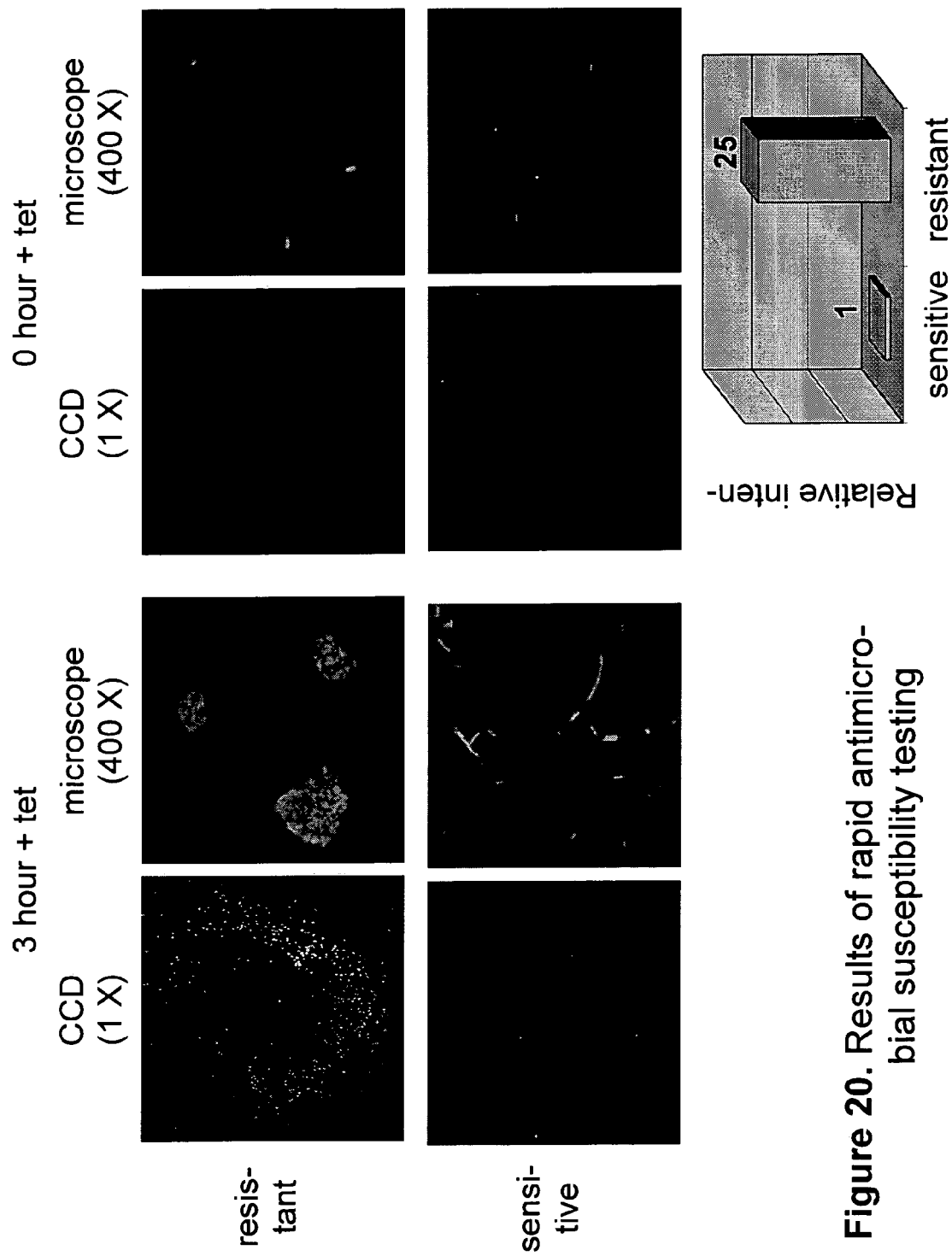
Figure 20. Results of rapid antimicrobial susceptibility testing

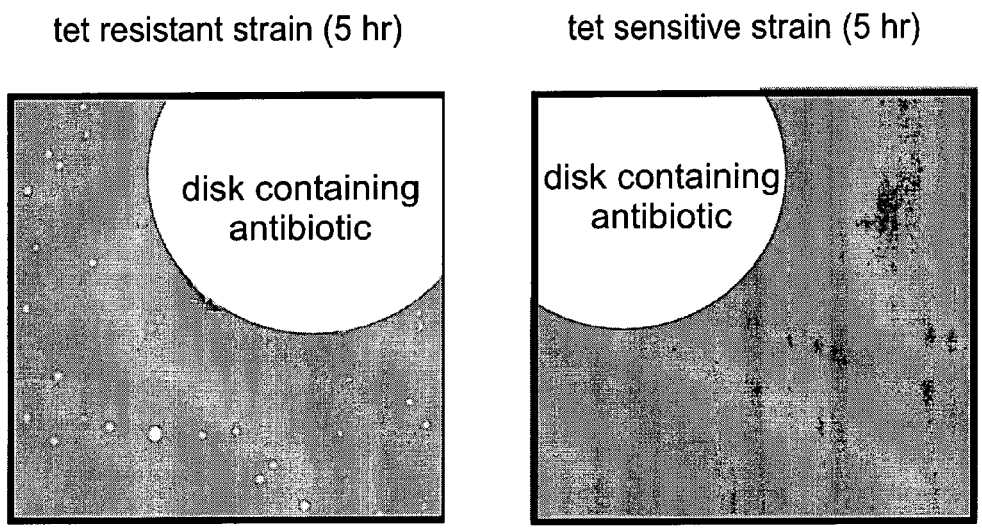
Figure 21. Results of rapid antimicrobial susceptibility testing using the disk diffusion method and non-magnified large area imaging (Example 14).

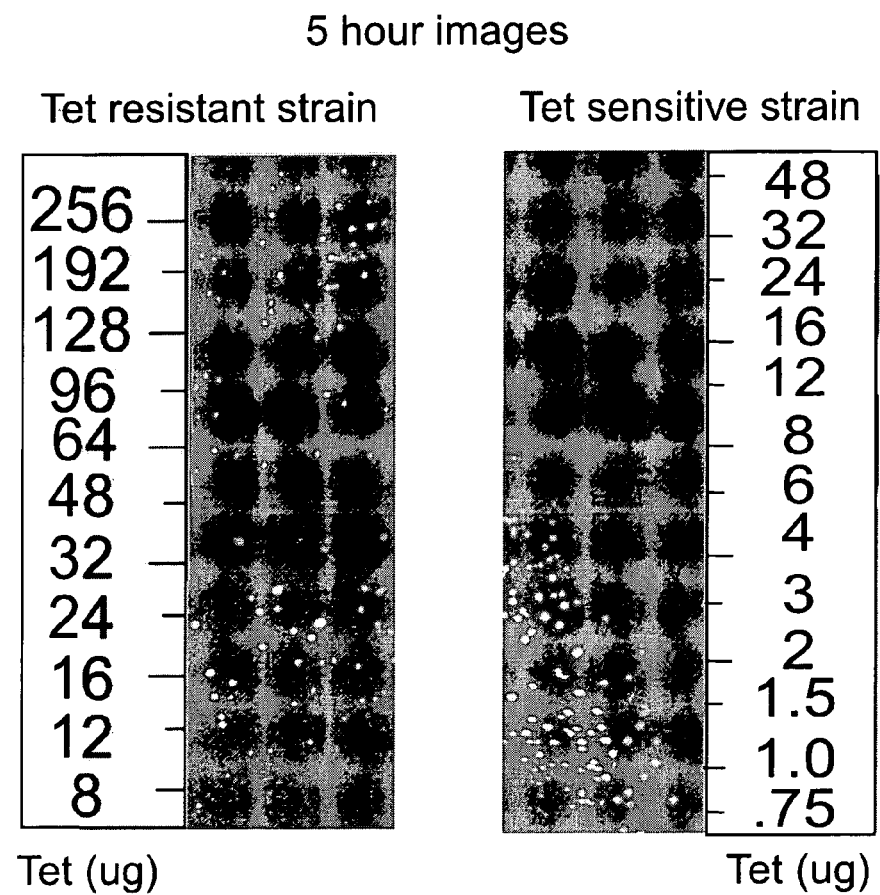
Figure 22. Results of rapid antimicrobial susceptibility testing using the E-test™ and non-magnified large area imaging (Example 15).

RAPID DETECTION OF REPLICATING CELLS

CROSS-REFERENCE TO RELATED APPLICATIONS

This application claims priority from U.S. Provisional Application No. 60/317,658, filed Sep. 6, 2001, hereby incorporated by reference.

BACKGROUND OF THE INVENTION

The invention relates to the detection, enumeration, and identification of replicating cells, especially microbial cells (e.g., bacteria, yeasts, and molds), in medical, industrial, and environmental samples. Microbial culture is the predominant methodology in these markets, because of its many attractive features. The invention addresses the chief drawback of microbial culture—the length of time needed to achieve results—while retaining the beneficial attributes of the method.

Microbial Culture for Detecting and Enumerating Microbes

During the 19th and 20th centuries an understanding emerged concerning the role of bacteria, yeast, and molds in causing infectious diseases and determining the quality of foods and beverages. Early on, a powerful method, microbial culture, was developed for detecting small numbers of microbes. Microbial culture allows simple visual detection of microbes by exploiting their propensity to reproduce in large numbers rapidly. For example, a single bacterial cell, which is much too small to see by eye (about one millionth of a meter), when placed in nutrient broth, can cause the broth to become visibly cloudy in less than 24 hours.

A related microbial culture technique, called microbial enumeration or colony counting, quantifies the number of microbial cells in a sample. The microbial enumeration method, which is based on in situ microbial replication, generally yields one visually detectable "colony" for each microbial cell in the sample. Thus, counting the visible colonies allows microbiologists to determine the number of microbial cells in a sample accurately. To perform microbial enumeration, bacterial cells can be dispersed on the surface of nutrient agar in petri dishes ("agar plates") and incubated under conditions that permit in situ bacterial replication. The individual, visually undetectable, microbe replicates repeatedly to create a large number of identical daughter microbes at the physical site where the progenitor microbial cell was deposited. The daughter cells remain co-localized (essentially contiguous) with the original cell, so that the cohort of daughter cells (which may grow to tens or hundreds of millions of cells) eventually form a visible colony on the plate.

Electronic methods have been developed for enumerating microbial colonies. Most such methods automate colony counting but do not substantially increase the sensitivity or decrease the time to results compared to traditional enumeration by eye. Colony counters use a variety of optical methods for detecting colonies including detection of intrinsic optical properties of microcolonies (e.g., U.S. Pat. No. 3,493,772; U.S. Pat. No. 3,811,036; U.S. Pat. No. 5,290,701; Arkin, A. P., et al. (1990); Biotechnology (N Y) 8: 746-9) and color changes of pH indicator molecules in the matrix surrounding the colonies (U.S. Pat. No. 5,510,246). Methods that use stains or probes to label the colonies have also been developed and will be discussed below.

Microbial culture is a remarkably successful method, as evidenced by the fact that even after more than a century, the method still dominates medical microbiology and quality control testing in industrial microbiology (e.g., pharmaceutical, food, and beverage manufacturing). The method is inexpensive, relatively simple, and ultra-sensitive. The sensitivity of microbial culture can be seen in the common test for foodborne pathogens in ground beef. A single microscopic bacterial pathogen cell can be detected in 25 grams of ground beef using microbial culture. Another advantage of microbial culture is its ability to detect a large range of microbes of medical and industrial significance.

An advantage of in situ bacterial replication is the ability to generate a pure, or clonal, population of cells (called pure cultures, clones, or colonies). A pure culture is a large collection of identical living cells which descend from the same progenitor cell. Pure cultures are required for methods that identify microbes and for determining antibiotic resistance. Medical microbiology relies heavily on pure cultures, since bacterial pathogens are frequently isolated from non-sterile clinical samples (e.g., feces or wounds) along with non-pathogenic bacteria that are likely to be even more numerous than the pathogenic cell. Isolating pure microbial cultures is also important in industrial microbiology. For example, pharmaceutical and cosmetics manufacturers must test their products for the presence of microbial contaminants. Pure cultures of the contaminating microbes are used for microbial identification, which determines whether a production batch must be discarded and aids in investigating the source of the contamination in the industrial process.

TABLE 1

Microbial enumeration using microbial culture

Advantages ultra-sensitive
quantitative
generates pure cultures
can detect and enumerate many types of microbes in a single test
can selectively grow microbes
only detects replicating cells
inexpensive
simple and easy to perform Disadvantages slow
manual procedures and analysis
not all microbes are culturable The ability to culture microbes selectively is an essential tool for microbial identification and for determining resistance and susceptibility to antimicrobial agents such as antibiotics. Selective culture exploits the fact that different microbes require different growth conditions. These differences arise from the fact that strains of microbes differ in their biochemical makeup because of inherent genetic differences. For example, one type of microbe might be able to grow on nutrient medium containing the sugar sorbitol as the sole source of carbon atoms to fuel its growth, while another type of microbe cannot. Selective growth is important in the food industry. For example, a food sample can be scanned for a particular food pathogen, *Salmonella*, by plating the sample on media that allows *Salmonella* to grow but not other food microbes.

Similarly, selective culture is used to determine which antibiotic is most effective for killing a bacterial strain isolated from the spinal fluid of a child with bacterial meningitis. A pure bacterial culture (derived from a clonal colony from a nutrient agar plate) is used to inoculate growth medium containing various antibiotics at various concentrations. The optimal antibiotic therapy is determined by monitoring the ability of the microbe to grow in the presence of the various antibiotics. Determining antibiotic resistance and susceptibility by selective growth on the surface of solid nutrient agar medium is another common approach. For example, in the Kirby-Bauer method, small filter disks impregnated with different antibiotics are placed on the surface of nutrient agar plates coated with a pure culture of bacteria from a clinical sample. A gradient of antibiotic diffuses radially outward from the filter. Bacteria that are resistant to high levels of the antibiotic grow up to the edge of the filter. However, bacteria that are very sensitive to the antibiotic can not grow unless they are far from the edge of the filter. After incubating the plates (usually for one or two days) a microbiologist determines the level of resistance to an antibiotic by measuring the thickness of the growth-free ring or zone around the filter. A related method, the "E" test (Hardy diagnostics), uses a rectangular strip that is impregnated with a gradient of antibiotic. The level of bacterial resistance is determined by measuring the point on the strip with the highest antibiotic concentration next to which the bacteria continue to replicate.

The most serious drawback of microbial culture is that it is slow—it takes time to generate the number of cells required for visual detection. The long growth period required for microbial culture is a significant problem in both healthcare and industry. For example, because it requires days to culture and identify the microbe causing a patient's blood infection, a patient with a fungal blood infection could die before antifungal therapy is even begun. Some infectious agents, such as the bacterium that causes tuberculosis, generally require weeks to grow in culture. The long time required for detecting *M. tuberculosis* can result in a patient with tuberculosis infecting many others with the highly contagious disease or the costly quarantine of patients who do not have tuberculosis.

In food manufacture, long testing cycles can increase food spoilage or result in moving inadequately tested material through subsequent processing steps. Slow microbial culture also adversely impacts the production of biopharmaceuticals and vaccines. In these applications, the manufacturing process often requires pooling of batches. Because of long microbial culture testing cycles and the need to move material through the manufacturing process, contaminated batches are sometimes not detected until after a batch pooling step. If it is subsequently found that a contaminated batch was combined with uncontaminated batches, the whole pool of combined batches must be discarded.

Other disadvantages of microbial culture, such as tedious manual procedures and inability to culture some microbes, are considered less problematic than the long time required. For example, manual methods for microbial enumeration predominate, even though instruments for automated plating and analysis have been introduced. Most types of microbes found in the environment cannot be grown in the laboratory. However, such microbes are often not harmful to humans or are destroyed in industrial manufacturing processes and are therefore ignored for most applications. However, several important exceptions of critical medical importance include hard or impossible to culture bacteria such as *Chlamydia*, strains of which can cause sexually transmitted disease and pneumonia. Fortunately, alternative culture-independent methods are available in these cases (see below).

Rapid Microbial Culture Enumeration Methods

A number of microbial culture methods for more rapid microbial enumeration have been developed. One rapid microbial culture method deposits bacterial cells on microscope slides coated with nutrient medium. Using microscopic examination, microbial growth can be detected much earlier than with the naked eye, since microscopes can detect microcolonies resulting from a small number of cell divisions. However, this method is not effective for testing large samples containing low numbers of microbial cells, because only a very small volume of sample can be observed in a microscopic field of view. The low sensitivity of microscopic methods generally limits their usefulness to samples containing more than ten thousand bacterial cells per milliliter—these methods are much less sensitive than traditional microbial culture.

The advent of electronic imaging systems has led to the development of numerous automatic "colony counters." Although, most of these counters are designed to aid the user by automating the colony counting process and do not decrease the time to result, some systems have demonstrated the ability to detect colonies before they are large enough to be seen easily by eye. For example, the Colifast Rapid Microcolony Counter (Colifast) can detect small fluorescently labeled colonies of coliform bacteria hours before they can be seen by eye. The Colifast system achieves enhanced detection by using a fluorogenic compound (a substance that is not fluorescent until metabolized by coliform bacteria) included in the nutrient agar media.

A system for rapid enumeration of microbial colonies using bioluminescent labeling has recently been commercialized. The MicroStar system (Millipore) uses the cellular ATP in microcolonies to generate light via the action of applied luciferase enzyme and substrates. The method reduces time to detection substantially. The MicroStar imaging system has also been used in conjunction with labeled probes to identify specific bacteria (Stender, H., et al. J Microbiol Methods 46: 69-75 (2001)). A drawback of the system is that the detection method kills the microbes, precluding isolation of pure cultures from the colonies. The system also requires an expensive image intensifier module.

An instant film-based method for detecting microcolonies containing specific bacteria has been developed by Boston Probes (Perry-O-Keefe, H., et al. Journal of Applied Microbiology 90: 180-9 (2001)). Microbial microcolonies on membranes are labeled using microbe-specific PNA probes tagged with an enzyme capable of generating a chemiluminescent signal. The membranes are then placed on X-ray or instant-film for imaging. The method is limited to scanning for a particular microbe in one experiment. A similar method uses fluorescently labeled PNA probes and an array scanner (Stender, H., et al. Journal of Microbiological Methods 45: 31-9 (2001)). These approaches require substantially more expertise than traditional culture methods.

Rapid Microbial Enumeration without Microbial Culture

The fastest methods for microbial enumeration forgo microbial culture. Medical and industrial microbiologists are generally interested only in enumerating viable microbes—only living microbes are capable of replicating during microbial culture. Therefore, to be most effective, methods that detect individual cells without reliance on cellular replication must distinguish living from dead microbes by using physiological surrogates for cellular replication (e.g., Nebe-von-Caron, G., et al., J Microbiol Methods 42: 97-114., 2000; Mignon-Godefroy, K., et al., Cytometry 27: 336-44, 1997). Cells are stained with dyes that measure a biochemical property that is generally correlated with the ability to replicate (e.g., esterase activity or biochemical respiration). Validating and instituting surrogate methods have been problematic since samples that are known to meet regulatory standards and that are scored as sterile using traditional plate culturing methods often have thousands of cells that score positive for the surrogate biochemical activity.

An example of a system that directly detects viable cells is the ScanRDI system (Chemunex). ScanRDI enumerates microbial cells that are stained with a fluorogenic esterase substrate using laser scanning technology (U.S. Pat. No. 5,663,057; Mignon-Godefroy, K., et al., Cytometry 27: 336-44, 1997). A laser-scanning system (including an optical collection system using photomultiplier tubes (PMTs)) captures an image of the filter and can detect individual labeled cells. The system illuminates and queries a microscopic area (generally 4-14 μm) but scans the beam progressively so as to cover a macroscopic area (e.g., a 25 mm diameter circle). The system is designed to detect cells with intact membranes and active esterase enzyme. There is a correlation between the numbers of such cells and the number of cells that can form colonies on growth medium. However, this approach often results in substantial "overcounting"—i.e., higher numbers of cells than are detected by traditional culture (Costanzo, S., et al. (2002). PDA Journal of Pharmaceutical Science and Technology 56: 206-219). Another disadvantage of the ScanRDI system is that it kills the microbes during the staining process precluding generation of pure cultures from the detected microbes. Finally, laser scanning systems for cellular enumeration are complex and expensive (hundreds of thousands of dollars) making them difficult to justify for routine microbiological applications. Other laser scanning systems have also been commercialized (Miraglia, S., et al., J Biomol Screen 4: 193-204, 1999; Tibbe, A. G., et al., Nat Biotechnol 17: 1210-3, 1999; Kamentsky, L., 2001, *Laser Scanning Cytometry*. In Cytometry, Z. Darzynkiewicz, H. Crissman and J. Robinsnon, eds. Methods in Cell Biology Vol. 63, Part A, 3rd ed, Series Eds. L. Wilson and P. Matsudaira. (San Diego: Academic Press)).

Flow cytometry is another powerful method that can rapidly enumerate microbes without relying on cellular replication (Alvarez-Barrientos, A., et al., Clin Microbiol Rev 13: 167-195, 2000). Individual organisms or particles are forced to flow through a narrow channel, one at a time, past a laser beam. Besides enumeration, information about size/shape and composition is gathered by analyzing the fluorescence emission and light scattering caused by the organisms. Thousands of individual cells or particles can be analyzed per minute. Pathogens can by identified using flow cytometry by binding fluorescently labeled species-specific antibodies or nucleic acid probes to fixed organisms (Alvarez-Barrientos, 2000, supra).

Pathogens can by identified using flow cytometry by binding fluorescently labeled species-specific antibodies or nucleic acid probes to fixed organisms (Alvarez-Barrientos, 2000, supra). Individual cells of one particular type are usually the targets. Flow cytometric methods have been used more extensively for quantitatively detecting particular cell types on the basis of the ability to bind labeled probes, usually either antibodies or nucleic acids. For example, flow cytometry is used to quantify the population sizes of classes of lymphocytes in patients with AIDS. Flow cytometry is a more complex and expensive method than traditional culture. Although faster than traditional culture, flow cytometry does not have a comparable limit of detection to the traditional method. Traditional microbial culture can detect one bacterial cell in 0.1 liter of water, while flow cytometry is most effective when there at levels that are many thousands of times higher than that. Furthermore, microbial targets are often killed by the staining methods used for detection, eliminating the ability to produce pure cultures.

Using microscopic imaging to visualize and enumerate microorganisms directly can be rapid and relatively simple to perform (Amann, R. I., et al., Microbiological Reviews 59: 143-69, 1995). Direct fluorescent assays (DFA) in which a fluorescently labeled antibody reacts with a fixed sample is a common method in clinical diagnostics laboratories. For example, specimens suspected of containing bacterial agents are routinely stained with Gram stain. Similarly, to test for *M. tuberculosis*, samples are subjected to acid fast staining. The drawback of this technique is that it is many thousands of times less sensitive than microbial culture. The low sensitivity is due to the small fields visualized at high magnification. Only at high target cell concentrations are small fields likely to contain a target cell. Thus, for example, reliable identification of bacterial pathogens in sputum using fluorescent in situ hybridization requires titers of about $4 \times 10^5$ cells/ml or more. Clinical samples obtained in common medically significant infections may contain fewer than 100 cells/ml—a concentration that is not nearly high enough to expect to find a cell in a high power microscopic field.

A system that does have the sensitivity to detect single bacterial cells using large area non-magnified imaging has been developed by researchers at Hamamatsu Corporation (Masuko, M., et al., FEMS Microbiol Lett 67: 231-8, 1991; Masuko, M., et al., FEMS Microbiol Lett 65: 287-90, 1991; Yasui, T., et al., Appl Environ Microbiol 63: 4528-33, 1997). Large area imaging of individual microscopic target cells is accomplished using an ultrasensitive photon-counting CCD camera coupled to a fiber optic system, image intensifier, and Image-Processor. A disadvantage of this system is the great expense incurred because of the incorporation of the image intensifier and associated optics. Furthermore, unlike microbial culture methods, the system can not detect any microbe, distinguish between living and dead microbes, or generate pure cultures.

Rapid Microbial Enumeration by Quantifying Molecular Constituents of Cells

Numerous methods for detecting and identifying microbes based on their molecular constituents have been developed in the last half-century. Although some of these methods are substantially faster than microbial culture, none offers all of the features of culture that are critical to microbiologists. For example, although numerous immunoassays for microbes have been commercialized, this technique is not inherently quantitative, is much less sensitive than microbial culture, and is not as powerful as culture for detecting many types of microbes in a single test. Or, as another example, nucleic acid amplification methods can be as sensitive as microbial culture, but they do not distinguish between living and non-living cells and can not deliver pure cultures for antibiotic susceptibility testing. Methods for biochemical analysis (e.g., of fatty acids, nucleic acids, or proteins) using electrophoresis, mass spectroscopy, and chromatography can be powerful for microbial identification, but such methods are usually inappropriate for microbial enumeration and are generally too expensive and complex for routine microbial diagnostics.

Unmet Needs for Microbial Enumeration

In summary, current microbial enumeration testing is dominated by microbial culture. Microbial culture has the important advantages of being simple, ultra-sensitive, inexpensive, and quantitative but has the significant drawback of being slow. The long time required for results has major costs in healthcare and in manufacturing. More rapid methods have been developed, but while improving the time to results, they have sacrificed one or more of the critical advantages of microbial culture.

Thus, there is need for a test that is faster than traditional microbial culture but that retains the key benefits of the traditional method.

SUMMARY OF THE INVENTION

The invention enable efficient, rapid, and sensitive enumeration of living cells by detecting microscopic colonies derived from in situ cell division using large area imaging. Microbial enumeration tests based on the invention address an important problem in clinical and industrial microbiology—the long time needed for detection of traditional tests—while retaining key advantages of the traditional methods based on microbial culture. Embodiments of the invention include non-destructive aseptic methods for detecting cellular microcolonies without labeling reagents. These methods allow for the generation of pure cultures which can be used for microbial identification and determination of antimicrobial resistance.

The invention features a method for detecting living target cells in a sample including the steps of providing living target cells present in the sample in a detection zone including a detection area at a density of less than 100 target cells per mm$^2$ of the detection area, allowing the formation of one or more microcolonies of the target cells by in situ replication; and detecting one or more microcolonies, wherein the replication produces one or more microcolonies; wherein the longest linear dimension of the detection area is greater than 1 mm; within the detection area, the cells are randomly dispersed and immobilized; the detecting detects one or more microcolonies that have a mean measurement of less than 50 microns in at least two orthogonal dimensions; and the cells in the one or more microcolonies remain competent to replicate following the detection step.

The invention further features a method for detecting microcolonies of target cells including the steps of providing target cells in a detection zone, wherein within the detection area, the cells are randomly dispersed and immobilized; allowing the formation of one or more microcolonies of the target cells by in situ replication, wherein at least one of the microcolonies includes fewer than 100 target cells; and detecting one or more naturally occurring optical properties of the one or more microcolonies using less than 5 fold magnification.

The invention also features an instrument for detecting microcolonies of target cells that includes a photoelectric array detector having an optical resolution of less than 20 microns and encircled energy values of greater than 70% per pixel; and an illumination source, wherein the instrument is capable of illuminating and simultaneously imaging a detection area having at least one dimension that is ≧1 cm, and wherein the instrument does not optically magnify more than 5 fold.

Advantages of the Invention

Some advantages of various embodiments of the invention are listed in Table 2.

TABLE 2

| Embodiment | Advantages |
| --- | --- |
| Reagent-less fluorescent detection and enumeration of microcolonies | Minimal changes to accepted practices<br>Faster and lower risk regulatory path<br>Low cost of goods<br>System simplicity |

TABLE 2-continued

| Embodiment | Advantages |
| --- | --- |
| Collection optics optimized for detecting living microcolonies | Enables non-destructive testing (below)<br>Short time-to-detection |
| Non-magnified large area imaging of individual live microcolonies on membranes | Allows ultra-sensitive detection<br>Allows large dynamic range<br>Allows broad range of sample volumes<br>High signal:background ratio at low titers |
| Non-destructive enumeration (i.e., microbes are not killed) | Allows generation of pure cultures<br>Allows microbial identification<br>Allows detection of antimicrobial resistance<br>Allows internal validation (below) |
| Internal comparison with traditional visible colonies | Streamlines demonstration of equivalence to validate methods |
| Imaging live microcolonies in sterile (closed) disposable | Allows multiple reads<br>Minimizes false positives |
| Methods & software uniquely discriminate growing microbes from artifacts | Added detection robustness, specificity<br>Allows detection in complex samples |

The invention's short time needed to achieve results derives from the invention's ability to detect microcolonies containing only a small fraction of the cells that are required by the traditional methods. Since cell replication requires time, detecting small microcolonies using the invention provides results faster than detecting the large visible colonies using traditional enumeration methods. To detect small microcolonies the invention uses a combination of efficient signal generation and signal detection methods.

The ultra-sensitivity—its ability to detect small numbers of microscopic cells in large samples—stems, in part, from the use of large area imaging. For example, the invention can detect microscopic colonies without magnification. This feature allows a large area to be surveyed for microcolonies in a single image. Imaging a large area is a key to the invention's ability to efficiently analyze large sample volumes. For example, the microbial contaminants in a large volume of a sample can be deposited on a membrane using membrane filtration. The invention using large area non-magnified imaging of microcolonies can analyze the entire membrane efficiently. In contrast, using a high magnification microscope to evaluate the microcolonies on the same filter might require thousands of images.

The power to enumerate small numbers of microcolonies in a large area efficiently also comes from the invention's ability to use imaging approaches that compare object signals to local backgrounds. This ability improves the signal to background ratio for samples containing few cells over methods that integrate the total signal and background in a large area.

Assay robustness for samples with few cells is provided by the invention's inherent ability to enumerate growing microcolonies. Thus, the invention can decrease false positives over methods which detect a single integrated signal, such as methods that quantify the presence of biomolecules (e.g., ATP, antigens, or nucleic acids). Any artifact that causes a signal can generate a false positive when using methods that rely solely on integrated signal. Consider a sample that contains 482 microbial cells each of which generate 100 fluorescent units. The result of an integrative method is a single number (48,200 fluorescent units). Artifacts that generate a similar number of fluorescent units, for example, a large fluorescent dust particle may be indistinguishable. The invention, however, can easily distinguish between a single large dust fluorescent dust particle and 482 individual growing microcolonies.

Detecting growing microcolonies is a powerful method for discriminating against false positive signals from inanimate objects and cells incapable of growth under the test conditions. For example, consider a test to detect microbial microcolonies on a membrane lying on solid growth media in a petri dish. In one embodiment of the invention, the detection area is imaged before allowing the microbes in the detection area to grow into microcolonies. If some fluorescent dust particles or autofluorescent mammalian cells are present in the detection area some positive signals will be apparent in this "zero time" image. After incubating the petri dish to allow for microbial replication another image is taken. When the two images are aligned in register, the positive signals that correspond to microcolonies can be distinguished from the false positives since the false positives are present (usually unchanged) in the "zero time" image and the post-incubation image. Only growing microcolonies should appear over time. To confirm the microcolony signals, images can be acquired and compared at multiple time points during the incubation. Only growing microcolonies should increase in signal strength and in size over time.

Tests constructed using the invention can have a large dynamic range compared to tests constructed using methods in the prior art. Thus, for example, a test based on the invention designed can detect from one to $10^6$ microcolonies in a single image. In contrast, traditional microbial enumeration methods work best when about 30 to 150 colonies are deposited on a filter (47 mm diameter). New enumeration methods (e.g., Chemunex's ScanRDI and Millipore's MicroStar) also have limited dynamic ranges.

To achieve efficient signal generation, the invention can exploit either the intrinsic optical properties of the microcolonies (e.g., autofluorescence, reflectance, or light scattering) or various externally applied labeling reagents. The ability to exploit a range of optical properties and labeling methods enables creation of important microbiological tests. For example, using a method that detects a ubiquitous property of microcolonies (e.g., autofluorescence or infrared absorption) is useful for tests that enumerate total microbial content of a sample. Such tests are critical in food processing for determining the likelihood of spoilage and for finished product release testing in pharmaceutical manufacture. One important embodiment of the invention uses a reagent-less system based on detecting cellular autofluorescence to detect small microbial microcolonies. This embodiment provides a simple, non-destructive, aseptic approach to microbial enumeration. To detect specific types of cells, category-specific labeling reagents can be used. For example, a fluorescently labeled antibody that specifically binds to *Listeria monocytogenes* can be used to detect microcolonies derived from cells of this important food pathogen.

Like traditional microbial culture, the invention can exploit the diagnostic power of measuring microbial growth under selective conditions. For example, to determine bacterial resistance to antibiotics bacteria can be grown on growth medium onto which antibiotic disks have been placed. The size of the no-growth zone near the disks determines antibiotic resistance. The invention can be used to detect the size of this zone more rapidly. Similarly, the invention can be used to detect the growth of specific microbes on selective medium rapidly.

Simplifying the obligatory test validation cycle in which a new method is shown to be equivalent to the "gold standard" method is another advantage of the invention that derives from non-destructive enumeration. The invention facilitates equivalence to the "gold standard" culture tests by allowing an internal comparison of the new and old methods. Briefly, after imaging the microcolonies derived from microbes in a sample at an early time point, the samples can be re-incubated incubated for the amount of time required when using traditional visual detection of colonies. In this way an internal comparison can be made between the invention's enumeration of the microcolonies and the enumeration of the same colonies at a later time by the traditional method.

Other features and advantages will be apparent from the following description and the claims.

By target cell is meant a cell that is potentially present in a sample and whose presence is assayed by the invention.

By category of target cells is meant multiple target cells that are considered identical for the purposes of a test constructed using the invention.

Consider a test designed to detect any strain of *E. coli* bacteria. For the purposes of the test, the category "*E. coli*" would thus include any bacterium in the species *E. coli*. Such a test would be designed to detect, without differentiation, any bacterium in the species *E. coli*. Bacteria, and other target cells, that are not *E. coli* would either not be detected in this test, or would be detected and identified as not being members of the group *E. coli*. In contrast, consider a test designed to detect the pathogen *E. coli* O0157:H7, a subgroup of the *E. coli* species. In this case, the subgroup *E. coli* O0157:H7 is a category of target cells. Bacteria in the subgroup, i.e., in the category "*E. coli* O0157:H7", are detected without differentiation. *E. coli* that are not in the *E. coli* O0157:H7 subgroup are not detected by the test and are therefore not in the *E. coli* O157:H7 category.

Categories need not be taxonomically related as in the previous paragraph. For example, a test might be designed to detect the category of bacteria that makes a protein that is required to confer resistance to the antibiotic vancomycin. This protein could be made by bacterial strains that are not closely related, i.e., that are members of disparate species. A vancomycin resistant strain in one species, however, is likely to be very closely related to vancomycin sensitive strains in the same species. The category of bacteria that make the vanA protein (important for achieving vancomycin resistance), for instance, includes vancomycin-resistant bacteria in the genus *Enterococcus* and in the genus *Staphylococcus*, while the majority of enterococci and staphylococci are not included in the category. Thus, in this case, it can be seen that the category encompasses target cells that are considered, for the purposes of the test, to be identical because of a common feature, in this case a molecular component (a category-specific binding site) rather than to a common phylogenetic (genealogical) relationship.

By non-overlapping categories of target cells is meant sets of target cells whose union is the null set. That is, the category of all *E. coli* bacteria, the category of all bacteria in the genus Pseudomonas, and the category of all fungi are non-overlapping categories. That is, no member of any of the categories is a member of any of the other sets.

By the categorical complexity of a test is meant the number of non-overlapping categories that are detected in the test.

By a category-specific binding site is meant a site on a target cell that specifically binds to a category-binding molecule under specific-binding conditions and that distinguishes target cells that are members of a particular category to be identified in a test from target cells that are not members of that category but might also be present in the test sample. That is, the site is present typically on all members of one category, and typically not on any members of non-overlapping categories. Category-specific binding sites specifically bind to category-specific binding molecules.

If a test scans a sample for a category of target cells that constitutes a taxonomic group, a category-specific binding site is one that is present in essentially all members of that taxonomic group, but is not present in essentially all members of other taxonomic groups that might be present in the test sample.

Alternatively, a test might scan a sample for category-specific binding sites that are shared by members of different taxonomic groups. Examples of this type of category-specific binding site include various macromolecules (e.g., DNA) and genes, mRNAs, and proteins that confer antibiotic resistance, confer virulence, or indicate viability. A category-specific binding site is often a part of a larger molecule or complex. For example, a category-specific genomic sequence can be used as a category-specific binding site in a test. Such a category-specific binding site is part of a much larger genome that contains (1) sections that are not category-specific; (2) sections that are category-specific binding sites but for which the test does not scan; and (3) other sections that are distinct category-specific sequences for which the test does scan.

Binding sites that are present, e.g., in 80%, 90%, 95%, or more than 99% of the target cells that are members of a category but that are absent, e.g., in 80%, 90%, 95%, or more than 99% of the target cells that are members of all other categories of the same class, are considered category-specific binding sites. Note that a category-specific binding site can be trivially or exceptionally absent from a target cell that is a member of the category. Similarly, a category-specific binding site can be trivially or exceptionally present in a target cell that is not a member of a category. For example, consider a protein site that occurs in essentially all E. coli bacteria but in no other bacterial species. If, as might be the case in less than one cell out of millions of bacteria, a mutation causes the protein not to be produced, the marker will not be present in that strain of E. coli. However, this protein site is still considered a category-specific binding site. Alternatively, the gene for the same protein is transferred to a strain of a different species of bacteria by recombinant DNA technology or by natural means (e.g., by viral transduction). In this case, a bacterial strain that is not a member of the category E. coli would express what would still be considered an E. coli-specific binding site.

By category-binding molecule is meant a molecule or molecular complex that specifically binds to a category-specific binding site. Examples of category-binding molecules are nucleic acid probes that hybridize to genomic DNA; nucleic acid aptamers that have been selected or "evolved" in vitro to bind specifically to sites on proteins; antibodies that bind to cellular antigens or serum proteins; and ligands such as epidermal growth factor or biotin that bind specifically to hormone receptors or to binding molecules, such as avidin. Two category-binding molecules are said to be distinct if they bind to distinct and non-overlapping category-specific binding sites. Category-binding molecules may be referred to according to their molecular composition, e.g., a category binding oligonucleotide, probe, antibody, ligand, etc.

By a category-binding molecule that specifically binds to a category of target cells is meant a category-binding molecule that binds under defined binding conditions to essentially all target cells that are members of a category scanned for by a test, but to essentially no target cells that are not members of the category but that are likely to be present in the sample. The number of category-binding molecules that are bound by target cells in a category scanned for as compared to the number bound by target cells(not in such a category, are typically two-fold, five-fold, ten-fold, or greater than fifty-fold greater.

By binding conditions is meant the conditions used in a test to achieve specific binding of category-binding molecules to category-specific binding sites. For example, when the category-binding molecules are category-specific DNA probes, the binding conditions for a particular test might be stringent DNA hybridization conditions. The appropriate stringent DNA hybridization conditions depend on the nature of the probes, as is well known by those familiar with the art. For example, for typical DNA probes of length greater than 500 bases, an appropriate binding condition (usually referred to as a "washing condition" in the hybridization vernacular) is 65° C. at 0.2×SSC. For binding an antibody to an antigen, typical binding conditions are room temperature in PBS-TB.

By a family of category-binding molecules is meant a set of category-binding molecules that specifically bind to a particular category of target cells.

Polyclonal antibodies generally constitute families of category-binding molecules since they generally comprise multiple distinct category-binding molecules that bind to the same category of target cell. Note that, unless affinity purification is used, polyclonal antibody preparations typically also contain antibodies that do not bind to the chosen category of target cell and may contain antibodies that bind to other categories. Additional antibodies are present because the antibody repertoire of an animal is determined by the animal's infection history. Therefore, polyclonal antibodies are preferably purified by affinity methods. Category-binding molecules in a family might bind to some target cells in the category but not to others.

Another example of a family of category-binding molecules is a set of 80 category-specific genomic DNA sequences that occur in all E. coli O157:H7 strains but that do not occur in members of other groups of bacteria. This family of category-binding molecules can hybridize as a group to suitably prepared E. coli O157:H7 cells, but does not hybridize to other categories of cells. Families can include different types of category-binding molecules. For example, a monoclonal antibody that specifically binds to the O157 antigen and one that binds to the intimin protein (a virulence factor) could also be included in the above family of category-binding molecules. A family of category-binding molecules can comprise any number of category-binding molecules (i.e., one or more).

By non-overlapping families of category-binding molecules is meant families of category-binding molecules in which each family binds specifically to one, and only one, category in a set of non-overlapping categories. That is, a set of non-overlapping families of category-binding molecules map to a congruent set of non-overlapping categories. For example, in a test that scans the 4 USP objectionable organisms E. coli, Salmonella, Pseudomonas spp., and Staphylococcus aureus, there are four non-overlapping categories. Such a test might incorporate four different non-cross-reacting polyclonal antibodies, each specific for one of the test categories. Thus, the test comprises four non-overlapping families of category-binding molecules. The non-overlapping families of category-binding molecules in a test are called an ensemble of category-binding molecules.

By an ensemble of category-binding molecules is meant a set of one or more non-overlapping families of category-binding molecules that are combined in a mixture for a particular test. Tests that scan for multiple non-overlapping categories of target cells comprise one family of category-binding molecules per category. The entire set of category-binding molecules, that comprise these families, is referred to as an ensemble.

By the category-binding molecule complexity of an ensemble is meant the number of distinct category-binding molecules or moieties in an ensemble. For example, if an ensemble of category-binding molecules consisted of 234 oligonucleotide probes, the category-binding molecule complexity of the ensemble would be 234.

By the family complexity of an ensemble is meant the number of non-overlapping families of category-binding molecules in an ensemble. The family complexity is the same as the minimum number of target cells required to bind a category-binding molecule from each of the families in an ensemble. The family complexity of a test corresponds to the categorical complexity of a test—i.e., the number of distinct categories for which the sample is scanned. In general, the family complexity also corresponds to the number of distinct signal signatures used in a test.

By signal element is meant a molecule or particle that directly generates a detectable signal. The phrase "directly generates" refers to the fact that signal elements are the immediate source or critical modulator of the detectable signal. Thus, if the signal is photons that arise from a fluorophore, the fluorophore is the immediate source of the photons and, therefore, is a signal element. If the signal is photons scattered by an RLS particle, the RLS particle is a signal element. Alternatively, if the signal is the light transmitted or scattered from a chromogenic precipitated product of the enzyme horseradish peroxidase, the chromogenic product is the signal element.

A characteristic of a signal element is that such an element cannot be divided into parts such that each part generates a signal that is comparable (in character, not necessarily in intensity) to the whole. Thus, a 2 nM diameter quantum dot is a signal element, as dividing it changes the character (emission spectrum) of the resulting nanocrystals. A 5 µm particle impregnated with a fluorescent dye such as fluorescein, is not a signaling element, since it could be divided into parts such that each part has signaling characteristics comparable to the intact particle. The molecule fluorescein, in contrast, is a signaling element. The detectable products of signal generating enzymes (e.g., luciferase, alkaline phosphatase, horseradish peroxidase) are also considered signal elements. Such signal elements (or their precursors when there is a chemical conversion of a precursor to a signal element) may be diffusible substances, insoluble products, and/or unstable intermediates. For example, the enzyme alkaline phosphatase converts the chemiluminescent substrate CDP-Star (NEN; catalog number NEL-601) to an activated product, which is a photon-emitting signal element.

By signaling moiety is meant a molecule, particle, or substance comprising or producing (in the case of enzymes) one or more signal elements and that is or can be conjugated to a category-binding molecule. The signaling moiety can be attached to the category-binding molecule either covalently or non-covalently and either directly or indirectly (e.g., via one or more adaptor or "chemical linker" moieties). Examples of signaling moieties include carboxylated quantum dots; a fluorophore such as Texas Red that is modified for binding to a nucleic acid probe or an antibody probe; streptavidin-coated fluorescent polystyrene particles (which can be conjugated to biotinylated category-specific binding proteins); a rolling-circle replication product containing repeated nucleic acid sequences each of which can hybridized to several oligonucleotides tailed with fluorescently modified nucleotides and which contains a category-specific binding oligonucleotide at the 5' end. A signaling moiety can comprise physically distinct elements. For example, in some cases the signaling moiety is an enzyme (e.g., alkaline phosphatase) that is conjugated to a category-binding molecule (an antibody, for example). Signal is generated when a substrate of alkaline phosphatase (e.g., CDP-Star, or BM purple from NEN and Roche, respectively) is converted to products that are signal elements (e.g., an unstable intermediate that emits a photon, or a precipitable chromogenic product). It is not unusual for the category-binding molecules, enzymatic signaling moieties, and substrate to be applied to the reaction at distinct times.

By signaling moiety complex is meant a physical cell that comprises more than one signaling moiety and more than one category-binding molecule. The physical association of the signaling moieties and category-binding molecules in a signaling moiety complex must be stable (e.g., the signaling moieties and category-binding molecules should have mean half-lives of association with the complex of at least one day in PBS at 4° C.). As an example of a signaling moiety complex, consider a polystyrene microparticle that is coated with thousands of molecules of two types: a target cell-specific antibody and alkaline phosphatase. Such a signaling moiety complex binds to the target cell via the conjugated antibody category-binding molecule. When incubated with a chromogenic alkaline phosphatase substrate (the signal element; e.g., BM purple, Roche), a colored spot can be generated that can be detected by eye. Alternatively, the same signaling moiety complex, when incubated with either a chemiluminescent or a fluorescent alkaline phosphatase substrate, generates either a chemiluminescent or fluorescent signal. Further examples of signaling moiety complexes include: nanogold particles conjugated to fluorescein-labeled antibodies, and latex particles conjugated to both oligonucleotide category-binding molecules and acridinium esters that chemiluminesce upon addition of hydrogen peroxide.

By signal character of a signal element or signal moiety is meant the aspect or aspects of a signal generated by the signal element signaling moiety that is useful for distinguishing it from other signal elements or signaling moieties. For example, the signal character of a signaling moiety labeled with fluorescein and rhodamine is fluorescence. The character of a radio transponder is radio frequency. Examples of photonic signaling character are fluorescence, light scattering, phosphorescence, reflectance, absorbance, chemiluminescence, and bioluminescence. All but the latter two examples of photonic signaling character depend on external illumination (e.g., a white light source, a laser light source, or daylight). In contrast, chemiluminescence and bioluminescence are signaling characters that are independent of external light sources.

By the class of a signal element or signaling moiety is meant the distinct quality of the signal that is useful for distinguishing it from other signal elements or signaling moieties. For example, a liposome that is labeled with red dye is distinguished from differently colored liposomes. The color red is its class. For a micro-transmitter that broadcasts a particular radio-frequency signal, the quality of the radio-frequency signal that differentiates the micro-transmitter from other micro-transmitters constitutes the signal element class.

By signal signature is meant the distinctive signaling quality of the combination of signaling moieties that bind to a category of target cells in a test. A target cell that is bound to four types of antibodies, one of which is conjugated to a fluorescein molecule, and three of which are conjugated with rhodamine molecules has a signal signature that is described by the combined weighted absorbance and emission spectra of fluorescein and rhodamine.

By signal complexity of a test or an ensemble of labeled category-binding molecules is meant the number of categories of target cells that can be distinctly labeled in the test or by binding to the ensemble. Alternatively, the signal complexity is defined as the number of distinct signal signatures that would be expected to occur if a member of each category of target cell were present. For some tests, the signal complexity of an ensemble of category-binding molecules is the same as the number of categories for which the test scans. Other tests, which scan for many categories, may only have a signal complexity of one.

By selection force is meant a force that is used to capture, isolate, move, or sequester target cells. Examples of selection forces include gravity, magnetism, electrical potential, centrifugal force, centripetal force, buoyant density, and pressure. Target cells can be mobilized by a selection force acting on the target cell alone. Alternatively, selection forces can act specifically on target cells that are associated with selection moieties (see definition below).

Examples of the application of selection forces to mobilize target cells include: centrifugation of target cells; magnetic selection of target cells bound to magnetic particles; gravitational sedimentation of target cells labeled with metallic particles; and deposition of target cells on a porous membrane by vacuum filtration.

By selection moiety is meant an atom, molecule, particle, or cell that can be conjugated to a category-binding molecule and that confers on the category-binding molecule the ability to be selectively captured, isolated, moved, or sequestered by a selection force. When a category-binding molecule:selective moiety complex is specifically bound to a target cell, the target cell can also generally be selectively captured, isolated, moved, or sequestered by the selection force. Selective refers to the preferential conferring of susceptibility to mobilization by the selection force on selection moieties and associated cells over cells not associated with selection moieties.

Paramagnetic particles and ferritin are examples of selection moieties. A dense silica particle that sinks in solution is another type of selection moiety. Such particles, when coated with category-binding molecules and bound to a microbial target cell will cause the target cell to sink in aqueous solution, thus enabling separation of the bound target cell from other sample unbound constituents.

By selective character is meant the aspect or aspects of a selection moiety that is useful for capturing, selecting, or moving the selection moiety. For example, the selective character of a paramagnetic particle is magnetism. The selective character of a silica particle that rapidly sinks in aqueous solution is mass.

By a roughly planar surface or substrate is meant a surface that can be aligned in parallel to an imaginary plane such that when the distance is measured from points in any 1 mm×1 mm square on the surface to the closest points on the imaginary plane, the absolute value of the mean distance is less than 50 micrometers.

By detection surface is meant the surface of a roughly planar substrate onto which target cells are deposited. In embodiments using photonic signaling character, if the detection surface is optically transparent, detection can be effected via either face of the detection surface. If the detection surface is opaque, detection is effected via the face of the detection surface on which the target cells are deposited.

By detection area is meant the area of the detection surface that is simultaneously sampled by a detection device. For example, the section of a glass slide that is simultaneously imaged by an optical device that includes a collection lens and a CCD chip might measure 0.8 cm×0.5 cm. The detection area is then 0.4 cm$^2$.

By detection zone is meant the volume in which replicating target cells can be detected by the detection device. The detection zone has the same dimensions as the detection area but has a depth corresponding to the depth in which the signal from replicating target cells can be detected and identified. The depth of the detection zone is therefore dependent on the threshold criteria used to score for positive signal. When optical detection is used, the depth of the detection zone is dependent on the optical depth of field.

By the longest dimension of a detection area is meant the line of maximum length that can be drawn between two points on the perimeter of the detection area. For example, if the detection area is a rectangle measuring 0.3 cm×0.4 cm, the longest dimension of the detection area is the diagonal, 0.5 cm. If the detection area is an ellipse with semi-major axis of length 7 mm and semi-minor axis of length 2.5 mm, the longest dimension of the detection area is 14 mm.

By large area detection or large area imaging is meant a method for detecting microscopic target cells in which the detection area (the area that is simultaneously analyzed by the detection device) is much larger than the dimensions of the target cells or microcolonies. The detection area for large area detection has at least one linear dimension that is $\geq$1 mm. In contrast, the microscopic colonies are substantially smaller, typically measuring less than 50 µm in at least two orthogonal dimensions. Examples of large area detection include imaging a 9 mm diameter detection area with a CCD camera; imaging a 2 cm×1 cm rectangle by scanning with a linear array detector that has a long dimension of 1 cm; and imaging a 4 cm×4 cm filter using direct exposure on photographic film.

Some technologies scan samples for microcolonies but do not exploit large area detection. Examples include solid phase laser microbeam scanning cytometry and microscopic examination of multiple high power microscopic fields on a slide.

By conjugated or stably associated is meant a physical association between two entities in which the mean half-life of association is least one day in PBS at 4° C. Consider, for example, the complex case of passive protein adsorption to polystyrene particles. There are several different classes of adsorbed proteins. Some proteins are stably associated to the surface with half-lives of many months. Other proteins, such as those that are loosely bound on the outer layer of adsorbed protein, may not be stably associated with the particles and can leach out within hours.

By particle is meant a rigid matrix (i.e., with at least some characteristics of a solid), which measures less than one millimeter along any axis. Particles can be doped with or conjugated to signal elements. Particles are often referred to as particles or with terms that reflect their dimensions or geometries. For example, the terms nanosphere, nanoparticle, or nanobead are used to refer to particles that measures less than 1 micron along any given axis. Similarly, the terms microsphere, microparticle, or microbead are used to refer to particles that measure less than one millimeter along any given axis. Examples of particles include latex particles, polyacrylamide particles, magnetite microparticles, ferrofluids (magnetic nanoparticles), quantum dots, etc.

By image intensifier or image tube is meant a device that amplifies a photonic signal, as defined in the glossary of Inoué, Shinya, et al., Video microscopy: the fundamentals (Plenum Press, New York, 1997; p. 665): "A device coupled (by fiber optics or lenses) to a video camera tube to increase sensitivity. The intensifier is a vacuum tube with a photocathode on the front end that emits electrons according to the image focused upon it, an electron lens and/or microchannel plate(s) that focuses the electrons onto a phosphor at the back end, and a high voltage accelerator that increases the energy of the electrons. Can be single or multiple stage." A variety of such image intensifiers is described in detail in Chapter 8 of the same reference.

By simultaneous detection in a section of the detection area is meant detection of the signal from a section of a roughly planar detection surface in one step. Large area imaging of targets in a detection area using a CCD chip, visual detection, or photodiode-based signal integration are examples of simultaneous detection.

By identification is meant determining the category or categories of which a target cell is a member.

By sample is meant material that is scanned by the invention for the presence of target cells.

By direct visual detection is meant visual detection without the aid of instrumentation other than wearable corrective lenses.

By photoelectric detector is meant a man-made device or instrument that transduces photonic signals into electric signals. Examples of photoelectric detectors include CCD detectors, photomultiplier tube detectors, and photodiode detectors, e.g., avalanche photodiodes.

By encircled energy or ensquared energy is meant the percentage of photons from an infinitely small light source that are captured on a pixel of a photodector array.

By thermal radiation is meant black body radiation.

By cellular autofluorescence or autofluorescence is meant the fluorescence exhibited by cells due to the fluorescence of natural intrinsic cellular constituents, such as NADH and oxidized flavoproteins. Cells expressing fluorescence due to recombinant fluorescent proteins such as green fluorescent protein are not considered to be autofluorescent.

By in situ replication is meant the replication of a target cell in place, so that the daughter cells remain essentially co-localized with the progenitor target cell. For example, in in vitro biological culturing of bacteria on nutrient agar plates, single dispersed bacteria are deposited on a plate and incubated under conditions that permit bacterial replication. A bacterium in a certain location replicates giving rise to progeny cells that also replicate. All of the cells remain co-localized (essentially contiguous) with the original cell, eventually giving rise to a visible colony on the plate. Where there was formerly a single cell, there is now a colony of more than $10^7$ cells.

By a microcolony of target cells is meant a set of target cells that lie in close physical proximity to each other, that lie on (or are anchored to) a surface, and that are the clonal descendants via in situ in vitro replication-based amplification of a single ancestral target cell. A microcolony is generally too small to be visible by the naked eye (e.g., less than 50 microns in diameter).

Any type of dividing target cell can give rise to microcolonies in situations that lead to physical co-localization of the clonal descendents of the target cells. For example, microcolonies could contain animal or plant cells, fungi, or bacteria.

By illuminating is meant irradiating with electromagnetic radiation. Electromagnetic radiation of various wavelengths can be used to illuminate. It includes, for example, radiation with wavelengths in the X-ray, UV, visible, or infrared regions of the spectrum. Note that illuminating radiation is not necessarily in the visible range.

By signal elements or signaling moieties with photonic signaling character is meant signal elements or signaling moieties that are detectable through the emission, reflection, scattering, refraction, absorption, capture, or redirection of photons, or any other modulation or combination of photon behavior. Some examples of signal elements or signaling moieties that have photonic signaling character include: the fluorophore Texas Red (fluorescent signaling character); CDP-Star (chemiluminescent signaling character); luciferase (bioluminescent signaling character); resonance light scattering particles (light scattering signaling character); BM purple (light absorption or chromogenic signaling character); and up-converting phosphors (absorption of two long wavelength photons and emission of one shorter wavelength photon).

By 'number' X 'solution name' is meant an aqueous solution comprising the constituents of solution name at number times the concentration of the solution (except for water). For example, 10×EE contains 10 mM EDTA/100 mM EPPS (EE, or 1×EE, contains 1 mM EDTA/10 mM EPPS).

EE is a solution that is 1 mM EDTA/10 mM EPPS. Before mixing them together, the conjugate acids of both components are brought to pH 8.0 with NaOH PB is 0.1 M sodium phosphate buffer pH 7.4.

PBS is a phosphate-buffered saline solution containing: 120 mM NaCl, 2.7 mM KCl and 10 mM phosphate buffer (sodium salt) pH 7.4.

PBS-B is 0.1% BSA (IgG Free; Sigma Cat. No. A-7638) in PBS.

PBS-T is 0.05% Triton X-100 (Sigma Cat. No. X-100) in PBS

PBS-TB is PBS/0.1%BSA/0.05% Triton X-100

PBT is PBS/0.1% BSA (IgG Free; Sigma Cat. No. A-7638)/.05% Tween-20 (Sigma Cat. No X-100)

LB is Luria Broth for growing bacteria and is made as described previously (Ausubel 1987, supra).

SSC is 150 mM NaCl/15 mM $Na_3$ citrate adjusted to pH 7.0 with HCl.

EDAC is (1-Ethyl-3-(3-dimethylaminopropyl)) carbodiimide.

TSA is Tryptic Soy Agar (Becton Dickinson/Difco; cat. num. 236950).

TSB is Bacto™ Tryptic Soy Broth (Becton Dickinson cat. num. 211822).

AP is alkaline phosphatase.

BSA is Bovine Serum Albumin.

CCD is charged coupled device.

Cfu is Colony forming unit (a measure of bacterial concentration that corresponds to the number of viable bacterial cells).

FITC is fluorescein isothiocyanate.

PNA is peptide nucleic acid.

Unless otherwise noted, microbiological strains described in the specifications are obtained from the American Type Culture Collection (ATCC), Manassas, Va.

BRIEF DESCRIPTION OF THE DRAWINGS

FIG. 1. Traditional microbial culture requires many generations of cell division.

Figure 19:
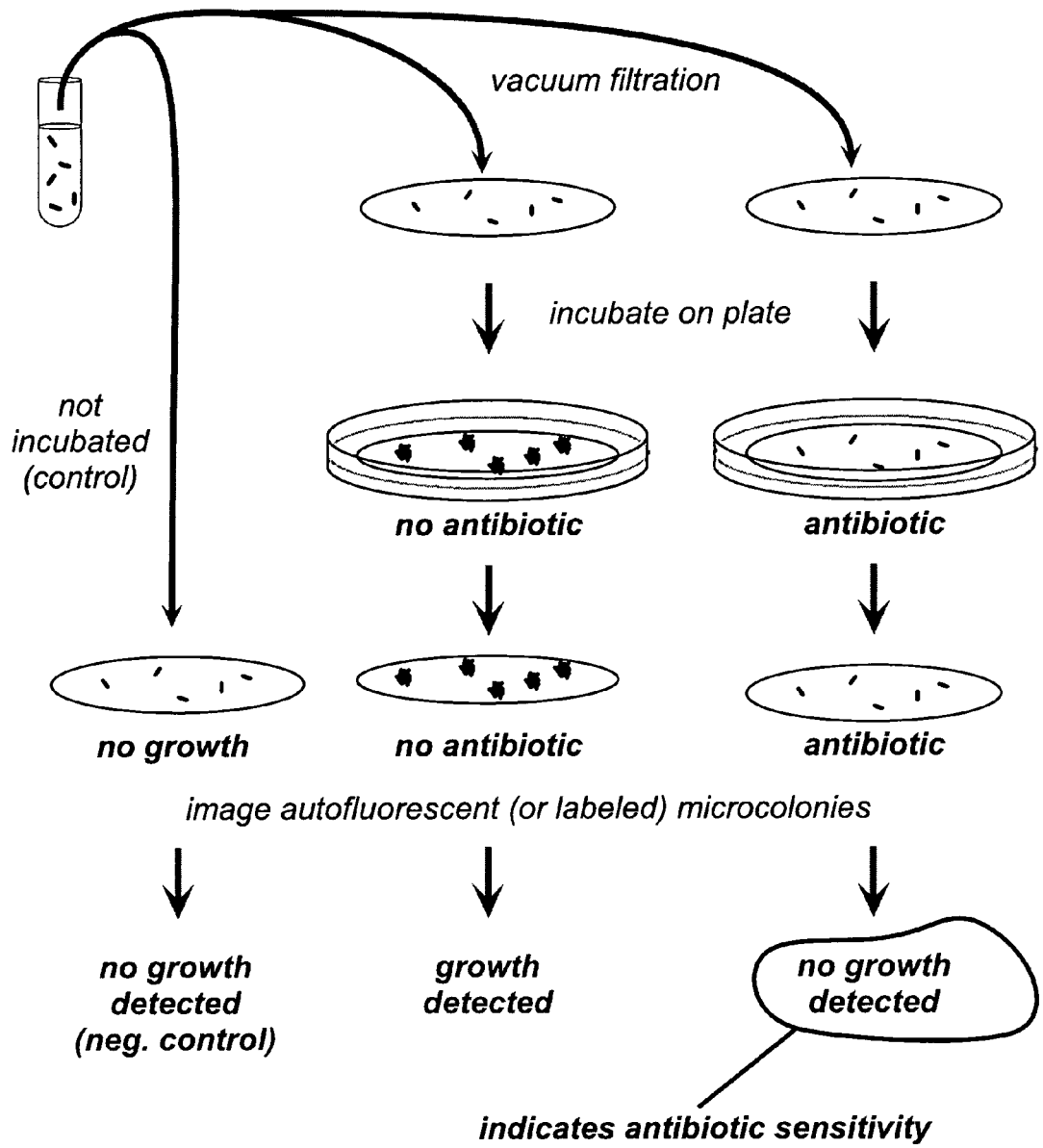

The long time-to-results of traditional microbial culture results from the time required to generate enough microscopic target cells to be visible to the naked eye.

FIG. 2. The concept for rapid detection of microbial growth by detecting microcolonies The invention achieves rapid enumeration of growing cells by imaging microcolonies containing fewer cells than do the macrocolonies that are detected by eye using the traditional method. The invention is faster because fewer generations are required than for the traditional method FIG. 3. Scheme for a CCD imaging device for large area imaging The CCD-based imager depicted in the schematic figure was used to collect much of the data described in the examples (see also Step 5 of Detailed Description section). In one example, excitation light is provided by introducing light from a high intensity white light source (1000 Watt Xenon arc lamp, Model A-6000, Photon Technology Incorporated, Monmouth Junction, N.J.) into a liquid light-guide (5 mm core diameter, Model 380, Photon Technology Incorporated, Monmouth Junction, N.J.). The liquid light-guide carries the light to an excitation filter-wheel (BioPoint FW, Ludl Electronics, Hawthorne, N.Y.) and directs the filtered beam (typically 9 mm in diameter) onto the detection surface containing the labeled target cells. The detection surface is the optically clear bottom of a microtiter dish well. However, the same apparatus can detect labeled target cells on various detection surfaces (e.g., microscope slides, coverslips, and tubes with flat, optically clear, bottoms). The incident light strikes the detection surface inducing fluorescence in the signaling moieties that are bound to target cells via category-binding molecules and that are deposited on the optically clear surface. A portion of the emitted fluorescent light is collected by a high-collection efficiency lens system and transmitted through an emission filter-wheel (BioPoint FW, Ludl Electronics) to a CCD Camera (Orca II, Hamamatsu, Bridgewater, N.J.).

FIG. 4. Scheme of a CCD imaging system for non-magnified large area imaging

The figure shows a CCD imager with an angular illumination configuration in which light is introduced onto the detection surface (shown here as the bottom of a well of a microtiter plate) at an angle from the side of the collection optics. The angle is chosen to optimize collection efficiency and to avoid obstruction of the incident beam by the collection lens. The advantage of this configuration is that reflections from the bottom surface of the sample holder are not collected by the collection lens and therefore do not contribute to the fluorescence background noise.

FIG. 5. Scheme for regent-less detection of microcolonies using non-magnified large area imaging.

The figure diagrams a rapid method for enumerating bacterial growth without using a labeling reagent. The intrinsic autofluorescence of target cells in microcolonies is detected using CCD-based non-magnified large area imaging. Advantages of this reagent-less approach include its simplicity, non-destructiveness, and broad applicability. Alternatively, labeling reagents that bind to target cell-specific binding sites (e.g., fluorescent antibodies or nucleic acid probes) can be used for detecting microcolonies containing target cells.

FIG. 6. Results of detection and identification of bacterial microcolonies using non-magnified large area imaging (Example 1)

The figure shows a rapid, simple, and sensitive method for detecting microcolonies by imaging labeled microcolonies using CCD-based non-magnified large area imaging. In this example, single cells were allowed to go through several replicative generations in order to form microcolonies. The microcolonies were labeled with either Syber Green I or a FITC-labeled antibody. In FIG. 7 the upper row of panels shows the 0 hour time point containing single cells. The lower row of panels shows microcolonies after 3 hours of incubation. There is a substantial increase in size and signal of the objects detected by CCD imaging over time due to the increase in the number of cells at the sites where the colony-forming cells were originally deposited.

FIG. 7. Results of autofluorescence based detection of bacterial microcolonies using non-magnified large area imaging (Example 2)

The figure diagrams a rapid, simple, and sensitive method for detecting microcolonies by imaging cellular autofluorescent signals using CCD-based non-magnified large area imaging. Single dispersed cells were deposited on a filter, which was incubated on growth medium for 5.25 hours at 37° C. Microcolonies (resulting from the clonal growth of the single dispersed cells) generated substantial autofluorescent signal (left panel) when compared to a filter on which no bacteria were deposited (right panel) but that was otherwise prepared and imaged identically.

FIG. 8. Results of a simple method for validating a rapid reagent-less microbial enumeration test using an internal comparison to the traditional culture method (Example 3)

The figure demonstrates a simple method for showing the equivalence of microcolony enumeration to the traditional method. Using non-destructive detection of microcolony autofluorescence allows the microcolonies detected by the invention to be re-incubated until they mature into the macrocolonies that are detected using traditional visible colony counting. Note that the pattern of spots formed by the microcolonies (left panel) matches the pattern formed by the visible colonies (right panel) indicating the equivalence of the two methods.

FIG. 9. Scheme of a method for showing the accuracy and limit of detection of autofluorescent microcolony detection using non-magnified large area imaging (Example 4)

The figure shows the method used to measure the accuracy of the invention when the samples contain extremely low levels of target cells. For each of the 101 filters, the result obtained by scoring the autofluorescent microcolonies was the same as the result obtained by the traditional method.

FIG. 10. Results of an experiment to determine the number of microbial cells in autofluorescent bacterial microcolonies rapidly detected using reagent-less non-magnified imaging (Example 5)

The figure shows the signal generated from microcolonies of *E. coil* using large area imaging from *Escherichia coli* microcolonies (top panel). The three microcolonies imaged with high powered microscopy in the bottom panels correspond to the three microcolonies imaged using the invention in the upper panel. The number of bacteria in each microcolony is indicated below each frame (45, 48 and 50 cells). The figure demonstrates that microcolonies containing low numbers of *E. coli* cells can be detected using reagent-less non-magnified large area imaging.

FIG. 11. Results of CCD-based, non-magnified, large area imaging detection and identification of bacterial microcolonies in an environmental water sample (Example 6)

The figure shows the analysis of bacterial growth by using the invention to detect bacterial colonies in water from the Charles River. Bacterial cells were collected onto mixed cellulose ester filters. The filters were placed onto an R2A agar plate, and incubated for 74 hours at 32.5° C. At various time points the filters were imaged using reflectance of white light and autofluorescence. Macrocolonies that were 0.55 mm or greater in diameter were identified and counted in the reflectance images. The time points at which autofluorescent microcolonies that gave rise to a macrocolonies could be detected was also determined. At various time points the percentage of the 74 hr macrocolonies that were detectable as autofluorescent microcolonies was plotted.

FIG. 12. Graph showing correlation between CCD-based, non-magnified, large area imaging detection of bacterial microcolonies and a classical pour plate culture method for enumerating bacteria in a sample (Example 7)

The figure compares the enumeration of autofluorescent microcolonies obtained using the invention and the traditional pour plate method of microbial culture.

FIG. 13. Results showing dynamic range and linearity of a reagent-less enumeration test (Example 8)

The figure shows the analysis of dynamic range and linearity by using the invention to detect autofluorescent microcolonies.

FIG. 14. Results of antimicrobial preservative effectiveness testing without sample dilutions (Example 9)

The figure shows that comparable antimicrobial preservative effectiveness results are obtained using invention and traditional methods. The comparison shows the potential of the invention to eliminate most of the labor and expense of this test by obviating the need to analyze hundreds of sample dilutions.

FIG. 15. Results of autofluorescence-based detection a heat-stressed biological using non-magnified large area imaging (Example 10)

The figure shows the correlation between enumeration of heat-stressed biological indicator cells using the invention and the traditional pour plate method. The biological indicator G. stearothermophilus was subjected to a variety of heat stress regimes. Microcolony autofluorescence was measured using CCD-based large area imaging and visible macrocolonies were counted visually. The results of the two methods are plotted against each other and show good correlation. The invention, however, required substantially fewer dilutions than did the traditional method.

FIG. 16. Autofluorescence based Results of autofluorescence-based detection of bacterial microcolonies in ground beef (Example 11)

The figure shows the detection times of autofluorescent microcolonies and macrocolonies derived from microbes in ground beef. Tracking the appearance over time of microcolonies that gave rise to the 48 hr macrocolonies showed that 100% of the macrocolonies were detected by the invention at 16 hrs. This shows the potential of the invention to reduce the time required to achieve results significantly compared to traditional methods.

FIG. 17. Scheme for magnetic selection followed by microcolony detection (Example 12)

A scheme is shown for magnetic selection of target cells followed by in situ growth and detection of microcolony autofluorescence using the invention.

FIG. 18. Results of detection of bacteria in a complex sample with non-specific magnetic selection followed by microcolony detection using non-magnified large area imaging (Example 12)

The figure shows results of an experiment in which S. aureus bacteria were magnetically captured from whole blood. The bacteria were selected from a blood sample using magnetic particles coated with a mixture of broadly reactive agents that bind bacteria. After filtration, plating, and incubation (6 hr), the autofluorescent microcolonies were detected using non-magnified large area imaging. The filters were allowed to incubate overnight. Afterwards, the filters were again imaged (images not shown) and the position of six hour microcolonies were verified to have grown into macrocolonies, eliminating the chance that the microcolonies would have been mistaken for dust or other particulates.

FIG. 19. Scheme for rapid antimicrobial susceptibility testing (Example 13)

The figure diagrams a rapid method for testing the sensitivity of a bacterial strain to an antibiotic by detecting the appearance of microcolonies using CCD-based non-magnified large area imaging. For the strain of bacteria shown, microcolonies cannot form when the bacteria are grown in the presence of the antibiotic (right column) indicating sensitivity to the antibiotic. Bacteria also do not grow without incubation under growth conditions (left column). As expected, growth is detected when the strain is incubated under growth conditions in the absence of the antibiotic (center column).

FIG. 20. Results of rapid antimicrobial susceptibility testing (Example 13)

The figure shows the results of an antimicrobial susceptibility test that compares the growth of bacterial strains (one sensitive to and one resistant to the antibiotic tetracycline) as microcolonies on agar plates containing the antibiotic. Bacterial cells from each strain were filtered onto a polycarbonate membrane, placed onto LB agar plates containing tetracycline, and then incubated for three hours at 37° C. (columns labeled "3 hour"). Other filters prepared similarly were placed on LB agar plates containing tetracycline for less than 5 minutes at room temperature (panel columns labeled "0 hour"). The filters were fixed and stained with a nucleic acid stain. CCD imaging of the membranes containing bacteria that were incubated for three hours (column labeled: "3 hour CCD") detected microcolony growth on the membranes that contained the resistant strain but not the sensitive strain. The growth of microcolonies on the filters containing the resistant but not the sensitive strain was confirmed by high power fluorescence microscopy (column labeled: "3 hour microscope"). As expected, no microcolonies were detected on the CCD image of the filters that were not incubated under growth conditions (column labeled: "0 hour CCD") and only single dispersed cells were detected by high power fluorescence microscopy. Computer image analysis was used to quantify the results of CCD imaging of the membranes (bar graph). The membrane containing microcolonies formed by the resistant strain generated about 25-fold more intensity than did the membrane containing the sensitive strain. The results of this experiment show that detecting microcolonies using non-magnified large area imaging is a rapid and sensitive method for antimicrobial susceptibility testing.

FIG. 21. Results of rapid antimicrobial susceptibility testing using the disk diffusion method and non-magnified large area imaging (Example 14)

The figure shows the results of an antimicrobial susceptibility disk diffusion test comparing the growth of bacterial strains (one sensitive and one resistant). Autofluorescent microcolonies, growing on or near the diffusion disk, were detectable after 5 hours of growth, greatly reducing the time to detection from a standard overnight growth. The left panel shows the Tet resistant strain growing close to the diffusion disk, while the right panel shows the lack of growth of the Tet sensitive strain. The disk diffusion plates were allowed to incubate overnight. The 24 hour zones of inhibition were compared to the 5 hour zones. The 24 hour zone of inhibition was the same as the 5 hour microcolony result indicating that the invention can yield faster but comparable results compared to the traditional method.

FIG. 22. Results of rapid Antimicrobial susceptibility testing using the E-test™ and non-magnified large area imaging (Example 15)

The figure shows the results of an antimicrobial susceptibility test comparing the growth of bacterial strains (one sensitive and one resistant) using Etest™ strips containing the antibiotic tetracycline. Bacterial cells were spread on TSA plates. An E-test™ strip was added directly to the plates, which were incubated at 37° C. Autofluorescent microcolonies growing on or near the E-test™ strip were detectable after 5 hours of growth. The left panel shows the resistant strain at 5 hours growing near the 256 µg/ml segment of the strip. The right panel shows the sensitive strain at 5 hours with a zone of inhibition near the 2 µg/ml segment of the strip. The E-Test™ plates were allowed to incubate overnight. The 24 hour zones of inhibition were comparable to the 5 hour zones indicating that the more rapid results obtained with the invention are comparable to the slower traditional method.

DETAILED DESCRIPTION OF THE INVENTION

Overview of the Invention

The invention rapidly and cost-effectively analyzes a minimally processed sample for growing cells. Both the invention and traditional bacterial culture methods measure cell growth by detecting the formation of bacterial "colonies"—clusters of associated cells that arise from single cells via successive cell divisions (FIG. 1). However, the invention detects cell growth more quickly than traditional microbial culture, because it detects microcolonies that appear at an earlier stage than the visually observed macrocolonies detected by traditional microbial culture (FIG. 2, FIG. 8). By using the same method principles as microbial culture the invention can retain the advantages of the traditional method while still improving time to results significantly.

To understand how the invention detects microcolonies it is helpful to examine a specific embodiment and application. For example, consider a test for enumerating the microbes in the water used to manufacture an injectible pharmaceutical. The microbes in a sample of the water (100 ml) are concentrated and immobilized by passing the liquid through a porous membrane. The membrane containing the microbes is placed on nutrient growth medium in a disposable petri dish. The microbes are incubated at 32° C. to allow them to replicate and to form microcolonies. Light is directed at the surface of the membrane causing cells in the microcolonies to autofluoresce. This autofluorescent signal derives from biomolecules that are present in the cells (e.g., NADH and oxidized flavoproteins). The autofluorescing microcolonies are then imaged electronically. Light originating from an individual microcolony strikes a pixel or small cluster of adjacent pixels on a CCD array photodetector. The number of autofluorescing microcolonies is immediately calculated by image processing software and reported to the user. Note that the process is identical to traditional microbial culture, except that the invention detects the results faster and automatically.

Because this embodiment of the invention is non-destructive (i.e., does not kill or injure the microbes), the detected microcolonies can be grown into pure cultures. These pure cultures can be used for microbial identification—and, for clinical samples, for determining antimicrobial resistance and susceptibility. Non-destructive detection also makes it simple to validate the equivalence of the method to traditional microbial enumeration. After detecting the microcolonies using the invention, the petri dish can simply be re-incubated to allow the microcolonies to growth for the length of time required to generate the visible macrocolonies detected by traditional microbial culture detection. Comparing the number and location of microcolonies detected by the invention to the visible colonies derived from further growth of the microcolonies facilitates determining the equivalence of the invention and the traditional method.

The invention can be used to construct tests using a number of formats, labeling methods, category-binding molecules, and detection methods. However, the tests have several key features in common. The steps and processes that are common to many embodiments of the invention are described below.

The General Configuration of Applications of the Invention Includes the Following Steps:
Step 1: Formulating the test question, choosing the sample, categories of cells to be detected, growth conditions, and signaling character
Step 2: Depositing the cellular targets in the detection area
Step 3: Allowing cellular replication to form microcolonies
Step 4: Optional labeling of microcolonies
Step 5: Enumerating the microcolonies Formulating the question to be answered by the test is the first step in creating a new application based on the invention. Some examples of important questions that industrial and clinical microbiologists must address are listed in Table 3. Articulating the test question generally defines the sample type that must be tested (e.g., ground beef, clinical urine sample, or a pharmaceutical finished product). The sample type and volume are important parameters in choosing methods for depositing the target cells in the detection area (see step 2). Articulating the test question also defines the types, or categories, of cells that must be detected in the application (e.g., aerobic bacteria, yeast or molds, pseudomonas, *E. coli* O157:H7, or an anonymous spinal fluid isolate).

TABLE 3

Examples of questions answered by tests based on the invention

Do the numbers of bacteria in a urine sample indicate a urinary tract infection?
Does a patient's blood sample contain viable infectious microbes?
Which antibiotic is best for treating a particular patient with bacterial meningitis?
How many aerobic bacteria are present in 25 g of meat?
Are there any cells of the foodborne pathogen *E. coli* O17:H7 in a sample of ground beef?
How many yeast and mold cells are present in an environmental air sample?
How many Pseudomonas cells are present in 10 g of an over-the-counter pharmaceutical tablet?
Is the finished product batch of injectible drug sterile?
How many yeast cells are present in a production sample of beer?

After defining the type of cells to be detected or enumerated, conditions are chosen for fostering the growth of the cells in the detection area. Important parameters for allowing cellular replication include: composition of the growth medium, presence of selective reagents such as antibiotics, temperature, and the level of oxygen and other gases. If possible, growth conditions are chosen that foster growth of the cells to be detected but that are refractory to the growth of other types of cells. For example, media for detecting yeast and molds often contain ingredients that inhibit the growth of otherwise more rapidly growing bacterial microbes.

A method for generating detectable signal from the cells to be detected must also be chosen. Choosing the signal depends on the type of cells in the microcolonies to be detected, the types of other cells that might form microcolonies, and the type of background expected in the sample. Consider a test for determining the total number of aerobic bacteria in a finished product in pharmaceutical manufacturing; a wash solution for contact lenses, for example. Because a broad spectrum of thousands of environmental microbes could be present in such a sample, the signal generating method must be very general. Some such methods rely on the intrinsic optical properties of the microcolonies, such as microcolony autofluorescence, reflectance, or infrared absorbance. Such methods allow rapid microcolony detection without using a reagent—an important advantage of the invention. Reagentless signal generation using, for example, microcolony autofluorescence, substantially simplifies test methods, allows aseptic sample processing, and enables rapid tests that use the same media and disposables used in "gold standard" methods. Alternatively, microcolonies generated by the target cells can be labeled using stains.

Using Stains and Specific Probes to Enumerate Specific Categories of Target Cells Using stains or probes that bind to molecular constituents of target cells can be used in applications that ask a range of diagnostics questions. Examples of stains that can be used to detect a broad range of target cells (e.g., all aerobic bacteria) include nucleic acid stains (e.g., propidium iodide or Syber Green (Molecular Probes)), and stains for enzyme activity (e.g., fluorogenic esterase stains). To label narrower categories of target cells, labeled probes that bind to target-specific molecular constituents can be used. For example, a fluorescently labeled antibody that binds specifically to a molecule that only occurs on the surface of the food pathogen *E. coli* O157:H7 can be used to detect pathogenic microcolonies in a food sample.

Thus, to detect the presence of a category of target cells, the invention can use molecules that bind specifically to category-specific molecular constituents. The category-specific molecular constituents that occur on target cells are called category-specific binding sites and the molecules that bind specifically to them are called category-binding molecules. To detect the binding of category-binding molecules, a detectable label, or signaling moiety is generally attached to the category-binding molecules. Note that category-specific binding sites are a property of target cells that are potentially present in the sample to be tested. In contrast, category-binding molecules are a reagent provided in a diagnostic test kit.

An advantage of the invention is that a broad spectrum of category-binding molecules can be used. This feature is important since different types of category-binding molecules are used to ask different types of diagnostic questions (e.g., broad kingdom-level screening vs. narrow subspecies-level identification). Classes of category-binding molecules (also sometimes referred to as probes) comprise: nucleic acids (oligonucleotides, aptamers, cloned sequences, genomic DNA, RNA, etc.); chemical variants related to nucleic acids, such as peptide nucleic acids (PNA); antibodies; enzymes (which can bind target substrates); non-enzymatic proteins such as avidin (which binds the target molecule biotin); molecules that bind cellular constituents specifically (e.g., phalloidin which binds actin or biotin which binds avidin); dyes and stains, (e.g., propidium iodide, auramine-rhodamine, or SYTO 17); ligands (e.g., epidermal growth factor, which binds specifically to the epidermal growth factor receptor); and polypeptide or nucleic acid binding reagents that have been selected using in vitro evolution techniques (e.g., Zhang, et al., Nat. Biotech. 18: 71-74, 2000).

Category-binding molecules can incorporate other functional domains or modifications. For example, category-binding molecules are often covalently or non-covalently associated with signaling moieties (i.e., a labeling domain such as a fluorophore or a dyed microparticle) or selection moieties (e.g., magnetic particles or solid surfaces). Alternatively, a category-binding molecule may be linked to an adaptor moiety that, in turn, facilitates linkage to another functional moiety. Sometimes the category-binding molecule has dual non-separable functions. For example, propidium iodide, a nucleic acid stain, can be used as a category-binding molecule (e.g., the category-specific binding site might be the cellular nucleic acid in a yeast) while, at the same time, the bound dye functions as a signaling moiety (i.e., it can fluoresce when bound to the category-specific binding site). Tests based on the invention can incorporate more than one class of category-binding molecule (e.g., antibodies and nucleic acid stain, or antibodies and oligonucleotides).

The simplest tests incorporate a single type of category-binding molecule to scan for a single category of target cell. For example, a test for *M. tuberculosis* might use a monoclonal antibody that binds specifically to a category-specific binding site on the surface of *M. tuberculosis*. In another example, when screening for urinary tract infections, the single category is "all cells"—or, if human cells are lysed, "all non-human cells"—and the single type of category-binding molecule could be a nucleic acid stain (e.g., propidium iodide).

A family of category-binding molecules is a set of distinct category-binding molecules that bind to members of the same category of target cell. For example, a polyclonal antibody raised to Hepatitis C virus is a family of antibodies since it comprises multiple category-binding molecules that bind specifically to the same category of target cell—in this case HCV. Another example of a family of category-binding molecules is a set of 80 category-specific genomic DNA sequences that occur in all *E. coli* O157:H7 strains but do not occur in members of other groups of bacteria. This family of category-binding molecules can hybridize as a group to suitably prepared *E. coli* O157:H7 cells but does not hybridize to other types of cells.

To detect multiple categories of target cells, a test includes one family of category-binding molecules for each category. A set of families of category-binding molecules is called an ensemble of category-binding molecules. For example, tests for pneumonia or tests for drugs of abuse, must distinguish numerous categories of target cells from each other. One family of category-binding molecule is used for each category of target cell. For a pneumonia test, an ensemble of antibodies that react to category-specific antigens on the surface of microbes that cause pneumonia might be used. One family in this category-binding molecule ensemble might comprise polyclonal antibodies from the immunoglobulin fraction of antiserum raised in a rabbit host and directed against *Streptococcus pneumoniae*. Another family could comprise a recombinant antibody or a monoclonal antibody directed against a coat protein of adenovirus.

The number of distinct groups or categories of target cells tested for by an ensemble, i.e., the categorical complexity, is reflected by the number of families of category-binding molecules in the ensemble. The number of families in an ensemble can, in turn, be accurately defined by a quantity called the "minimum categorical derivation" of an ensemble. The family complexity is the minimum number of distinct target cells required to bind members from each of the families of category-binding molecules in the test ensemble. For example, consider an ensemble of category-specific antibodies used to simultaneously test a sputum sample for the presence of *Mycobacterium tuberculosis, Legionella* spp, and *Coccidoides immitus*. The family complexity of the ensemble would be three, since a minimum of three target cells, one from each pathogen category, would be required to bind to members of each family of category-binding molecules in the ensemble. The ability of the invention to identify a broad spectrum of target cell categories in a single test is a consequence of its ability to scan a sample using an ensemble of category-binding molecules that has a large family complexity.

Category-binding molecules used in conjunction with the invention should be specific in that they should bind under assay conditions to the desired target cell but not to other types of target cells meant to be distinguished by the assay or to other possible constituents of the sample or test. Thus, in a test for upper respiratory bacterial infection, potential category-binding molecules are screened to eliminate those that cross react with normal (commensal) microbial constituents of the upper respiratory tract.

Representative methods for obtaining and characterizing category-binding molecules are included in the examples below.

The invention's ability to analyze a sample for numerous disparate categories of target cells simultaneously derives from the ability to differentiate the signals derived from the different categories of target cells. The invention discriminates between categories by labeling each category-specific family of category-binding molecules with signaling moieties such that it has a unique signal signature. The ability to generate and detect large numbers of distinct signal signatures (i.e., high signal complexities) enables construction of tests that analyze for numerous categories of target cells (i.e., highly multiplexed tests).

The invention can exploit various types of signal character including: fluorescence, scattered light, light polarization, chemiluminescence, and radioactivity. Examples of signaling moieties and detection schemes using various signal characters appear below. There can be multiple signal classes within a signal character. For example, if the signal character is fluorescence, various characteristic emission spectra are included in the signal classes (e.g., red fluorescence, green fluorescence, and blue fluorescence). In another example, consider red fluorescent microparticles that are dyed with different concentrations of the same fluorophore. In this case, fluorescence is the signal character, but the different intensities of the particles constitute the classes of signal character, i.e., fluorescence intensity is the quality of the signal character that differentiates one group of particles from another.

A great variety of signaling moieties can be used in conjunction with the invention as demonstrated in the examples below. Signaling moieties can include simple fluorophores, up-regulated phosphors, naturally fluorescent proteins (such as green fluorescent protein and its relatives), dyes, enzyme: substrate systems (generating color changes or chemiluminescence), fluorescent microparticles, light scattering particles, magnetic particles, or radio transmitting microdevices.

Attaining a high signal complexity is key to developing certain tests that scan for numerous types of target cells (i.e., tests with high categorical complexity).

Achieving High Signal Complexity

The number of distinguishable labels (or signaling moieties) in a mixture is called the signal complexity. For highly multiplexed tests, it is sometimes advantageous to use signaling moieties with high signal complexity. Three general approaches that can be used with this invention to generate high signal complexity are: (1) distinct labeling, (2) combinatorial labeling, and (3) ratio labeling.

1. For distinct labeling, probes in different probe families are tagged, with a single signaling moiety that can be readily detected in the presence of all other signaling moieties in the experiment. Thus far, it has been difficult to achieve distinct labeling at high signal complexities. This difficulty is present because most labeling methods use optical signals (e.g., chromogenic, fluorescent, chemiluminescent) or radioactive labeling, and because of the spectral bandwidth of optical signals and the limited range of signals detectable by current instruments, the resolvable signal complexity using optical signals is rather small. For example, the resolution of dozens of fluorophores with distinct emission spectra is currently impossible because of spectral overlap.

2. Another way to achieve the high signal complexity used in the invention is to apply a combinatorial labeling approach. Combinatorial labeling is a technique for achieving high signal complexity using a relatively small number of distinct signaling moieties. With this approach, distinct combinations of signaling moieties are bound to different targets. Currently, fluorophores are a favored class of signal moiety for molecular diagnostics. However, given the complications involved in analyzing multiple distinct fluorophores (arising in large part from overlap of the excitation and emission spectra), it is only currently practical to incorporate about seven or fewer conventional fluorophores. However, used in combination, seven fluorophores can be used to generate 127 distinct signals (N fluorophores generate $2^N-1$ combinations). High signal complexity can also be achieved via combinatorial labeling using other types of signaling moieties. For example, particles impregnated with different dyes, particles that fall into different discrete size classes, or transponders emitting distinct radio signals could be used with this approach. Combinatorial labeling using fluorophores has recently been applied with success for human karyotyping (Speicher et al 1996, supra; Schröck et al 1996, supra). Instrumentation and software for analysis of combinatorial labeling experiments is commercially available.

3. High signal complexity can also be obtained using the ratio labeling approach (Fulton, et al 1997, supra). In ratio labeling, as in combinatorial labeling, many distinct types of signaling moieties are generated using a relatively small number of distinct signaling elements. However, in contrast to combinatorial labeling, the signaling moieties in ratio labeling are distinguished by the ratio of the signaling elements. For example, two fluorophores, X and Y, with different excitation/emission characteristics can be used to dye polystyrene particles. Different relative concentrations of the fluorophores ([X], [Y]) are applied to different sets of particles. For example, eight different concentrations of X and eight different concentrations of Y can be used to dye particles in all combinations ($X_1Y_1$, $X_1Y_2$, $X_8Y_7$, $X_8Y_8$) resulting in 64 classes of distinguishable particles. Ratio labeling simplifies instrumentation, as only a small number of signal types need be used. Signal elements, other than fluorophores and including non-optical signal elements, can also be used to generate high signal complexities using a ratio labeling approach.

Generating Strong Signals to Facilitate the Detection Microcolonies

The level of signal intensity needed is, of course, dependent on the type of signal character and the detection method/instrumentation (see below).

Various approaches for labeling category-binding molecules can be used to achieve the required sensitivity. One method for optimizing the signal strength is to label target molecules with highly fluorescent signaling moieties. For example, quantum dots, fluorescently dyed nanospheres, and polymerized fluorophore molecules generate strong fluorescent signals. Incorporating numerous signal elements can increase the fluorescence intensity of a signaling moiety. For example, fluorescent nanospheres (~20 nm in diameter; Molecular Probes) can generate a signal equivalent to about 180 fluorescein molecules. Fluorescently dyed polystyrene microparticles (e.g., 1 μm in diameter) can incorporate millions of fluorophore signaling elements. A method for incorporating multiple fluorophores in a signal moiety associates with a nucleic acid category-binding molecule is to incorporate fluorophore-dNTP conjugates during PCR amplification of a cloned category-specific sequence. Alternative methods for incorporating multiple fluorophores into nucleic acid category-binding molecules include approaches using: dendrimers, branched DNA, or rolling circle templates bound to multiple signal moieties, or tailing with numerous polymerized fluorophore labeled nucleotides. Conjugating category-binding molecules to multiple signaling moieties also increases signal intensity. For example, signal amplification can also be achieved by conjugating large numbers of signaling enzymes (e.g., alkaline phosphatase or horseradish peroxidase) to a nanoparticle.

Another approach to obtain strong signals is to bind numerous labeled category-binding molecules to each cell. This binding can be achieved by various means including: using multiple category-binding molecules (recognizing multiple category-specific binding sites in the same target cell) or by choosing category-binding molecules that bind to target molecules that are highly represented in a target cell. For example, a labeled microbe-specific polyclonal antibody can achieve high signal intensities by binding to numerous distinct epitopes on a microbial target cell. The strategy of choosing category-specific binding sites that are present in large numbers in each target cell has been frequently used previously. Examples of this strategy include the use of nucleic acid probes for ribosomal RNA (which depending on the target organism and cell type can be present in thousands of copies per cell). Similarly, some antigenic target molecules are present in hundreds or thousands of copies in each cell of a target organism. The invention can exploit both of these strategies. As another example, the large number of category-specific binding sites present in a bacterium yield strong signal intensity when using the nucleic acid-binding fluorescent dye Syber Green I as the category-binding molecule/signaling moiety.

Binding numerous signal moieties to a target cell not only increases signal strength, but it endows the invention with robustness since the chances are small of observing numerous clusters of a large number of signaling moieties with the expected composite signal signature in the absence of the target cell.

Conjugating Signaling Moieties to Category-binding Molecules

The invention can incorporate numerous types of signaling moieties which can be directly conjugated to category-binding molecules using various methods which are known by those familiar with the art (see, for example, Hermanson, G., *Bioconjugate Techniques* (Academic Press, 1996) and specific examples below). For example, antibody or oligonucleotide category-binding molecules can be directly conjugated to a fluorophore or a quantum dot signaling moiety. Alternatively, antibodies or oligonucleotide category-binding molecules can be used to coat fluorescent microparticle-based or light-scattering nanoparticle-based signaling moieties. Signaling moieties can be indirectly conjugated to category-binding molecules. For example, avidin can be directly conjugated to multiple signal elements to constitute a signaling moiety. The labeled avidin molecule can then be bound to a biotinylated category-specific antibody. Signaling moieties can be conjugated to the category-binding molecules before, during, or after the binding steps. For example, in one embodiment of the invention, digoxygenin-labeled nucleic acid probes are used as the category-binding molecules. After binding the category-binding molecules to the category-specific binding sites in the target cells in the sample, the unbound probes are washed away. Anti-digoxygenin antibody:alkaline-phosphatase conjugates (the signaling moieties) are then conjugated to the bound digoxygenin-labeled probes. An alkaline-phosphatase substrate (e.g., the chemiluminescent substrate CDP-Star; NEN)) is then added to the bound alkaline-phosphatase to generate the signal.

Step 2: Depositing the Cellular Targets in the Detection Area

Depositing the target cells in the sample in the detection zone is generally the next step in applications based on the invention. Essentially planar detection zones are often used, in part, because optical imaging systems can efficiently collect light from thin detection zones (i.e., optical systems with a small depth of field), for example, when microcolonies are grown on the surface of the nutrient agar or on membranes lying on the surface of nutrient agar plates. In these cases, the depth of the detection zone can be negligible compared to the lateral dimensions of the detection zone. This step can also be used to deposit certain target cells selectively, to remove substances that might inhibit cell growth, or to contact target cells with labeling reagents.

Using membrane filtration to deposit cells on a roughly planar membrane detection surface has several advantages. The ability to collect small numbers of target cells from large sample volumes is one important advantage of using membrane filtration. For example, a single bacterial cell in 1 liter of water can be quickly and efficiently deposited on the surface of standard filtration membranes. Water can pass freely through the membranes but cells can not, because of the size of the membrane's pores. The water sample is poured into a container the base of which formed a membrane and then a vacuum is applied to the bottom surface of the membrane. Water is drawn through the membrane while cells are retained on the membrane surface. The membrane can be optionally washed with liquid to efficiently remove substances such as growth inhibitors or to expose cells to labeling reagents. The membrane can then be placed on growth media.

Other methods for depositing the target cells on a surface include centrifugation, gravitational settling, magnetic selection, or binding to surface bound category-binding molecules (e.g., capture antibodies). In some cases (e.g., magnetic separation) a distinct moiety, the selection moiety is used. Magnetic microparticles coated with category-specific antibodies are an example of a selection moiety. After target cells are allowed to bind to the antibody-coated magnetic particles, a magnetic field is applied to deposit the magnetically labeled cells on the detection surface. Similarly, dense microparticles coated with target-specific antibodies can be used as selection moieties. In this case, the labeled cells are brought to the detection surface by the action of gravity on the dense particles.

Step 3: Allowing Cellular Replication to form Microcolonies

In this step, target cells form microcolonies by dividing in place in the detection zone. Microcolony growth is supported by exposing cells to growth medium containing nutrients and incubating them under conditions that foster cell growth and division (these parameters are selected in Step 1 above). In a typical embodiment, cells are deposited on a porous membrane filter. The filter is placed on the surface of solidified nutrient agar growth medium in a petri dish, which is then covered and placed in an incubator set at the appropriate temperature. This method is currently used widely to support colony growth using traditional microbial culture because nutrients can diffuse freely through the membrane without causing movement of daughter cells from the progenitor cell. Alternatively, microcolonies can be grown directly on the surface of nutrient agar medium or the equivalent.

Selection for specific growth of the target cells can occur in the microcolony growth step. For example, a test might be designed to detect anaerobic bacteria in a sample (such a test is generally required for injectible pharmaceutical finished products, for example). In this case, the growth step could be carried out under an anaerobic atmosphere in a bell jar. Selective growth media can also be used to achieve selective microbial growth at this step. For detecting bacterial resistance to antibiotics, for example, cells are generally incubated in the presence of various antibiotics at several concentrations. Resistance to a certain concentration of antibiotic is inferred if a bacterial strain grows comparably in the presence and absence of antibiotic at that concentration.

The invention can detect various colony morphologies. Many types of growing cells form simple discrete dome-shaped colonies on common substrates (nutrient agar media and membranes). Others form irregularly shaped colonies or filamentous colonies. Furthermore, colony morphology can depend on growth conditions (e.g., nutrients, temperature, and substrate). Some types of cells are mobile and do not form discrete colonies at all. If it is important to detect the growth of such organisms motility inhibitors can be added to the medium. Thus, growth conditions should be chosen and control experiments carried out to insure that target cells form detectable microcolonies. If necessary, growth conditions can be modified or multiple conditions may be used in parallel tests.

Step 4: Optional Labeling of Microcolonies

In this optional step, category-binding molecules and associated signaling moieties (also called the probes, labels, or stains) are brought into contact with target cells in the sample under conditions that facilitate specific binding. For example, an ensemble of category-specific nucleic acid sequences is hybridized to complementary target sequences in the sample in this step. Similarly, category-specific antigens in the sample are allowed to bind to the corresponding category-specific antibodies.

There are several possible physical configurations for the binding step and binding can be carried out at various points in the testing procedure. For example, target cells can be labeled in a liquid sample before depositing the target cells in the detection zone. Unbound probes can then be effectively removed during the depositing step or by washing. A disadvantage of this approach is that the signal generally does not increase with microbial growth. Stronger signals are generally obtained by labeling microcolonies during or after microbial growth. The labeling reagent can be added to the nutrient media so that the microbes are continuously exposed to the reagent during growth. Alternatively, microcolonies can be exposed to the probes after growth. For example, microcolonies on a membrane can generally be fixed and the relevant category-specific binding sites exposed by drying, heating, and/or exposure to chemicals (e.g., NaOH or chloroform vapor). Labeling can then be effected by overlaying the microcolonies with the labeling reagent or by placing the membrane on a pad that has been saturated with the reagent. Generally, a washing step is used to remove unbound reagent. The concentration of the category-binding molecules is optimized to achieve rapid binding kinetics. The chosen conditions for selecting for specific binding depend on the characteristics of the category-binding molecules and their interactions with target molecules. Specific conditions and procedures are described in the examples below.

Step 5: Enumerating the Microcolonies

Enumerating the target cells in the sample occurs in the final step of testing applications based on the invention. The enumeration step itself comprises the steps of imaging, image analysis, and report generation.

The invention can detect microscopic colonies with no magnification. Low magnification imaging facilitates the imaging of a large area which, in turn, facilitates scanning large samples. Some embodiments of the invention detect microscopic colonies without magnification, in part, by using high efficiency optics to direct photons emitted by the microcolony into a small number of pixels of photodetector arrays.

The imaging method used depends on the type of signal generation chosen in step 1. For example, the imaging process is different depending on the optical property or signaling character that is used for signal generation. For some signal characters (e.g., reflectance, fluorescence, light scattering, absorbance), the complexes in the detection zone must be illuminated by a light source. For others (e.g., chemiluminescence, thermal radiation), illumination is not required. Various detectors can be used including electronic photodetectors, film, and direct visualization.

Detection of individual microcolonies is naturally quantitative and ultra-sensitive. Quantification can be accomplished manually by counting individual cells in a photographic or digital image or by using automated image analysis of digitized images. Integrating signal intensity over the sample can also be used to quantify the target cells. Signal integration is particularly useful with samples containing high concentrations of target cells. In these cases, resolving coincident signals may not always be possible.

Decoding the signatures of labeled probe families allows identification of numerous categories of target cells. An important goal of this step is to identify the category of target cells in the sample by determining the signature of labeled category-binding molecules that have adhered to the sample.

The CCD camera-based imager, shown in FIG. 3, is a useful device for large area imaging using when fluorescence is used as the signal character. This device was used to collect the data for many of the examples below. Excitation light may be provided by introducing light from a high intensity white light source (1000 W Xenon arc lamp, Model A-6000, Photon Technology Incorporated, Monmouth Junction, N.J.) into a liquid light-guide (5 mm core diameter, Model 380, Photon Technology Incorporated, Monmouth Junction, N.J.). The liquid light-guide carries the light to an excitation filter-wheel (BioPoint FW, Ludl Electronics, Hawthorne, N.Y.) and directs the filtered beam (e.g., 9 mm or more in diameter) onto the detection surface containing the microcolonies. The apparatus can detect microcolonies in various configurations (e.g., on the surfaces of nutrient agar, microscope slides, coverslips, or tubes or wells with flat, optically clear, bottoms; or immobilized in nutrient agar or other substances). The incident light strikes the detection surface inducing fluorescence in the target cells. A portion of the emitted fluorescent light is collected by a high-collection efficiency lens system and transmitted through an emission filter-wheel (BioPoint FW, Ludl Electronics) to a CCD Camera (Orca II, Hamamatsu, Bridgewater, N.J.). The design and construction of the optical train is based on principles and practices known to workers familiar with the art.

The invention can also incorporate other types of photodetectors and other configurations. The sensitivity of the imaging system can be increased by choosing a more sensitive camera (e.g., a camera cooled to a lower temperature, or a camera that uses a back-thinned chip). Alternatively, the detection sensitivity and resolution can be increased by implementing a line scanning system (e.g., BT Image Array; Hamamatsu). For line scanning, a linear CCD or photodiode array (e.g., 1×500 or 1×1000 pixels) is used to capture the image. The resolution in one dimension corresponds to the number of array elements, while the second dimension is generally captured by moving the sample slide perpendicularly under the linear array. Since there are fewer elements, similar sensitivity linear arrays are typically less expensive than area format CCD cameras.

The instrument diagrammed in FIG. 3 facilitates signal measurement from multiple samples by using an X-Y positioning Stage (BioPoint XY, Ludl Electronics) to move the sample vessel (e.g., microtiter plate) over the excitation and collection optics. Image-Pro and Image-Pro add-ins control all instrument components and image acquisition. Filter wheels are managed with the ScopePro add-in (Media Cybernetics, Baltimore Md.), and the StagePro add-in (Media Cybernetics, Baltimore Md.) handles stage positioning, while the camera control is via the Hamamatsu Orca II driver (Hamamatsu, Bridgewater, N.J.). Image-Pro Plus is also used for Image-Processing and analysis as described below.

Embodiments of the invention using white light illumination utilize spectral filters to provide an optimal excitation peak for each of the fluorophores. The white light spectrum is large, allowing a wide variety of fluorophores to be selected to eliminate emission spectrum overlaps. Typically spot sizes achievable with white light illuminators, e.g., 2 mm to 5 mm, are appropriate for large area imaging. Since filter changes are relatively simple, and can be automated, white light systems are very adaptable, allowing the same apparatus to be used for tests that use distinct sets of fluorophores.

The collection efficiency of the system shown in FIG. 3 is maximized by incorporating a custom designed collection optic consisting of two components: a collection objective and a focusing element. The collection objective has high collection efficiency ($\cong$f#/1.2) and outputs a relatively collimated beam. The focusing lens captures the light output from the collection objective and focuses it onto the detection surface of the CCD. The optics are designed in two parts to allow a filter wheel to be inserted in the path of the collection lens. For certain embodiments of the invention, e.g. for some embodiments that do not require filter changes, it may be desirable to include a tapered optical fiber bundle for achieving high collection efficiency. The fiberoptic bundle contains fibers that collect light proximally to the sample and channel the light directly to a CCD chip. Alternatively, the invention can detect signals very sensitively using direct proximal detection in which the sample is applied directly or in close proximity to the CCD chip (for highest sensitivity to the back of a back-thinned CCD chip).

In addition to the white-light, multi-spectral system described above, we have also developed a simpler single-color fluorescence imaging system for non-magnified large area imaging. In the system shown in FIG. 4, excitation light is provided by a 532 nm Frequency-Doubled Diode Laser (50 mW, Model # BWT-50E, B&W Tek, Newark, Del.). Since this detection uses a single color, filter wheels are not necessary. A single excitation filter removes harmonics from the laser output (Model HQ532/10x, Chroma Technology, Brattleboro, Vt.) and a single emission filter (Model HQ620/60m, Chroma Technology, Brattleboro, Vt.) allows only specific fluorescent signals to pass to the CCD camera. The systems also use a less-expensive CCD camera (Model KX-2E, Apogee CCD, Auburn, Calif.) than the one described previously, to capture images. The instrument can easily be adapted to multicolor analysis by incorporating multiple lasers and filter sets.

The CCD cameras incorporated in the invention are generally cooled to a temperature between −5° C. and −50° C., sufficient for integration times from ten seconds to about two minutes (depending on the camera sensitivity) with minimal camera noise build-up. Longer integration times generally give higher sensitivity by allowing the collection of the photons emitted from the fluorophores for an extended period. Long integration times are inappropriate for line scanning; however, there are back-thinned linear arrays available that have very high quantum efficiencies, increasing sensitivity.

The invention can also use interferometer-based spectral imaging for the detection and decoding of signals (Schrock, E., 1997, supra). Using this technique, light emitted or scattered by signaling moieties is split into two paths, passed thorough prisms (so that different wavelengths travel different distances), and allowed to recombine to create an interference pattern. Fourier analysis of the interference pattern generates a spectrograph for each point in the image.

Alternatively, photographic film can be used to record images of the target cells inexpensively in a sample. When the signaling character is chemiluminescence, this approach is most easily implemented. Images collected on film can be digitized in commercial scanners for data storage and for digital image analysis.

For embodiments of the invention that generate digital images, computer software identifies and quantifies the target microcolonies. For a typical assay in which different classes of fluorescent signaling moieties are used, the software superimposes the appropriate fluorophore-specific images, identifies the target cells by determining which signature or combination of signals is emitted by each target microcolony, and enumerates each category of target microcolony that is present in the sample. The software may also: (1) correct for illumination non-uniformity; (2) correct for fluorescence cross-talk through a deconvolution matrix; (3) align images using registration marks imprinted on the substrate; (4) compare images from different time points; (5) apply algorithms for discerning growing microcolonies from non-growing objects; (6) assign an ID code to each imaged microcolony in the sample based on comparison to a look up table; (7) record the imaged sample bar code for sample identification; and (8) automatically save the output data, images, and bar code to a database that can be queried, e.g., via a web browser interface. Commercially available image analysis packages can be used to provide these functions. Software packages for multicolor image analysis can be used (e.g., Image-Pro, Media Cybernetics; MetaMorph, Universal Imaging; MatLab; The MathWorks).

It is useful to outline here the software packages and methods that were used to analyze the fluorescence data collected in many of the examples that follow. The detection surface was imaged to determine the number of fluorescent objects and/or the total fluorescent signal. The fluorescence was captured from the membrane by a CCD camera and stored as a TIFF (Tagged Image File Format) image file that contained records of pixel locations and intensities. Three approaches were used to quantify the assay results. The total integrated signal of the imaged detection zone was determined by summing the fluorescent signal from all of the pixels. The integrated signal from the sample was compared to that of negative controls. Measuring the total integrated signal is especially useful for samples containing numerous target cells. A second approach was to count the fluorescent objects in the detection zone. A third approach was to integrate the intensity of all of the pixels contained within the fluorescent objects (as opposed to summing the intensity of all of the pixels in the image). All image analysis was performed using Image-Pro v 4.0 (Media Cybernetics, Silver Springs, Md.).

Obtaining the total integrated signal was achieved by initially defining an area on the membrane (the area of interest). Image-Pro allows the area of interest to be converted into a single object and other Image-Pro tools permit the total signal of the pixels represented in this object to be summed. A similar image from a membrane onto which no target cells were added was then analyzed in the same way and used as a negative control. The negative control values were subtracted from the values of target containing samples. This subtraction removed both assay and electronic noise.

The second and third quantification methods used Image-Pro's object-finding utility. This utility joins contiguous pixels that have a value (signal) above an automatic or user-defined threshold. This establishes a contour line around the perimeter of the object. The perimeter pixels and those inside are defined as the object, and summing these pixel values results in the object integration value. The analysis software was then used to count all the objects in an area of interest that represents the bottom of the sample container and, in addition, could be used to calculate the integrated signal intensity of all objects found.

Using the IPP Image-Pro macro language, the above utilities can be automated to allow batch processing of several images at one time. In addition, the data can be manipulated with other user-defined IPP scripts. For example, objects below or above a certain size (area) or intensity can be included or excluded, which can be a useful tool for dust exclusion. Other important parameters for image analysis that determine object definition (e.g., acceptance and rejection criteria) vary by application and should be optimized accordingly.

Various aspects of the invention can be automated including linking the steps outlined above. Consider an application for analyzing liquid samples such as pharmaceutical water for injection or a clinical urine sample. The automated system, starting with the sample in a collection beaker, could collect the target cells onto a membrane by filtration, place it on growth media, incubate the target cells under growth conditions, image the membrane at regular intervals, and report the results. Alternatively, individual functions of the invention can be automated. For example, modules for automatically loading and unloading petri dishes (or alternative disposables used for growing microbes) into the imaging instrument and for automatic focusing can be incorporated into the system.

EXAMPLES

The examples below provide technical details for implementing various embodiments of the invention for use in conjunction with a range of applications are not intended to be limiting.

Example 1

Detection and Identification of Bacterial Microcolonies using Non-Magnified Large Area Imaging Background and objectives: Detection of microbial growth is at the core of both clinical microbiology (e.g., bacterial identification and antimicrobial susceptibility testing) and industrial microbiology (e.g., mandated sterility testing), but the commonly used methods are slow. The consequent delays in analysis cause needless death and suffering in clinical situations and exact a large financial cost in industry.

Using non-magnified large area imaging to detect individual microcolonies exploits the advantages of microbial culture while avoiding the substantial disadvantages of traditional and emerging methods. Advantages of in situ replication analysis using the invention are: speed; ease of multiplexing (scanning for more than one microbe); and the ability to detect and identify without sacrificing microcolony viability (essential for efficient antimicrobial susceptibility testing).

Experimental objective. The example demonstrates the invention's ability to detect in situ replication of bacterial microcolonies. The principle of the method is diagrammed in FIG. 7. Bacteria are deposited on a filter and allowed to replicate in situ. The resulting microcolonies were labeled in two ways: with the nucleic acid stain Syber Green I and by binding to group-specific antibodies labeled with FITC. The labeled microcolonies were then detected using CCD-based non-magnified large area imaging.

Experimental methods. *E. coli* MG1655 cells were grown overnight in LB medium to a density of approximately $10^9$ cells/ml. The approximate number of cells was determined by counting dilutions of the overnight culture in a hemocytometer. The overnight culture was then diluted to achieve about $10^3$ cells/ml. One milliliter of the dilution was deposited on a black polycarbonate filter (Osmonics; cat. num. K02BP04700) using a vacuum filtration device and a plastic funnel cup (Millipore Microfil V User Guide, PF07114, Rev A 3/00). Sixteen separate filters with ~1000 cells were prepared in this manner, four filters for each of four time points (0, 1.5, 3 and 24 hours). After filtration, each filter was placed on a separate agar plate containing LB growth medium, which was pre-warmed to 37° C., and placed in a 37° C. incubator. Periodically (0, 1.5, 3, 24 hours) four filters were removed from the incubator. Two of these filters were fixed in 3.0% formaldehyde for 10 minutes, by adding the filter bacteria side up on top of a 500 μl spot of formaldehyde which was spotted on a piece of Parafilm™. After fixation the filters were put on an absorbent pad to soak up the excess formaldehyde. Next a 10×solution of Syber Green I (200 μl, Molecular Probes) was added on top of the filter. The cells were allowed to stain for 10 minutes. The other two filters not used in the nucleic acid staining were blocked with PBS-B for 15 min and then FITC labeled anti-*E. coli* antibodies (Fitzgerald) were added to the filters. After 30 minutes of incubation, the filters were placed on an absorbent pad to soak up any residual liquid. All membranes were then imaged by placing the filter on a CCD-base imager (described in Step 5 of Detailed description section and shown in FIG. 3) so that the bacteria were facing the illumination source and CCD chip.

Results. In this example single cells were allowed to go through several replicative generations in order to from microcolonies. The microcolonies were labeled with either Syber Green I or a FITC-labeled antibody. In FIG. 6 the upper row of panels shows the 0 hour time point containing single cells. The lower row of panels shows microcolonies after 3 hours of incubation. There was a substantial increase in size and signal of the objects detected by CCD imaging over time due to the increase in the number of cells at the sites where the colony-forming cells were originally deposited. The detection of growth is central to medical and industrial microbiological practice. This example shows that the invention can dramatically decrease the time required for detection of microbial growth.

Example 2

Autofluorescence-based Detection of Bacterial Microcolonies using Non-Magnified Large Area Imaging Background and objectives: The importance of methods that detect microbial growth and the limitations of current methods are discussed in the Background section. This example demonstrates a very simple yet powerful method based on the present invention that rapidly detects the growth of bacterial microcolonies. The method relies on the intrinsic fluorescence (autofluorescence) of the target cells for generating detectable signal. Thus, this method does not use category-binding molecules or exogenous signaling moieties to achieve non-magnified large area imaging of microscopic target cells. The advantages of reagent-less non-destructive enumeration include generation of purified cultures (for microbial identification and antibiotic susceptibility testing, improved method validation, and the ability to follow microbial growth over time (for object discrimination and growth kinetics).

Experimental methods. *E. coli* MG1655 cells were grown as in Example 1. Bacterial cells were diluted serially (ten-fold dilutions) with sterile PBS. Bacterial cells (50 ml volume of the $10^{-7}$ dilution) were deposited on a black polycarbonate filter (Osmonics; cat. num. K02BP04700) using a vacuum filtration device and a plastic funnel cup (Millipore Microfil V User Guide, PF07114, Rev A 3/00). A negative control was prepared by filtering sterile PBS. After filtration, each filter was placed on a separate agar plate containing LB growth medium, which was pre-warmed to 37° C., and placed in a 37° C. incubator. The viable cell count of the $10^{-7}$ dilution was determined by filtering replicate samples and incubating the filter on LB agar. This process indicated that the $10^{-7}$ dilution contains approximately 1000 cells per 50 ml. At 5.25 hours, membranes were imaged by placing the filters held on glass microscope slides into a CCD-based imager (described in Step 5 of Detailed description section and shown in FIG. 3) so that the bacteria were facing the illumination source and CCD camera. A FITC optical filter set (Chroma; excitation 470/40 nm, emission 522/40 nm) was used and a one second exposure captured using software control (Image Pro Plus, version 4.1; Media cybernetics).

Results. FIG. 7 shows the autofluorescence-based detection of bacterial microcolonies after 5.25 hours of growth. A filter containing microcolonies provided strong signals after a one second exposure (FIG. 7, left panel), while a filter lacking microcolonies, but that was otherwise identically processed and imaged, did not exhibit such signals (FIG. 7, right panel).

The example demonstrates that this very simple embodiment of the invention is a powerful approach for microbial growth detection. The technique could be used to make many important microbial diagnostics applications more efficient including sterility testing, environmental and water testing, microbial identification, and microbial susceptibility.

Example 3

A Simple Method for Validating a Rapid Reagent-Less Microbial Enumeration Test using an Internal Comparison to the Traditional Culture Method Background and objectives: Proving the equivalence of a new microbiological test to the "gold standard" method is an essential task for both the developers of new methods and their customers. Formalized validation requirements are generally codified in governmental regulations that guide the introduction of new microbiological methods in industry and healthcare. New methods for microbiological testing in the pharmaceutical industry have sometimes floundered because of the difficulty of proving equivalence to the accepted methods. The goal of this example is to demonstrate a simple method for proving the equivalence of a test based on the invention to the traditional microbial culture test.

Experimental methods. *E. coli* MG1655 cells were grown and analyzed as in Example 2. After imaging the microcolonies, the filter was re-incubated at 37° C. for about 15 hrs. The resulting macrocolonies were imaged using reflected white light supplied by an incandescent microscope lamp shining obliquely on the plate. Otherwise, the same imaging system was used to collect the reflected light as was used to detect microcolony autofluorescence.

Results. That this embodiment of the invention does not harm the microbes is apparent by comparing the left and right panels of FIG. 8. The exact correspondence between the "ancestral" microcolonies (left panel) and their "descendant" macrocolonies (the right panel) by this internal comparison should facilitate demonstration of equivalence to the traditional microbial culture enumeration test.

Example 4

Accuracy and Limit of Detection of Autofluorescent Microcolony Detection using Non-Magnified Large Area Imaging Background and objectives: Accurate detection of small numbers of microbes is critical in both healthcare and industrial microbiology. For example, only one bacterial cell in a 10 ml blood sample may be present in a patient with a potentially fatal blood infection. Similarly, sterility testing of an injectable drug in pharmaceutical manufacturing must detect a single living microbial cell in a sample. In both cases, false negative results and false positive results can have severe consequences. The fraction of test results that are false positives and false negatives defines the accuracy of a test method.

The goal of this example is to show the accuracy of the invention at the lowest level of target cells.

Experimental methods. *E. coli* MG1655 cells were grown and analyzed as in Example 3. However, for this example a dilution of cells was applied to multiple filters (n=101) so that on average the detection zone on about one in five filters was expected to contain a single target cell. After 5 hr of incubation each filter was imaged and scored for the presence of microcolonies. The filters were then re-incubated overnight and scored for the presence of macrocolonies. The results obtained using the invention were then compared to the results obtained using traditional visual method.

Results. FIG. 9 shows the method used in this example to measure the accuracy of the invention when the samples contain the extremely low levels of target cells. For each of the 101 filters, the result obtained by scoring the microcolonies was the same as the result obtained by the traditional method. As judged by either the presence of microcolonies or macrocolonies, most filters (n=80) had no deposited target cells. Furthermore, the filters containing deposited target cells (n=21), the microcolonies occurred in the same numbers (several filters had multiple target cells, as would be expected statistically) and with the identical placement on the filters as did the macrocolonies, adding further robustness to the results. The invention and the "gold standard" method were in 100% agreement, with no false positives or false negatives detected. Thus, the results indicate that the invention is accurate at very low target cell levels.

Example 5

Determining the Number of Microbial Cells in Autofluorescent Bacterial Microcolonies Rapidly Detected using Reagent-less Non-magnified Imaging Background and objectives: The goal of this example is to demonstrate the sensitivity and speed of reagent-less detection of microcolony autofluorescence using large area imaging. Rapid detection of microbial growth is the result of the invention's ability to detect microcolonies at early stages when the number of cells is small. The experiments in the example determine number of bacterial cells in microcolonies detected by non-magnified CCD imaging.

Experimental methods: A single colony of freshly grown *Escherichia coli* (ATCC, Cat. No 8739) was inoculated into a conical tube (50 ml) containing growth medium (TSB; 10 ml) and incubated (16 hours, 37° C., 150 rpm). This culture containing stationary phase cells ($2.4 \times 10^9$/ml) was used to inoculate an Erlenmeyer flask (500 ml) containing pre-warmed TSB (37° C., 100 ml) to produce a log phase culture for optimal time to detection. This flask, containing pre-warmed TSB was inoculated with the stationary phase culture (100 μl) and incubated 2 hours, 37° C., 150 rpm). A culture established in this way was found to contain ~$5 \times 10^7$ bacteria/ml via pour plate titration. The log phase culture was diluted in PBS ($10^{-6}$). A volume (10 ml) of this dilution was filtered through a membrane (Chemunex Inc., Chemfilter CB0.4, Black, PET-23, 25 mm) supported over an absorbent pad (Whatman Inc., Cat. No. 1441325) using a filtration device (Millipore Inc., 1225 Sampling Manifold, Cat. No. XX27 025 50). After the bacteria were collected on the membrane, the membrane was placed on a pre-warmed TSA plate (32.5° C.). An image of the plate was captured (30 sec exposure) using non-magnified large area imaging with a FITC optical filter set (Chroma; excitation 470/40 nm, emission 522/40 nm) using software control (Image Pro Plus, Media Cybernetics). Following this initial image capture the plate was placed in an incubator (32.5° C.) for growth. The plate was removed from the incubator after 2.5 hours of growth and the same field was imaged again using the image capture settings applied previously. Following image capture, the membrane was immediately fixed (1.5% formaldehyde in filtered type 1 water for 5 minutes) followed by two washes (PBS, 5 min each) by placing the membrane on 3M Whatman paper impregnated with either fix or wash solutions as indicated. The membrane was placed on the sampling manifold with all but one placement blocked off with a stopper. Vacuum filtration was applied for 15 seconds. To stain the membrane in order to enumerate the bacteria in an individual microcolony, propidium iodide (1 ml, 5 μg/ml) was added to the wall of the cup while vacuum pressure was applied, followed by type 1 water (1 ml). Vacuum pressure was applied for an additional 15 seconds after which the membrane was removed and placed on a glass slide, dried, and mounted with a coverslip using the Pro Long Antifade Reagent (Molecular Probes, Eugene, Oreg., Cat. No. P-4781). The stained microcolonies were imaged using fluorescence microscopy (Axioplan II fluorescent microscope, Carl, Zeiss Inc., Thornwood, N.Y.; Cy3.5 filter set, Chroma Id. No. SP-103, excitation 581/10 nm, emission 617/40 nm, 400x) fitted with the SPOT RT camera (Diagnostic Instruments, Sterling Heights, Mich., Model No. 2.3.1, 2 seconds, red spectra only selected) following spatial registration of these with their corresponding unstained microcolonies identified using large area imaging.

Results: FIG. 10 shows the results obtained in this example. Three microcolonies detected after 2.5 hr of growth at 32.5° C. using the invention were stained and analyzed using high power microscopy. The three microcolonies contained 45, 48, and 50 cells, respectively. No single bacterial cells were observed near the microcolonies demonstrating that the microcolonies remained intact throughout the staining procedure. Note that visible colonies of *E. coli* (~1 mm diameter) contain approximately one million times this number of cells. Thus, using non-magnified reagent-less detection, the invention can detect microcolonies after only a few generations of cell division.

Example 6

CCD-based, Non-magnified, Large Area Imaging Detection and Identification of Bacterial Microcolonies in an Environmental Water Sample Background and objectives: This example aims to show the power of the invention for rapid detection of microbial growth when applied to a variety of anonymous environmental microbes that are likely to be nutritionally stressed.

Water is a common ingredient in the production, processing, and formulation of many pharmaceuticals. Detection of bacteria in pharmaceutical water is a fundamental step in the manufacturing process because the bacteria themselves or their metabolic products could cause adverse consequences if is present in the final product. Proliferation of bacteria may occur in the production, storage, and distribution of this substance. Drinking water is the source feed water for pharmaceutical water and it is the major exogenous source of microbial contamination. Fecal coliforms and a wide variety of microorganisms, largely Gram-negative bacteria, may be present in drinking water. The commonly used methods to detect bacteria in water are slow and thus hamper timely system control.

Using non-magnified large area imaging to detect individual bacterial microcolonies exploits the advantages of in vitro replication analysis while avoiding the substantial disadvantages of traditional and emerging methods. Advantages of in situ replication analysis using the invention are: speed and the ability to detect and identify without sacrificing microcolony viability (useful for identifying the source of microbial contamination in a product or process or determining whether a particular microorganism is harmful to the products or processes in which the water is used.)

Experimental overview. The example demonstrates the invention's ability to detect in situ replication of bacterial microcolonies before these colonies grow into macrocolonies. Bacteria are deposited on a filter and allowed to replicate in situ. The resulting microcolonies and macrocolonies were detected using CCD-based, non-magnified, large area imaging using autofluorescence (FITC excitation and emission filters) and reflectance of white light.

Experimental methods. Water was aseptically collected from the Charles River (Cambridge, Mass.) and used in the experiment within one hour of collection. The Charles River water was centrifuged at a setting of 14,000 rpm in an Eppendorf Centrifuge 5415C for 1-2 seconds. The centrifuged Charles River water was diluted 1:10 with sterile Type I water and 1.0 ml of this was deposited on a black, mixed cellulose ester filter (Millipore; cat. num. HABP04700) using a vacuum filtration device and a sterile plastic funnel (Millipore Microfile® 100 ml Funnel, cat. num. MIHABG072). Each filter after filtration was placed on a separate agar plate containing R2A growth medium (Becton Dickinson/Difco; cat. num. 218263). Ten separate filters were prepared and the agar plates were incubated at 32.5° C. for up to 74 hours. Periodically (after 17, 24, 42, 50, 68, and 74 hours) the agar plates were removed from the incubator and the filters were imaged by placing the plates on a CCD-based imager so that the bacterial colonies were facing the illumination source and CCD chip. The illumination source for reflectance was provided by a Fiber-Lite® Model 190 Convection Cooled 30 Watt Quartz Halogen Illuminator (Dolan-Jenner Industries, Inc., Lawrence, Mass.), and the illumination was directed at an oblique angle onto the filter. The naked eye is capable of seeing bacterial colonies that are 0.5 mm or greater in diameter, so this size criterion was used as a discriminating characteristic of a bacterial colony. The colonies that were 0.55 mm or greater in diameter were identified and counted in the reflectance images. When autofluorescent microcolonies that gave rise to a macrocolonies could be detected was also determined. Autofluorescent images were analyzed to determine when the progenitors of 74 hr macrocolonies appeared. At various time points the percentage the 74 hr macrocolonies that were detectable as autofluorescent microcolonies was plotted.

Results. In this example bacterial cells from a water sample were allowed to replicate in order to form microcolonies and macrocolonies. Both types of colonies were detected by using the invention and identified by autofluorescence and reflectance. The data shown in FIG. 11 indicates that the number of colonies that can be visually observed increased from 11% (6 colonies) at 17 hr to 100% (53 colonies) at 74 hr. Ninety-four percent (50 colonies) of the macrocolonies detected at 74 hours were detected as autofluorescent microcolonies at 24 hours. This example shows that the invention can dramatically decrease the time required for detection of bacterial growth and thus decrease the amount of time needed for a bacterial test for water.

Example 7

Correlation Between CCD-based, Non-magnified, Large Area Imaging Detection of Bacterial Microcolonies and a Traditional Method for Enumerating Bacteria Background and objectives: The goal of this example is to determine the numerical correlation of the results obtained using the present invention to detect microcolonies rapidly and those obtained using slower traditional microbial culture.

Experimental objective: The example compares the enumeration of microcolonies by the invention and the classical "pour plate" culture method. Bacteria were deposited on a filter and allowed to replicate in situ. The resulting microcolonies were detected using CCD-based, non-magnified, large area imaging using autofluorescence (FITC excitation and emission filters). The number of microcolonies obtained with the invention was then compared to the number of macrocolonies that were obtained with the pour plate method.

Experimental methods: *E. coli* 8739 cells were grown overnight in TSB to a density of approximately $10^9$ cells/ml. Ten fold serial dilutions starting with approximately $10^7$ cells/ml and ending with approximately $10^2$ cells/ml of the overnight culture were made in PBS. An aliquot from each serial dilution was further diluted with PBS such that 1.0 ml would contain approximately 50 bacteria. One milliliter was placed in a petri dish together with 35 ml of melted (47° C.) Tryptic Soy Agar (TSA) (Becton Dickinson/Difco; cat. num. 236950). The agar plates were allowed to cool at room temperature and then the plates were incubated overnight at 32.5° C. Ten agar plates were prepared for each serial dilution. Macrocolonies in the agar plates were counted by visually inspecting the plates. Dilutions of bacteria (11.3 ml) were deposited on a black mixed cellulose ester filter (Millipore; cat. num. HABP04700) using a vacuum filtration device and a sterile plastic funnel (Millipore Microfil® 100 ml Funnel, cat. num. MIHABG072). Each filter was placed on a separate agar plate containing TSA. Ten separate filters were prepared for each serial dilution, and the agar plates were incubated at 32.5° C. for 7 hours. The plates were then removed from the incubator, and the filters were imaged by placing the plates on a CCD-based imager so that the bacterial colonies were facing the illumination source and CCD chip. Autofluorescence from each microcolony was detected using FITC excitation and emission filters. Eleven times more volume was used with the filter because each image constitutes approximately $\frac{1}{11}^{th}$ of the entire filter surface. Thus, each image should contain approximately the same number of bacteria as was put into each pour plate. The number of microcolonies in each image was determined by visually inspecting the image. The number of bacteria in each serial dilution was calculated by multiplying the number of microcolonies or macrocolonies by a dilution factor.

Results: In this example bacterial cells were allowed to replicate and form microcolonies on a filter or macrocolonies in agar plates. The microcolonies were detected using the invention, and the macrocolonies were detected using a classical culture method and visually inspecting the agar plates. The concentration of bacteria as determined by each method for each serial dilution was plotted, and the results are shown in FIG. 12. Each point represents the average of ten separate determinations. A positive correlation was obtained between the results obtained with the invention and the results obtained with the classical pour plate method. The correlation coefficient of 0.9996 indicates a strong linear relationship between counting microcolonies with the invention and macrocolonies with a classical culture method.

Example 8

Dynamic Range and Linearity of a Reagent-less Enumeration Test

Background and objectives: Two of the validation criteria for a new microbiological testing method are the range and linearity of the new method. The range is the interval between the upper and lower levels of microorganisms that have been demonstrated to be determined with precision, accuracy, and linearity using the new testing method. The linearity of a microbiological test method is its ability to elicit results which are proportional to the concentration of microorganisms present in the sample within a given range.

The example demonstrates the invention's linearity over a range of bacterial levels. The invention detects the presence of microcolonies on the surface of a filter and quantifies the autofluorescent signal of the microcolonies by using CCD-based, non-magnified, large area imaging.

Experimental methods. *E. coli* 8739 cells were grown overnight in TSB to a density of approximately $10^9$ cells/mi. Ten fold serial dilutions starting with a $10^{-4}$ dilution of the overnight culture and ending with a $10^{-9}$ dilution were made in PBS. Five ml of each serial dilution was deposited onto a black, mixed cellulose ester filter (Pall Gelman Laboratory; cat. num. 66585) using a vacuum filtration device and a sterile plastic funnel (Millipore Microfil® 100 ml Funnel, cat. num. MIHABG072). Each filter after filtration was placed on a separate agar plate containing Trypticase Soy Agar with Lecithin and Polysorbate 80 (Becton Dickinson BBL, cat. num. 211764). One filter was prepared for each serial dilution and then the agar plates were incubated at 32.5° C. for 6.5 hours followed by an overnight incubation at 32.5° C. At the 6.5 hour time point, the agar plates were removed from the incubator, and the filters were imaged by placing the plates on a CCD-based imager so that the bacterial colonies were facing the illumination source and CCD chip. Autofluorescence from each microcolony was detected using GFP excitation and GFP-LP emission filters. The autofluorescent signal from the microcolonies in each image was quantified using ImagePro software (Media Cybernetics, Inc., Version 4.5.0.19). Following the overnight incubation, the agar plates were inspected visually, and the number of macrocolonies present on the filters prepared with the $10^{-8}$ and $10^{-9}$ dilutions was counted. The number of macrocolonies on these two filters was used to calculate the number of bacteria added to each membrane and the concentration of bacteria in the initial overnight culture.

Results. In this example the bacterial cells were allowed to replicate and form microcolonies on a filter in agar plates. The microcolonies were detected by using the invention and identified by GFP-LP autofluorescence. The autofluorescent signal from the microcolonies in each image was quantified using Imagepro software. The autofluorescent signal in each image was plotted versus the number of bacteria added to each filter and the results are shown in FIG. 13. The data is linear over a 5 log range of bacteria levels. This range is significant because the range of some classical culture methods i.e. pour plates is only 2 logs. The results also show very strong linearity with an $R^2$ value of 0.9929. This value is within the acceptable $R^2$ values (0.8 to 1.2) for a new microbiological testing method (Evaluation, Validation, and Implementation of New Microbiological Testing Methods. 2000; PDA Journal of Pharmaceutical Science & Technology 54 (*Supplement* TR33), 1-41).

Example 9

Rapid Antimicrobial Preservative Effectiveness Testing without Sample Dilutions

Background and objectives: Antimicrobial preservatives are added to articles packaged in multidose containers to protect against growth of microorganisms that may be introduced by the manufacturing process or by customers during withdrawal of individual doses. Antimicrobial effectiveness must be demonstrated for pharmaceutical products that contain intrinsic antimicrobial activity or products that contain an antimicrobial preservative. The tests are very laborious and expensive to perform because of the large number of sample dilutions that must be analyzed. Typically an antimicrobial preservative effectiveness test requires analysis of hundreds of microbial culture plates. An important goal of this example is to demonstrate the potential of the invention to eliminate most of the labor of the test by obviating the need for sample dilutions.

Experimental methods. *E. coli* 8739 cells were grown overnight in TSB to a density of approximately $10^9$ cells/mi. Bacteria ($8.48 \times 10^6$ total or $2.12 \times 10^5$ cells/ml)) were added to 40 ml of sterile PBS or 40 ml of Osco Brand Sterile Preserved Saline Solution (Distributed by American Procurement and Logistics Company, Lot num. 1T016, Exp. June 03). These two solutions were incubated at room temperature for 168 hours. After 0, 24, 96 and 168 hours, 5 ml of the PBS containing bacteria and 5 ml of the Osco Saline containing bacteria were removed and added to separate tubes containing 45 ml of sterile D/E Neutralizing Broth (Becton Dickinson/Difco, cat num. 281910). The diluted sample was then deposited onto a black, mixed cellulose ester filter (Pall Gelman Laboratory; cat. num. 66585) using a vacuum filtration device and a sterile plastic funnel (Millipore Microfil® 100 ml Funnel, cat. num. MIHABG072). Each filter was placed on a separate agar plate containing Trypticase Soy Agar with Lecithin and Polysorbate 80 (Becton Dickinson BBL, cat. num. 211764). One filter was prepared for each solution at each time point. The agar plates were incubated at 32.5° C. for 6.5 hours. The agar plates were removed from the incubator, and the filters were imaged by placing the plates on a CCD-based imager so that the bacterial colonies were facing the illumination source and CCD chip. Autofluorescence was detected using GFP excitation and GFP-LP emission filters. The autofluorescent signal from the microcolonies in each image was quantified using ImagePro software (Media Cybernetics, Inc., Version 4.5.0.19). Using the standard curve shown in Example 8, the autofluorescent signal obtained by the ImagePro analysis was converted into the number of bacteria added per membrane and then the concentration of bacteria per ml of solution (PBS or Osco Saline) for each time point. Given the starting concentration of bacteria after 0 hours of incubation, the log decrease in bacterial concentration was calculated for the 24, 96, and 168 hour time points. After 0, 24, 96, and 168 hours, 100 µl was removed from the PBS and Osco Saline solutions containing bacteria and added to 900 µl of D/E Neutralizing Broth (1:10 dilution). Serial 10 fold dilutions in 1.0 ml sterile PBS were then made of the 1:10 dilution starting at $10^{-1}$ and ending at $10^{-6}$. The entire volume of the $10^{-1}$ through $10^{-6}$ dilutions was added to 30 ml of melted (45° C.) Trypticase Soy Agar with Lecithin and Polysorbate 80. The agar plates were allowed to cool at room temperature and then the plates were incubated overnight at 32.5° C. Bacterial colonies were visually counted in the plates of the two lowest dilutions which contained less than 300 colonies per plate. These numbers (multiplied by the appropriate dilution factor) were used to calculate the concentration of bacteria in the PBS and Osco Saline solutions. Given the starting concentration of bacteria after 0 hours of incubation, the log decrease in bacterial concentration was calculated for the 24, 96, and 168 hour time points. The log decrease in bacterial concentration as determined by the invention was plotted versus the log decrease in bacterial concentration as determined by the pour plate method (a classical, growth-based, microbiological enumeration method). The results are shown graphically in FIG. 14.

Results. The results in FIG. 14 show that the antimicrobial preservative in the Osco Saline solution (0.1% Sorbic Acid) is effective in decreasing the concentration of bacteria. No decrease in bacterial concentration was observed in the PBS. The data indicate a linear correlation ($R^2$=0.9633) between the two enumeration methods even though no dilutions were required by the invention. The results show the potential of the invention to save most of labor and materials by eliminating the onerous sample dilutions of the traditional method.

Example 10

Autofluorescence-based Detection of a Heat-stressed Biological Indicator using Non-magnified Large Area Imaging Background and objectives: The goals of this example are to show the potential application of the invention for applications that use thermo-resistant spores as biological indicators. One important application is sterilizer quantification methods for insuring the effectiveness of sterilization procedures in pharmaceutical and medical device manufacture and in clinical laboratories.

A further goal is to show the potential of the invention for simplifying biological indicator enumeration by lowering the number of required samples. In the traditional pour plate method, serial ten fold dilutions covering the entire possible range are necessary to quantify samples accurately. In this example, non-magnified large area imaging of the autofluorescence of the biological indicator *Geobacillus stearothermophilus* is used to quantify the viable spore concentration. The quantification is linear for about 3 orders of magnitude, decreasing the number of dilutions necessary to determine the number of viable spores remaining after heat stress accurately. An autofluorescent image is taken after a short period of growth, which is then analyzed to give an estimate of the initial concentration of viable heat-stressed *G. stearothermophilus* spores.

Experimental Methods: Spores of *Bacillus stearothermophilus* ATCC 7953 (Raven Biological Laboratories, Inc.) were diluted to a concentration of ~$2\times10^5$ spores/ml in sterile water and subjected to a variety of heat stresses ranging from 5 minutes at 110° C. to 15 minutes at 121° C. The heat treated spores and an untreated control were serially diluted by 10-fold in water up to a $\frac{1}{1000}$ dilution. For comparison, each sample was analyzed by the traditional pour plate method in addition to non-magnified large area imaging of autofluorescence. Pour plates were prepared by placing 1 ml of each dilution (including the undiluted stock) of each sample in a petri dish followed by the addition of 20 ml of molten Trypticase Soy Agar (TSA, BD catalogue no. 236950). After solidifying, the plates were incubated at 55° C. for 48 hours and counted manually. Plates that had between 30 and 300 colonies were used to calculate the spore titer, unless no plates had more than 30 colonies, in which case the plate containing 1 ml of undiluted stock was used.

To prepare microcolonies for large area imaging, 1 ml of the undiluted stock and 1 ml of the $\frac{1}{100}$ dilution were mixed with 15 ml sterile water and filtered through a black HABP filter (Millipore catalogue no. HABP04700) using vacuum filtration and a plastic funnel cup (Millipore Microfil V User Guide, PF07114, Rev A 3/00). After filtration, each filter was placed on a separate plate of TSA. Images were taken at t=0 hours using the non-magnifying CCD-based imager (described in Step 5 of Detailed description section and shown in FIG. 3). Autofluorescence was captured using the FITC optical filter set (Chroma; excitation 470/40 nm, emission 522/40 nm) with 5 second exposures. Plates were incubated at 55° C., and images were taken at 8 and 20 hours. Images were analyzed using Image Pro Plus software (version 4.1; Media cybernetics). The t=0 exposures were used to find dust and other fluorescent contaminants that may have been on the plates prior to growth. For each image, the sum of the pixel intensities of all objects (where objects are defined in this particular example as containing pixel intensities from 3200-65301 intensity units) minus the signal from contaminants at t=0 were compared to a standard curve generated using unstressed spores, and the spore titer was calculated from the standard curve. The value from either the undiluted sample or the $\frac{1}{100}$ dilution was used according to which one fell within the linear range of the standard curve. The calculated values of spores/ml from autofluorescence from non-magnified imaging were compared to the values calculated from the pour plate method.

Results: A plot of the heat-stressed spore titer calculated from pour plates vs. spore titer using autofluorescent large area imaging can be seen in FIG. 15. There is a good correlation between values from both methods, but four pour plates were necessary for each two autofluorescent images. In addition, pour plates take 48-72 hours to read, while the autofluorescent images can be taken and analyzed at 8-20 hours of growth.

Variations. Non-magnified large area imaging of autofluorescence could also be used to quantify viable cell concentrations of other biological indicator organisms, such as *Bacillus subtilis* and *Clostridium sporogenes*.

A variety of analyses of the autofluorescent images can be used to quantify cell concentrations. For example, object counts of microcolonies can be used instead of the sum of pixel intensities of the objects. Since the objects (microcolonies) are much smaller than full grown macrocolonies (that can be counted by eye), more can fit into the same area without sacrificing the accuracy that can be lost due to object overlap. In addition, more sophisticated object finding algorithms can be applied to the images to deal with local fluorescent background, touching objects, and presence of contaminating fluorescent particles.

Example 11

Autofluorescence-based Detection of Bacterial Microcolonies in Ground Beef

Background and objectives: This example illustrates the ability of the invention to reduce the time to detection of bacterial microcolonies in ground beef compared to compendial methods. Determination of total viable bacteria count in raw meat is essential for preventing early food spoilage. Current methods take two days, often requiring producers to ship the meat before getting test results. Reducing the time to detection of microbes could prevent foodborne disease incidents, manufacturing inefficiencies, and expensive recalls.

Experimental Methods: Lean ground beef (25 g) was diluted in 225 ml of 0.1 % peptone water and processed in a Stomacher to homogenize the sample. This sample was then diluted serially in 0.1% peptone water. Appropriate volumes of the $10^{-2}$, $10^{-3}$, $10^{-4}$ and $10^{-5}$ dilutions were added to PBS and then poured onto two filter membrane types (Millipore HABP Cat. No. HABP04700 0.45 μm and Chemunex CB0.4 0.4 μm Ref. no. 200-C20010-01) using vacuum filtration devices. Replicate samples were made for each dilution and filter type and incubated on TSA plates at 35° C. for 48 hrs. Images were captured using a CCD-based imager at 0, 6, 16, 24, and 48 hrs. A FITC optical filter set (Chroma; excitation 470/40 nm, emission 522/40 nm) was used and a 10 second image was captured under HDyn resolution using software control (Image Pro Plus). Images were also captured with white light reflectance for 10 seconds.

Results: Data was collected from the $10^{-4}$ and $10^{-5}$ dilutions on both membrane filter types. The data was analyzed by counting macrocolonies at 48 hours that were 0.5 mm in diameter or larger in reflectance images. These macrocolonies (≧0.5 mm) were then traced back to the 24, 16, and 6 hr time points, in reflectance and autofluorescent images. FIG. 16 shows the detection times of autofluorescent microcolonies and macrocolonies. Tracking the appearance over time of microcolonies that gave rise to the 48 hr macrocolonies showed that 100% of the macrocolonies were detected by the invention by 16 hrs. These results show the potential of the invention to reduce significantly the time required to achieve results compared to traditional methods.

Variations. The test in this example can be extended to test a variety of foods, including other meats, vegetables, beverages, and dairy products.

Example 12

Detection of Bacteria in a Complex Sample with Non-specific Magnetic Selection Followed by Microcolony Detection using Non-Magnified Large Area Imaging Objective: This example demonstrates an immunoassay method for selecting individual bacterial cells, non-specifically, from a complicated sample followed by rapid detection of growing microcolonies using non-magnified large area imaging. More specifically this example demonstrates the ability to select a range of bacteria efficiently from blood and then detect the growth of the bacteria using the growth direct method. This example shows that magnetic beads coated with a mixture of binding agents, can select divergent species of bacteria from a complex sample.

Experimental Methods: FIG. 17 shows the process this example follows to detect bacteria in a complex sample. First, bacterial cells and magnetic beads are added to the sample and incubated. The magnetic beads are bound to the bacterial cells; then the complexes are sequestered using magnetic force. The magnetic beads are resuspended (PBS), filtered, and plated on growth media. The resulting magnetic selection supernatant is also plated. After an incubation period, the filter is imaged at various time points using non-magnified large area imaging to detect microcolonies.

.An array of magnetic particles were made by coupling magnetic particles with active tosyl-groups (Dynal, Oslo, Norway, cat. no. 140.03) to several non-specific as well as specific binding agents. The agents include polymyxin B sulfate (Sigma; cat. no. P1004), polymyxin B nanoprotein (Sigma; cat. no. P2076), endotoxin neutralizing protein (Seikagaku America: naturally derived and recombinant versions, cat. no. 910140-1, 910130-1 and 910120-1), endotoxin inhibitor protein (Bachem; cat. no. H-1382), endotoxin substrate (Bachem; cat. no. L-1195), anti-lipotechoic acid antibody (QED; cat. no. 15711), anti-endotoxin antibody (QED cat. no. 15306 and 15301). The coated magnetic particles ($1 \times 10^8$ per 10 μl) were sonicated (1 min; setting 8; Fisher Scientific 550 Sonic Dismembrator). Combinations of the coated magnetic beads were then added to 1.5 ml tubes of blood (1 ml, Biochemed; Human blood, sodium citrate as anticoagulant, cat. no. 10762WB) spiked with approximately 1, 10 or 100 cells of Staphylococcus aureus (ATCC # 27694). The blood, bacteria and magnets were allowed to incubate (1 hour at room temp). After incubation the beads were magnetically selected using a magnetic separation device (Polysciences, Inc., Warrington, Pa., Cat. No. 8MB4111S) to capture and secure the magnetic particles. The blood was then decanted and plated on TSA (Difco, cat. no. 236950) as was the initial Staphylococcus aureus inoculums of 1, 10 and 100 cells (used as controls). The magnetic particles were resuspended (1 ml PBS) and the resulting liquid containing magnetic particles-bacterial complexes was filtered onto a membrane (Osmonics, poretics 47 mm, 0.22 μm pore, polycarbonate black filter, cat. no. 1213889), and the membrane was then placed on a TSA plate. At both the zero time point and after a short incubation period, the filters were imaged using non-magnified large area imaging to detect the autofluorescent microcolonies. The percent recovery was determined by comparing the inoculum count with the magnetic capture count and using the formula: (average magnetic capture/average inoculum count) ×100.

Results: FIG. 18 shows the experimental results demonstrating microcolony detection after the magnetic separation. This figure shows two images, taken at after zero and six hours of growth. The six hour image has putative microcolonies—these are bright spots that are not seen in the zero image. To confirm that these are indeed growing microbial microcolonies, the filters were allowed to incubate overnight and re-imaged. Macrocolonies were detected at the positions of the putative microcolonies confirming the rapid result. Greater than 90 percent recovery of Staphylococcus aureus was achieved for the 1 cell samples. The 10 and 100 cell sample had greater than 50 percent recovery.

Variations (broad binding agents): Numerous broadly reactive binding agents could be used including wheat germ agglutinin, anti-enterobacterial common antigen, anti-protein A, anti-protein G, LPS binding protein, mucin (bacterial binding agent), CD14 (binds both LPS and LPS bacterial complexes), collectins (these bind bacteria during phagocytosis or during the complement cascade), subunits of complement itself such as C3b and C4b, human scavenger receptors (cell receptors that bind bacterial components) and tectonics (carbohydrate binding proteins).

Variations (specific binding agents): A variety of types of category-binding molecules, including antibodies, aptamers, and ligands, can be used to specifically select a range of cells types from complex samples. In this example variation, selection of an E. coli O157:H7 is achieved using an E. coli O157:H7 specific antibody.

Variation of Experimental Method: In this variation, detection of bacteria in a complex sample is achieved with analyte-specific magnetic selection. The selection is followed by microcolony detection using non-magnified large area imaging. FIG. 17 shows the method to use for this example. A sample containing E. coli O157:H7 is mixed with magnetic particles. The sample is then magnetically selected, filtered and imaged at a series of time points using non-magnified large area imaging. Anti-E. coli O157:H7 magnetic particles are made by coupling tosyl-modified magnetic particles (Dynal, Oslo, Norway, cat. No. 140.03; coupling performed according to manufacturer's recommendations) to polyclonal antibodies raised against E. coli O157:H7 (Bio-Trace affinity purified; Kirkegaard & Perry Laboratories, Gaithersburg, Md., Cat. No. 01-95-90). Anti-E. coli O157:H7 magnetic particles ($1 \times 10^8$/10 μi) were sonicated (1 min; setting 8; Fisher Scientific 550 Sonic Dismembrator). The magnetic beads are then added to blood (1 ml; Biochemed; Human blood, sodium citrate as anticoagulant, cat. no. 10762WB) spiked with E. coli O157:H7 (Strain DEC 3B, Dr. Tom Whittam, Pennsylvania State University). E. coli O157;H7 microcolony growth and detection are achieved follow the same steps used above in this example.

Example 13

Antimicrobial Susceptibility Testing using in situ Replication and Non-magnified Large Area Imaging Background and objectives: The significance of antimicrobial susceptibility testing for determining appropriate therapy is discussed in the background section. Monitoring microbial growth on solid medium is common and has some significant advantages over growth in liquid culture. It is possible to inexpensively, simultaneously, and quantitatively determine the susceptibility of a strain of bacteria to several antibiotics without the use of instrumentation (e.g., using disk diffusion assays), but the current methods require a purified colony and thus cannot usually be performed for 1-2 days after the patient's sample has been processed. Such delays can be life threatening. Furthermore, another 1-2 days is generally required to detect and analyze the result of a antimicrobial susceptibility test.

Objective. The example demonstrates the use of the invention to determine the antibiotic susceptibility of bacterial strains rapidly. The principle of the method is diagrammed in FIG. 19. In the experiment described below, resistant and sensitive strains were grown on media with and without antibiotic and microcolonies were detected as in the previous example. The approach offers the potential to shorten significantly the prolonged growth steps (colony purification and growth in antibiotic) that currently can delay implementation of appropriate antimicrobial therapy.

Methods. A sensitive (*E. coli* MG1655) and resistant (*E. coli* MG1655/pLafr I) strain of bacteria were deposited on filters as in the previous example (Example 1). Filters containing approximately 1000 resistant bacteria were placed on LB plates (LB agar; Difco) that either contained antibiotic (tetracycline; 64 μg/ml) or did not contain antibiotic. After incubation at 37° C. (3 hrs), the filters were stained and imaged as in (Example 1).

Results. FIG. 20 shows the results of antimicrobial susceptibility testing using CCD-based non-magnified large area imaging. CCD imaging detected microcolonies on the membrane containing resistant bacteria but not on the membrane containing sensitive bacteria (compare the rows labeled "resistant strain" and "sensitive strain" in the leftmost column labeled: 3 hour+tet, CCD). The intensity data obtained from image analysis quantified this observation (bar graph). High power fluorescence microscopy confirmed that the resistant strain formed microcolonies after 3 hours of incubation, while the sensitive strain did not. (Microscopic analysis indicated that incubation of the sensitive strain in the presence of antibiotic leads to aberrant bacterial morphologies [compare the two microscopic images in the bottom row labeled "sensitive strain"].).

The results of this experiment show that detecting microcolonies using non-magnified large area imaging is a rapid and sensitive method for antimicrobial susceptibility testing.

Variations: Some variations on the antimicrobial susceptibility test include using different signal moieties. Viability stains, such as Syto 9 and other Syto family members (Molecular Probes), esterase substrates such as fluorescein diacetate or chemchrome V6 (Chemunex), labeled antibodies, or metabolites that yield fluorescent products, could be substituted for the nucleic acid stain in this assay. The natural autofluorescence of the cellular target cells could also be used to detect the microcolonies. Microcolony growth could also be used to monitor geometrical growth constraints as with antimicrobial susceptibility testing disk diffusion or the E test methods (AB biodisk NA Inc.; E-test strips). The antimicrobial susceptibility assay can also be expanded to include simultaneous identification of various microbes with different fluorescently labeled antibodies.

Example 14

Rapid Antimicrobial Susceptibility Testing using the Disk Diffusion Method and Non-magnified Large Area Imaging Objective: This example demonstrates the use of the invention to determine the antibiotic susceptibility of bacterial strains rapidly using the disk diffusion method. Disks that are impregnated with a known concentration of an antibiotic are placed on plates containing a large number of cells from a purified microbial culture. The antibiotic diffuses from the disk creating a radial gradient of antibiotic concentration centered on the disk (i.e., the closer to the disk, the higher the concentration of antibiotic). Highly resistant strains can grow in the presence of the disks even near the edge where the antibiotic concentration is highest. Less resistant strains grow outside of a zone of inhibition surrounding the disk. The width of the zone of inhibition is correlated with the level of antibiotic resistance for the strain.

The zone of inhibition is traditionally measured by the naked eye after an overnight growth. This example demonstrates the ability to determine the zone of inhibition in hours by detecting the growth of microcolonies using non-magnified large area imaging.

Experimental Methods: The strains, used in the example and described in Example 13, were diluted to $10^6$ CFU/ml and plated on TSA media. A tetracycline diffusion disk (Hardy Diagnostics; 30 μg tetracycline, cat. no. Z9121) was then placed on the plates. The plates were allowed to incubate at 37° C. for 5 hours. The microcolonies were imaged using microcolony autofluorescence and non-magnified large area imaging as in previous examples.

Results: FIG. 21 shows the results of a rapid antimicrobial susceptibility test using non-magnified large area imaging. The CCD-based imaging detected autofluorescent resistant colonies growing near an antibiotic diffusion disk after only 5 hours. The zone of inhibition was comparable to that obtained by visual inspection after overnight growth. The results of this experiment show that detecting zones of inhibition based on microcolony growth is more rapid than the traditional disk diffusion method but can yield comparable results.

Variations: This technique can be used with most antibiotic diffusion disks and most microbes.

Example 15

Rapid Antimicrobial Susceptibility Testing using the E-test and Non-magnified Large Area Imaging Objective: This example demonstrates the use of the invention to rapidly determine the antibiotic susceptibility of bacterial strains using an E-test™ antibiotic test strip. The E-test™ strip is impregnated with a range of concentrations of tetracycline enabling the user to use one strip to determine the lowest antibiotic concentration needed to inhibit the growth of the tested bacteria. This minimal inhibitory concentration is based on the visualization of zones with no growth, called the zone of inhibition. The zone of inhibition is traditionally measured by the naked eye after an overnight growth. This example demonstrates the ability to determine the zone of inhibition in hours by detecting the growth of microcolonies using non-magnified large area imaging.

Experimental Methods: The strains, used in the example and described in Example 13, were diluted to $10^6$ CFU/ml and plated on TSA media. The E-test™ strip (Hardy diagnostics: 0.016-256 μg tetracycline, cat. no. 51002258) was then placed on the plates which were allowed to incubate at 37° C. for five hours. The microcolonies growing on or near the test strip were imaged using microcolony autofluorescence and non-magnified large area imaging as in previous examples. After imaging, the plates were allowed to incubate overnight.

Results: FIG. 22 shows the results of a rapid antimicrobial susceptibility E-test™ using non-magnified large area imaging. Non-magnified, large area imaging detected autofluorescent resistant microcolonies growing near the E-test™ antibiotic test strip. A zone of inhibition comparable with that observed after overnight growth could be determined after five hours of growth. The results of this experiment show that detecting microcolonies using non-magnified large area imaging is a rapid and sensitive method greatly reducing the time to result for an E-test™.

Variations: This technique is applicable to E-Test™ strips impregnated with a variety of antibiotics.

OTHER EMBODIMENTS

All patents, patent applications, and publications referenced in this application are hereby incorporated by reference. Other embodiments of the invention will be apparent to those skilled in the art from consideration of the specification and practice of the invention disclosed herein. It is intended that the specification and examples be considered as exemplary only, with a true scope and spirit of the invention being indicated by the following claims. Examples of other embodiments that may be adapted to the methods described herein are found in U.S. application Ser. No. 10/237,010, entitled "RAPID AND SENSITIVE DETECTION OF CELLS AND VIRUSES", filed Sep. 6, 2002 and U.S. application Ser. No. 10/236,105, entitled "RAPID AND SENSITIVE DETECTION OF MOLECULES", filed Sep. 6, 2002, each of which is hereby incorporated by reference.

The invention claimed is:

1. A method for detecting microcolonies of living target cells in a sample, said method comprising the steps of:
   (a) depositing living target cells present in said sample in a detection zone comprising a detection area at a density of less than 100 target cells per mm² of the detection area, wherein within said detection zone said cells are randomly dispersed and immobilized;
   (b) allowing the formation of one or more microcolonies of said target cells by in situ replication; and
   (c) detecting said one or more microcolonies;
wherein the longest linear dimension of said detection area is greater than 1 mm;
said one or more microcolonies have a measurement of less than 50 microns in at least two orthogonal dimensions; said detecting does not entail magnification of more than 5×; said detecting detects a property of said one or more microcolonies that does not depend on the addition of a signalling moiety or category binding molecule; and said cells in said one or more microcolonies remain competent to replicate following said detecting.

2. The method of claim 1, wherein said target cells are randomly dispersed in a detection zone at a density of less than 10 target cells per mm² of the detection area.

3. The method of claim 1, wherein said target cells are randomly dispersed in a detection zone at a density of less than 1 target cells per mm² of the detection area.

4. The method of claim 1, wherein said detecting detects a single microcolony in the detection area.

5. The method of claim 1, wherein said detecting detects overlapping or contiguous microcolonies.

6. The method of claim 1, wherein said detecting does not entail magnification of more than 2×.

7. The method of claim 1, wherein said detecting does not entail magnification of more than 1×.

8. The method of claim 1, wherein said detecting does not entail magnification of more than 0.2×.

9. The method of claim 1, wherein the mean number of cells in said one or more microcolonies is less than 50,000 cells.

10. The method of claim 1, wherein said target cells are bacteria.

11. The method of claim 1, wherein said target cells are eukaryotic cells.

12. The method of claim 1, wherein said target cells are parasites of humans, animals, or plants.

13. The method of claim 1, wherein said detecting detects and identifies microcolonies from more than one non-overlapping category of cell.

14. The method of claim 1, wherein said sample comprises fluids or tissues obtained from a multicellular organism.

15. The method of claim 1, wherein said sample comprises the bodily fluids or tissues of an animal.

16. The method of claim 1, wherein said sample is obtained from a human.

17. The method of claim 1, wherein said sample is obtained from a non-human vertebrate.

18. The method of claim 1, wherein said sample is selected from the group consisting of: respiratory, urogenital, reproductive, central nervous system, urine, blood, dermal, plasma, serum, saliva, wound tissue, wound exudate, biopsy, feces, reproductive tract, and solid tissue samples, and samples obtained by processing of said samples.

19. The method of claim 1, wherein said sample is a blood or urine sample.

20. The method of claim 1, wherein said sample is a plant sample.

21. The method of claim 1, wherein said sample is obtained by sampling environmental air or water, or surfaces, objects, or organisms exposed to the environment.

22. The method of claim 1, wherein said sample is obtained from a material selected from the group consisting of raw, finished, or in-process material in the manufacture of pharmacological, cosmetic, blood, or other products for topical or internal use in humans or animals; raw, in-process, or finished material in the manufacture of foods or beverages; raw, in-process, or finished material in the manufacture of medical or in vitro diagnostic devices, chemical products; industrial surfaces; instrumentation; and machinery.

23. The method of claim 1, wherein said detection zone is contacted with a liquid medium comprising one or more substances that facilitate replication of target cells.

24. The method of claim 1, wherein said cells are deposited directly on a solid or semi-solid growth medium.

25. The method of claim 1, wherein, prior to step (a), a selection method is used to deposit complexes of one or more of said target cells and a selection moiety in said detection zone, wherein said selection method is selected from the group consisting of magnetic selection, centrifugation, settling, and filtration.

26. The method of claim 1, wherein said target cells are deposited in said detection zone using a selection method selected from the group consisting of magnetic selection, centrifugation, settling, and filtration, wherein a selection moiety is not employed.

27. The method of claim 1, wherein, prior to step (a), said sample is treated to liquefy and/or homogenize said sample.

28. The method of claim 1, wherein, prior to step (a), said sample is treated to remove substances or objects other than said target cells.

29. The method of claim 1, wherein step (c) comprises at least two cycles each of which comprises a period in which cells are allowed to replicate followed by a detection step.

30. The method of claim 1, further comprising the step of repeating steps (a)-(c) with one or more additional samples, wherein said repeating is automated.

31. The method of claim 1, wherein said detecting comprises illuminating one or more microcolonies to generate a detectable signal.

32. The method of claim 1, wherein said detecting detects fluorescence.

33. The method of claim 1, further comprising the step, prior to or during step (c), of contacting said sample with a signaling moiety that associates either directly or indirectly with said target cells.

34. The method of claim 1, further comprising the step, prior to or during step (c), of contacting said sample with a category-binding molecule under conditions that allow the formation of one or more complexes between said category-binding molecule and one or more category-specific binding sites on one or more of said target cells.

35. The method of claim 1, wherein said replication and said detecting occur in a vessel constructed so as not to allow additional cells to enter or cells in the sample to exit.

36. The method of claim 1, wherein said replication and said detecting occur in a vessel that has a bar code or equivalent label for tracking the sample automatically.

37. The method of claim 1, wherein said replication and said detecting occur on a surface with registration marks to facilitate alignment of multiple images of the same surface.

38. The method of claim 1, wherein said detecting detects control marks or control cells in a specified region of the detection zone.

39. The method of claim 1, wherein said detecting employs optical filters adapted to detect a signal derived from the illumination of said target cells.

40. The method of claim 1, wherein said detecting employs a photoelectric detector.

41. The method of claim 1, wherein said detecting employs a photoelectric array detector.

42. The method of claim 1, wherein said detecting does not employ an image intensifier.

43. The method of claim 1, wherein said detecting employs a photomultiplier tube detector.

44. The method of claim 1, wherein said detecting employs a photodiode detector.

45. The method of claim 1, wherein said detecting employs a photosensitive film.

46. The method of claim 1, further comprising the step, during or after step (c), of quantifying the number of microcolonies.

47. The method of claim 1, further comprising the step, during or after step (c), of determining the category of said target cells by analyzing an image of said detection area using image analysis software.

48. The method of claim 1, further comprising the step, during or after step (c), of determining the locations in the detection zone of said one or more microcolonies by analyzing an image of said detection area using image analysis software.

49. The method of claim 1, wherein said detecting detects one or more naturally occurring optical properties of said one or more microcolonies.

50. The method of claim 1, wherein said detecting is carried out using an instrument comprising
(a) a photoelectric array detector having an optical resolution of less than 50 microns and encircled or ensquared energy values of greater than 50% per pixel; and
(b) an illumination source,
wherein said instrument illuminates and simultaneously images a detection area having at least one dimension that is $\geq 1$ cm, and wherein said instrument does not optically magnify more than 5 fold.

51. The method of claim 9, wherein said one or more microcolonies comprise less than 10,000 cells.

52. The method of claim 9, wherein the mean number of cells in said one or more microcolonies is less than 1000.

53. The method of claim 9, wherein the mean number of cells in said one or more microcolonies is less than 100.

54. The method of claim 9, wherein the mean number of cells in said one or more microcolonies is less than 10.

55. The method of claim 9, wherein said one or more microcolonies have a measurement of less than 25 microns in the longest linear dimension.

56. The method of claim 9, wherein said one or more microcolonies have a measurement of less than 10 microns in the longest linear dimension.

57. The method of claim 11, wherein said target cells are mold or fungal cells.

58. The method of claim 11, wherein said target cells are human, animal, or plant cells.

59. The method of claim 25, wherein, prior to step (a), said target cells are contacted with target cell-specific magnetic selection moieties and complexes of one or more of said target cells and said selection moiety are subsequently deposited on said detection surface using magnetic force.

60. The method of claim 25, wherein said target cells are contacted in a liquid with said target-cell specific selection moieties that have an average density greater than the average density of said liquid and wherein complexes of one or more of said target cells and said selection moiety are subsequently deposited on said detection surface using gravitational, centrifugal, or centripetal force.

61. The method of claim 30, wherein said samples are automatically loaded into an instrument that comprises a detector.

62. The method of claim 30, wherein said samples are automatically deposited in a series of detection zones that are physically associated and that are automatically and successively loaded into an instrument that comprises a detector.

63. The method of claim 31, wherein said detecting detects light emitted, scattered, reflected, or absorbed as a result of illumination of said one or more microcolonies.

64. The method of claim 31, wherein said illuminating employs one or more lasers.

65. The method of claim 31, wherein said illuminating employs one or more light-emitting diodes.

66. The method of claim 31, wherein said illuminating employs a source of white-light.

67. The method of claim 31, wherein said illuminating is through one or more optical filters that only pass selected wavelengths of light.

68. The method of claim 32, wherein said fluorescence is autofluorescence emitted by said microcolonies.

69. The method of claim 33, wherein said signaling moiety is associated with a category-binding molecule.

70. The method of claim 33, wherein said signaling moiety has fluorescent signaling character.

71. The method of claim 33, wherein said signaling moiety has chromogenic signaling character.

72. The method of claim 33, wherein said signaling moiety has light-scattering signaling character.

73. The method of claim 33, wherein said signaling moiety is a viability stain for staining living cells.

74. The method of claim 33, wherein said signaling moiety comprises one or more compounds that are not detectable until upon association with said target cells, said signaling moiety is acted on by a constituent of said target cells or by a physiological, physical, or micro-environmental state of said target cells.

75. The method of claim 34, wherein said category-binding molecule comprises an antibody, aptamer, or ligand.

76. The method of claim 34, wherein said category-binding molecule is labeled, either directly or indirectly, with one or more signaling moieties.

77. The method of claim 34, wherein said category binding molecule is a member of an ensemble of category-binding molecules, wherein said ensemble comprises one family of category-binding molecules specific for each non-overlapping category of target cells to be detected.

78. The method of claim 41, wherein said photoelectric detector comprises a CCD detector.

79. The method of claim 46, wherein said determining comprises analyzing an image of said detection area.

80. The method of claim 48, further comprising the step, during or after step (c), of comparing said locations in the detection zone of individual microcolonies to previously determined locations of the same microcolonies.

81. The method of claim 49, wherein said optical property or properties comprises autofluorescence.

82. The method of claim 49, wherein said optical property or properties comprises thermal radiation.

83. The method of claim 49, wherein said optical property or properties comprises optical absorbance.

84. The method of claim 49, wherein said optical property or properties comprises fluorescence polarization.

85. The method of claim 49, wherein said optical property or properties comprises optical reflectance.

86. The method of claim 49, wherein said optical property or properties comprises light scattering.

87. The method of claim 59, wherein said target cell-specific magnetic selection moieties comprise magnetic particles that are conjugated to category-binding molecules.

88. The method of claim 69, wherein said signaling moiety is a particle or is physically associated with a particle.

89. The method of claim 70, wherein said signaling moiety is selected from the group consisting of organic fluorphores, up-regulated phosphors, lanthanides, quantum dots, enzymes that generate fluorescent product from non-fluorescent substrates, and fluorescently dyed particles.

90. The method of claim 70, wherein said signaling moiety is a fluorescent stain for cells.

91. The method of claim 70, wherein said signaling moiety has chemiluminescent signaling character.

92. The method of claim 72, wherein said signaling moiety is a resonance light scattering particle or plasmon resonance particle.

93. The method of claim 76, further comprising the step, prior to step (c), of removing any unbound category-binding molecules from said one or more complexes.

94. The method of claim 77, wherein each of said families of category-binding molecules is labeled with a signaling moiety that emits a signal of a distinct signal class or signal signature.

95. The method of claim 77, wherein said ensemble of category-binding molecules has a family complexity of 1.

96. The method of claim 77, wherein said ensemble of category-binding molecules has a family complexity that is greater than 1.

97. The method of claim 96, wherein said ensemble has a family complexity $\geq 5$.

98. The method of claim 80, wherein said image analysis software comprises algorithms for discerning objects that change size over time from objects that do not change size over time.

99. The method of claim 83, wherein said optical absorbance is in the infrared region.

* * * * *

UNITED STATES PATENT AND TRADEMARK OFFICE
CERTIFICATE OF CORRECTION

PATENT NO.         : 7,582,415 B2
APPLICATION NO.    : 10/236107
DATED              : September 1, 2009
INVENTOR(S)        : Straus It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 410 days Delete the phrase "by 410 days" and insert -- by 611 days --

Signed and Sealed this

Twenty-fourth Day of August, 2010

David J. Kappos
*Director of the United States Patent and Trademark Office*